(12) United States Patent
Rueckle et al.

(10) Patent No.: US 7,705,052 B2
(45) Date of Patent: Apr. 27, 2010

(54) SULFONAMIDE DERIVATIVES FOR THE TREATMENT OF DIABETES

(75) Inventors: Thomas Rueckle, Plan-les-Ouates (CH); Pierre-Alain Vitte, Cranves-Sales (FR); Jean-Pierre Gotteland, Beaumont (FR)

(73) Assignee: Merck Serono SA, Coinsins (CH)

( * ) Notice: Subject to any disclaimer, the term of this patent is extended or adjusted under 35 U.S.C. 154(b) by 0 days.

(21) Appl. No.: 10/571,466

(22) PCT Filed: Sep. 13, 2004

(86) PCT No.: PCT/EP2004/052143

§ 371 (c)(1), (2), (4) Date: Aug. 25, 2006

(87) PCT Pub. No.: WO2005/025558

PCT Pub. Date: Mar. 24, 2005

(65) Prior Publication Data

US 2007/0043027 A1    Feb. 22, 2007

(30) Foreign Application Priority Data

Sep. 12, 2003   (EP)   ................................. 03102742

(51) Int. Cl.
- A61K 31/18 (2006.01)
- A61K 31/54 (2006.01)
- A61K 31/535 (2006.01)
- A61K 31/425 (2006.01)
- A61K 31/24 (2006.01)
- A61K 31/155 (2006.01)

(52) U.S. Cl. ......................... 514/601; 514/3; 514/227.5; 514/231.5; 514/369; 514/535; 514/603; 514/635; 514/866

(58) Field of Classification Search .............. 514/231.5, 514/227.5, 601, 603, 369, 535, 635, 866
See application file for complete search history.

(56) References Cited

U.S. PATENT DOCUMENTS

| | | | | |
|---|---|---|---|---|
| 3,174,901 A | * | 3/1965 | Sterne | ......................... 514/635 |
| 3,454,635 A | * | 7/1969 | Weber et al. | .................. 564/41 |
| 4,927,831 A | | 5/1990 | Malamas | |
| 6,335,334 B1 | | 1/2002 | Schindler et al. | |
| 2007/0043027 A1 | | 2/2007 | Rueckle et al. | |

FOREIGN PATENT DOCUMENTS

| | | |
|---|---|---|
| EP | 1 088 815 | 4/2001 |
| EP | 1 088 821 | 4/2001 |
| EP | 1 193 267 | 4/2002 |
| EP | 1 193 268 | 4/2002 |
| EP | 1193268 A1 * | 4/2002 |
| WO | 01/23378 | 4/2001 |
| WO | 02/26733 | 4/2002 |
| WO | 02/28856 | 4/2002 |
| WO | 02/100396 | 12/2002 |

OTHER PUBLICATIONS

Http://en.wikipedia.org/wiki/Biguanide (Sep. 2006).*

Rueckle, Thomas et al., "Design, synthesis and biological properties of the first generation of novel, potent and selective (Benzoylaminomethyl)-thiophene sulfonamide inhibitors of the c-Jun-N-terminal-Kinase (JNK).", Abstracts of Papers American Chemical Society, vol. 226, No. 1-2, Page Medi 28, 2003.
Bennett, Brydon.L. et al., "JNK: A new therapeutic target for diabetes" Current Opinion in Pharmacology, vol. 3, No. 4, pp. 420 to 425, 2003.
Manning, Anthony M. et al., Targeting JNK for therapeutic benefit: from junk to gold? Nature Reviews. Drug Discovery, vol. 2, No. 7, pp. 554-565, 2003.
Schweizer, Ernst H. et al., "Sulfonyliminoimidazolines. A new class of Oral Hypoglycemic Agents. 1. 1-[[p-[2-(Acylamino)ethyl]Phenylsulfonyl]-2-iminoimidazolidines", Journal of Medicinal Chemistry, vol. 26, pp. 964-970, 1983.
Henquin, J.C: "Fifty years of hypoglycaemic sulphonamides", Revue Francaise D'Endocrinologie Clinique-Nutrition ET Metabolisme, vol. 34, No. 3, pp. 255 to 259, 1993.
Reaven, Gerald M. et al, Nonketotic Diabetes Mellitus: Insulin Deficiency or Insulin Resistance?, The American Journal of Medicine, vol. 60, pp. 80-88, 1976.
Stout, Robert W. , "Overview of the Association Between Insulin and Atherosclerosis", Metabolism, Vo. 34, No. 12, pp. 7-12, 1985.
Diamanti-kandarakis et al., "Therapeutic effects of metformin on Insulin resistance and hyperandrogenism in polycystic ovary syndrome", Society of the European Journal of Endocrinology, vol. 138 pp. 269-274, 1998.
Dunaif, Andrea, "Insulin Resistance and the Polycystic Ovary Syndrome: Mechanism and Implications for Pathogenesis", Endocrine Reviews, vol. 18, No. 6, pp. 774-800, 1997.
U.S. Appl. No. 12/565,988, filed Sep. 24, 2009, Rueckle, et al.

* cited by examiner

*Primary Examiner*—Kevin Weddington
(74) *Attorney, Agent, or Firm*—Oblon, Spivak, McClelland, Maier & Neustadt, L.L.P.

(57) ABSTRACT

The present invention is related to the use of sulfonamide derivatives in the treatment of metabolic disorders mediated by insulin resistance or hyperglycemia, comprising diabetes type II, inadequate glucose tolerance, insulin resistance, obesity, polycystic ovary syndrome (PCOS). Formula (I). $R^1$ is selected from the group comprising or consisting of hydrogen, $C_1$-$C_6$-alkoxy, $C_1$-$C_6$-alkyl, $C_2$-$C_6$-alkenyl, $C_2$-$C_6$-alkynyl, amino, sulfanyl, sulfinyl, sulfonyl, sulfonyloxy, sulfonamide, acylamino, aminocarbonyl, $C_1$-$C_6$ alkoxycarbonyl, aryl, heteroaryl, carboxy, cyano, halogen, hydroxy, nitro, hydrazides. $R^2$ is selected from the group comprising or consisting of hydrogen, COOR3, —CONR³R³', OH, a $C_1$-$C_4$ alkyl substituted with an OH or amino group, a hydrazido carbonyl group, a sulfate, a sulfonate, an amine or an ammonium salt. Y is an 4-12-membered saturated cyclic or bicyclic alkyl containing at least one nitrogen atom, whereby one nitrogen atom within said ring is forming a bond with the sulfonyl group of formula I thus providing the sulfonamide.

(I)

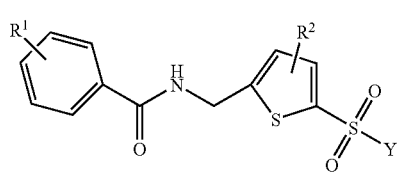

9 Claims, No Drawings

SULFONAMIDE DERIVATIVES FOR THE TREATMENT OF DIABETES

FIELD OF THE INVENTION

The present invention is related to sulfonamide derivatives for the treatment of metabolic disorders mediated by insulin resistance or hyperglycemia, comprising diabetes type II, inadequate glucose tolerance, insulin resistance, obesity, polycystic ovary syndrome (PCOS).

BACKGROUND OF THE INVENTION

Diabetes mellitus is a serious metabolic disease that is defined by the presence of chemically elevated levels of blood glucose (hyperglycemia). The term diabetes mellitus encompasses several different hyperglycemic states. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin that are insufficient to maintain blood glucose levels within the physiological range. Conventionally, Type 1 diabetes is treated by administration of replacement doses of insulin, generally by a parenteral route.

Type 2 diabetes is an increasingly prevalent disease of aging. It is initially characterized by decreased sensitivity to insulin and a compensatory elevation in circulating insulin concentrations, the latter of which is required to maintain normal blood glucose levels.

The prevalence of insulin resistance in glucose intolerant subjects is well known. Reaven et al (*American Journal of Medicine*, 60, 80 (1976)) used a continuous infusion of glucose and insulin (insulin/glucose clamp technique) and oral glucose tolerance tests to demonstrate that insulin resistance exists in a diverse group of non-obese, non-ketotic subjects. These subjects ranged from borderline glucose tolerant to overt, fasting hyperglycemia. The diabetic groups in these studies included both insulin dependent (IDDM) and non-insulin dependent (NIDDM) subjects.

Coincident with sustained insulin resistance is the more easily determined hyperinsulinemia, which may be measured by accurate determination of circulating plasma insulin concentration in the plasma of subjects. Hyperinsulinemia may be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia and insulin resistance with obesity has been well established by numerous experimental, clinical and epidemiological studies (Stout, *Metabolism*, 34, 7 (1985)).

The association of hyperinsulinemia and insulin resistance with Polycystic Ovary Syndrome (PCOS) is also well acknowledged (Diamanti-Kandarakis et al.; Therapeutic effects of metformin on insulin resistance and hyperandrogenism in polycystic ovary syndrome; *European Journal of Endocrinology* 138, 269-274 (1998), Andrea Dunaif; Insulin Resistance and the Polycystic Ovary Syndrome: Mechanism and Implications for Pathogenesis; *Endocrine Reviews* 18(6), 774-800 (1997)).

Type II diabetes mellitus is currently treated with sulfonylureas, biguanides, such as Metformin and thiazolidenediones, such as Troglitazone, Rosiglitazone or Pioglitazone, as oral hypoglycemic agents.

The compounds of the present invention are disclosed in WO 01/23378, WO 02/28856 and WO 02/26733 (Applied Research Systems ARS NV) in which sulfonamide derivatives of formula (A) are described in particular for the treatment of neuronal disorders, autoimmune diseases, cancer and cardiovascular diseases:

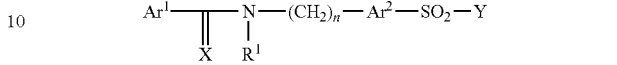

SUMMARY OF THE INVENTION

The present invention relates to the use of sulfonamide derivatives of formula (I) for the manufacture of a medicament for the treatment of metabolic disorders mediated by insulin resistance or hyperglycemia, comprising diabetes type II, inadequate glucose tolerance, insulin resistance, obesity, polycystic ovary syndrome (PCOS).

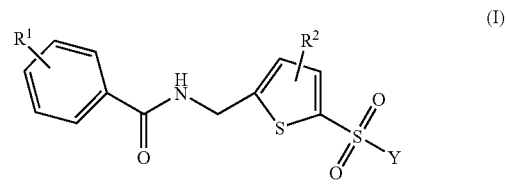

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic hetero aromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"heterocycloalkyl" refers to a $C_3$-$C_8$-cycloalkyl group according to the definition above, in which 1 to 3 carbon atoms are replaced by hetero atoms chosen from the group consisting of O, S, NR, R being defined as hydrogen or $C_1$-$C_6$ alkyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered hetero-cycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —N$^+$RR'R", where each R, R', R" is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, animals formed by ring closure for instance in an effort to obtain a protective group.

"Pharmaceutically acceptable salts or complexes" refers to salts or complexes of the below-identified compounds of formula (I) that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, methanesulfonic acid and poly-galacturonic acid. Said compounds can also be administered as pharmaceutically acceptable quaternary salts known by a person skilled in the art, which specifically include the quaternary ammonium salt of the formula —NR, R', R"⁺Z⁻, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

It was now found that sulfonamide derivatives according to formula I are suitable for the treatment of metabolic disorders mediated by insulin resistance or hyperglycemia, comprising diabetes type II, inadequate glucose tolerance, insulin resistance, obesity, polycystic ovary syndrome (PCOS).

In the compounds according to formula I the substituents are as follows:

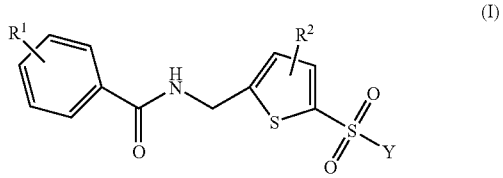

(I)

Y is an unsubstituted or a substituted 4-12-membered saturated cyclic or bicyclic alkyl ring containing at least one nitrogen atom (heterocycle), whereby one nitrogen atom within said ring is forming a bond with the sulfonyl group of formula I, thus providing a sulfonamide.

$R^1$ is selected from the group comprising or consisting of hydrogen, unsubstituted or a substituted $C_1$-$C_6$-alkoxy, unsubstituted or a substituted $C_1$-$C_6$-alkyl, unsubstituted or a substituted $C_2$-$C_6$-alkenyl, unsubstituted or a substituted $C_2$-$C_6$-alkynyl, amino, sulfanyl, sulfinyl, sulfonyl, sulfonyloxy, sulfonamide, acylamino, aminocarbonyl, unsubstituted or a substituted $C_1$-$C_6$ alkoxycarbonyl, unsubstituted or a substituted aryl, unsubstituted or a substituted heteroaryl, carboxy, cyano, halogen, hydroxy, nitro, hydrazide.

More specifically, $R^1$ is selected from the group consisting of hydrogen, halogen (e.g. chlorine), $C_1$-$C_6$ alkyl (e.g. methyl or ethyl) or $C_1$-$C_6$ alkoxy (e.g. methoxy or ethoxy). Most preferred is halogen, in particlar chlorine.

$R^2$ is selected from the group comprising or consisting of hydrogen, $COOR^3$, —$CONR^3R^{3'}$, OH, a $C_1$-$C_4$ alkyl substituted with an OH or amino group, a hydrazido carbonyl group, a sulfate, a sulfonate, an amine or an ammonium salt. Thereby, $R^3$, $R^{3'}$ are independently selected from the group consisting of H, $C_1$-$C_6$-alkyl, $C_2$-$C_6$-alkenyl, aryl, heteroaryl, aryl-$C_1$-$C_6$-alkyl, heteroaryl-$C_1$-$C_6$-alkyl.

According to one embodiment the cyclic amines Y have either of the general formulae (a) to (d):

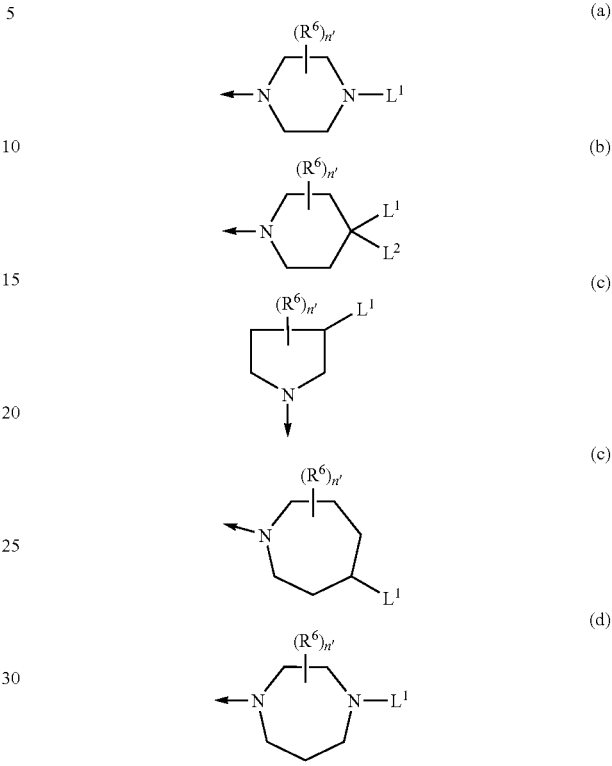

Thereby, $L^1$ and $L^2$ are independently selected from each other from the group consisting of unsubstituted or a substituted $C_1$-$C_6$-alkyl, unsubstituted or a substituted $C_2$-$C_6$-alkenyl, unsubstituted or a substituted $C_2$-$C_6$-alkynyl, unsubstituted or a substituted $C_4$-$C_8$-cycloalkyl optionally containing 1-3 heteroatoms and optionally fused with aryl or heteroaryl.

Alternatively, $L^1$ and $L^2$ are independently selected from the group consisting of unsubstituted or a substituted aryl, unsubstituted or a substituted heteroaryl, unsubstituted or a substituted aryl-$C_1$-$C_6$-alkyl, unsubstituted or a substituted heteroaryl-$C_1$-$C_6$-alkyl, —C(O)—$OR^3$, —C(O)—$R^3$, —C(O)—$NR^3R^3$, —$NR^3R^3$, —$NR^3C(O)R^3$, —$NR^3C(O)NR^3R^3$, —(SO)$R^3$, —(SO$_2$)$R^3$, —$NSO_2R^3$, —$SO_2NR^3R^3$.

Alternatively, $L^1$ and $L^2$ taken together may form a 4-8-membered, unsubstituted or a substituted saturated cyclic alkyl or heteroalkyl ring.

$R^3$, $R^{3'}$ are independently selected from the group consisting of H, unsubstituted or a substituted $C_1$-$C_6$-alkyl, unsubstituted or a substituted $C_1$-$C_6$-alkenyl, unsubstituted or a substituted aryl, unsubstituted or a substituted heteroaryl, unsubstituted or a substituted aryl-$C_1$-$C_6$-alkyl, unsubstituted or a substituted heteroaryl-$C_1$-$C_6$-alkyl.

$R^6$ is selected from the group consisting of hydrogen, unsubstituted or a substituted $C_1$-$C_6$-alkyl, $C_1$-$C_6$-alkoxy, OH, halogen, nitro, cyano, sulfonyl, oxo (=O), and n' is an integer from 0 to 4, preferably 1 or 2. In one embodiment $R^6$ is hydrogen.

In a further specific embodiment $R^6$ is H, $L^2$ is H, $L^1$ is —$NR^{3'}R^3$; where at least one of $R^{3'}$ and $R^3$ is not hydrogen, but a substituent selected from the group consisting of straight or branched $C_4$-$C_{18}$-alkyl, aryl-$C_1$-$C_{18}$-alkyl, heteroaryl-$C_2$-

$C_{18}$-alkyl, $C_1$-$C_{14}$-alkyl substituted with a $C_3$-$C_{12}$cycloalkyl or -bicyclo or -tricyloalkyl, and whereby said alkyl chain may contain 1-3 O or S atoms.

In a more specific embodiment $L^1$ is —$NHR^3$; where $R^3$ is a straight or branched $C_4$-$C_{12}$-alkyl, preferably a $C_6$-$C_{12}$-alkyl, optionally substituted with a cyclohexyl group or a benzyl group.

In a even more specific embodiment Y is a piperidine group

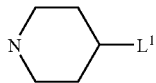

$L^1$ is —$NHR^3$; where $R^3$ is a straight or branched $C_4$-$C_{12}$-alkyl, preferably a $C_8$-$C_{12}$-alkyl, or a benzyl group.

Specific examples of compounds of formula I include the following:

4-chloro-N-[5-(piperazine-1-sulfonyl)-thiophen-2-yl-methyl]-benzamide

4-Chloro-N-{5-[4-(3-trifluoromethanesulfonyl-phenylamino)-piperidine-1-sulfonyl-thiophen-2-ylmethyl}-benzamide 4-chloro-N-({5-[(4-pyridin-2-ylpiperazin-1-yl)sulfonyl]thien-2-yl}methyl)benzamide 4-chloro-N-[(5-{[4-(4-fluorobenzoyl)piperidin-1-yl]sulfonyl}thien-2-yl)methyl]benzamide 4-chloro-N-{[5-({4-[4-(trifluoromethyl)phenyl]piperazin-1-yl}sulfonyl)thien-2-yl]methyl}benzamide 4-chloro-N-({5-[(4-{2-nitrophenyl}piperazin-1-yl)sulfonyl]thien-2-yl}methyl)benzamide 4-chloro-N-({5-[(4-{4-nitrophenyl}piperazin-1-yl)sulfonyl]thien-2-yl}methyl)benzamide 4-chloro-N-[(5-{[4-(2-furoyl)piperazin-1-yl]sulfonyl}thien-2-yl)methyl]benzamide 4-chloro-N-[(5-{[4-(4-hydroxyphenyl)piperazin-1-yl]sulfonyl}thien-2-yl)methyl]benzamide 4-chloro-N-[(5-{[4-(2-oxo-2-pyrrolidin-1-ylethyl)piperazin-1-yl]sulfonyl}thien-2-yl)methyl]benzamide 4-chloro-N-[(5-{[4-(2-morpholin-4-yl-2-oxyethyl)piperazin-1-yl]sulfonyl}thien-2-yl)methyl]benzamide 4-chloro-N-[(5-{[4-(pyridin-4-ylmethyl)piperazin-1-yl]sulfonyl}thien-2-yl)methyl]benzamide 4-chloro-N-[(5-{[4-(2-thien-2-ylethyl)piperazin-1-yl]sulfonyl}thien-2-yl)methyl]benzamide 4-chloro-N-[(5-{[4-(3,5-dimethoxyphenyl)piperazin-1-yl]sulfonyl}thien-2-yl)methyl]benzamide 4-chloro-N-[(5-{[4-(cyclohexylmethyl)piperazin-1-yl]sulfonyl}thien-2-yl)methyl]benzamide 4-chloro-N-[(5-{[4-(2-methoxyphenyl)piperazin-1-yl]sulfonyl}thien-2-yl)methyl]benzamide N-({5-[(4-benzylpiperazin-1-yl)sulfonyl]thien-2-yl}methyl)-4-chlorobenzamide 4-chloro-N-[(5-({[4-(2-phenylethyl)piperazin-1-yl]sulfonyl}thien-2-yl)methyl]benzamide 4-chloro-N-[(5-{[4-(4-fluorobenzyl)piperazin-1-yl]sulfonyl}thien-2-yl)methyl]benzamide 4-chloro-N-[(5-{[4-(2-cyanophenyl)piperazin-1-yl]sulfonyl}thien-2-yl)methyl]benzamide 4-chloro-N-{[5-({4-[4-chloro-3-(trifluoromethyl)phenyl]piperazin-1-yl}sulfonyl)thien-2-yl]methyl}benzamide 4-chloro-N-[(5-{[4-(3-piperidin-1-ylpropyl)piperazin-1-yl]sulfonyl}thien-2-yl)methyl]benzamide 4-chloro-N-({5-[(4-{4-chloro-2-nitrophenyl}piperazin-1-yl)sulfonyl]thien-2-yl}methyl)benzamide 4-chloro-N-[(5-{[4-(6-methylpyridin-2-yl)piperazin-1-yl]sulfonyl}thien-2-yl)methyl]benzamide 4-chloro-N-({5-[(4-hydroxy-4-phenylpiperidin-1-yl)sulfonyl]thien-2-yl}methyl)benzamide N-({5-[(4-benzoylpiperidin-1-yl)sulfonyl]thien-2-yl}methyl)-4-chlorobenzamide 4-chloro-N-[(5-{[4-(2-oxo-2,3-dihydro-1H-benzimidazol-1-yl)piperidin-1-yl]sulfonyl}thien-2-yl)methyl]benzamide N-({5-[(4-benzylpiperidin-1-yl)sulfonyl]thien-2-yl}methyl)-4-chlorobenzamide 4-chloro-N-({5-[(4-oxo-1-phenyl-1,3,8-triazaspiro[4,5]dec-8-yl)sulfonyl]thien-2-yl}methyl)benzamide 4-chloro-N-{[5-({4-[2-(methylanilino)-2-oxoethyl]piperazin-1-yl}sulfonyl)thien-2-yl]methyl}benzamide 4-chloro-N-{[5-({4-[hydroxy(diphenyl)methyl]piperidin-1-yl}sulfonyl)thien-2-yl]methyl}benzamide 4-chloro-N-[(5-{[4-(3-cyanopyrazin-2-yl)piperazin-1-yl]sulfonyl}thien-2-yl)methyl]benzamide 4-chloro-N-({5-[(4-{5-nitropyridin-2-yl}piperazin-1-yl)sulfonyl]thien-2-yl}methyl)benzamide 4-chloro-N-{[5-({4-[3-chloro-5-(trifluoromethyl)pyridin-2-yl]piperazin-1-yl}sulfonyl)thien-2-yl]methyl}benzamide 4-chloro-N-{[5-({4-[5-(trifluoromethyl)pyridin-2-yl]piperazin-1-yl}sulfonyl)thien-2-yl]methyl}benzamide 4-chloro-N-{[5-({4-[3-(trifluoromethyl)pyridin-2-yl]piperazin-1-yl}sulfonyl)thien-2-yl]methyl}benzamide 4-chloro-N-[(5-{[4-(2,4-difluorobenzoyl)piperidin-1-yl]sulfonyl}thien-2-yl)methyl]benzamide methyl 5-{4-[(5-{[(4-chlorobenzoyl)amino]methyl}thien-2-yl)sulfonyl]piperazin-1-yl}-7-(trifluoromethyl)thieno[3,2-b]pyridine-3-carboxylate ethyl 2-{4-[(5-{[(4-chlorobenzoyl)amino]methyl}thien-2-yl)sulfonyl]piperazin-1-yl}-5-cyano-6-methylnicotinate 4-chloro-N-{[5-{(4-[5-cyano-4,6-bis(dimethylamino)pyridin-2-yl]piperazin-1-yl}sulfonyl)thien-2-yl]methyl}benzamide 4-chloro-N-{[5-({4-[6-methyl-2-(trifluoromethyl)quinolin-4-yl]piperazin-1-yl}sulfonyl)thien-2-yl]methyl}benzamide tert-butyl 4-[(5-{[(4-chlorobenzoyl)amino]methyl}thien-2-yl)sulfonyl]piperazine-1-carboxylate 2-{4-[(5-{[(4-chlorobenzoyl)amino]methyl}thien-2-yl)sulfonyl]piperazin-1-yl}-8-ethyl-5-oxo-5,8-dihydropyrido[2,3-d]pyrimidine-6-carboxylic acid 7-{4-[(5-{[(4-chlorobenzoyl)amino]methyl}thien-2-yl)sulfonyl]piperazin-1-yl}-1-ethyl-6-fluoro-4-oxo-1,4-dihydro[1,8]naphthyridine-3-carboxylic acid 7-{4-[(5-{[(4-chlorobenzoyl)amino]methyl}thien-2-yl)sulfonyl]piperazin-1-yl}-1-ethyl-6-fluoro-4-oxo-1,4-dihydroquinoline-3-carboxylic acid 4-chloro-N-[(5-{[4-(2,3-dihydro-1,4-benzodioxin-2-ylcarbonyl)piperazin-1-yl]sulfonyl}thien-2-yl)methyl]benzamide 4-chloro-N-{[5-({4-[(2E)-3-phenylprop-2-enyl]piperazin-1-yl}sulfonyl)thien-2-yl]methyl}benzamide 4-chloro-N-[(5-{[4-(3-phenylpropyl)piperazin-1-yl]sulfonyl}thien-2-yl)methyl]benzamide 4-chloro-N-[(5-{[4-(3,4,5-trimethoxyphenyl)piperazin-1-yl]sulfonyl}thien-2-yl)methyl]benzamide N-[(5-{[4-(4-tert-butylbenzyl)piperazin-1-yl]sulfonyl}thien-2-yl)methyl]-4-chlorobenzamide 4-chloro-N-[(5-{[4-(4-fluorophenyl)piperazin-1-yl]sulfonyl}thien-2-yl)methyl]benzamide 4-chloro-N-[(5-{[4-(2-hydroxyphenyl)piperazin-1-yl]sulfonyl}thien-2-yl)methyl]benzamide 4-chloro-N-{[5-({4-[4-(trifluoromethyl)pyridin-2-yl]piperazin-1-yl}sulfonyl)thien-2-yl]methyl}benzamide
4-chloro-N-[(5-{[4-(5-cyanopyridin-2-yl)piperazin-1-yl]sulfonyl}thien-2-yl)methyl]benzamide
tert-butyl 1-[(5-{[(4-chlorobenzoyl)amino]methyl}thien-2-yl]sulfonyl]piperidin-4-ylcarbamate
4-chloro-N-({5-[(4-phenylpiperazin-1-yl)sulfonyl]thien-2-yl}methyl)benzamide
4-chloro-N-{[piperidin-1-ylsulfonyl)thien-2-yl]methyl}benzamide
4-chloro-N-[(5-{[4-(1-naphthyl)piperazin-1-yl]sulfonyl}thien-2-yl)methyl]benzamide
4-chloro-N-[(5-{[4-(3,4-dichlorophenyl)piperazin-1-yl]sulfonyl}thien-2-yl)methyl]benzamide
4-chloro-N-{[5-({4-[3-(trifluoromethyl)phenyl]piperazin-1-yl}sulfonyl)thien-2-yl]methyl}benzamide
4-chloro-N-{[5-({3-hydroxy-4-[3-(trifluoromethyl)phenyl]piperidin-1-yl}sulfonyl)thien-2-yl]methyl}benzamide
4-chloro-N-[(5-{[4-(2-methylphenyl)piperazin-1-yl]sulfonyl}thien-2-yl)methyl]benzamide
N-[(5-{[(1R,4R)-5-benzyl-2,5-diazabicyclo[2.2.1]hept-2-yl]sulfonyl}thien-2-yl)methyl]-4-chlorobenzamide
N-[(5-{[4-(benzyloxy)piperidin-1-yl]sulfonyl}thien-2-yl)methyl]-4-chlorobenzamide
4-chloro-N-[(5-{[4-(2-chlorodibenzo[b,f][1,4]oxazepin-11-yl)piperazin-1-yl]sulfonyl}thien-2-yl)methyl]benzamide
N-(4-chlorophenyl)-2-(5-{[4-(2-oxo-2,3-dihydro-1H-benzimidazol-1-yl)piperidin-1-yl]sulfonyl}thien-2-yl)acetamide
4-chloro-N-({5-[(4-hydroxypiperidin-1-yl)sulfonyl]thien-2-yl}methyl)benzamide
N-[(5-{[4-(4-acetylphenyl)piperazin-1-yl]sulfonyl}thien-2-yl)methyl]-4-chlorobenzamide
4-chloro-N-[(5-{[4-(3,5-dichloropyridin-4-yl)piperazin-1-yl]sulfonyl}thien-2-yl)methyl]benzamide
4-chloro-N-[(5-{([4-(3-methoxyphenyl)piperazin-1-yl]sulfonyl}thien-2-yl)methyl]benzamide
N-({5-[(4-benzyl-4-hydroxypiperidin-1-yl)sulfonyl]thien-2-yl}methyl)-4-chlorobenzamide
N-{[5-({4-[(2-tert-butyl-1H-indol-5-yl)amino]piperidin-1-yl}sulfonyl)thien-2-yl]methyl}-4-chlorobenzamide
4-chloro-N-{[5-({4-[(phenylacetyl)amino]piperidin-1-yl}sulfonyl)thien-2-yl]methyl}benzamide
4-chloro-N-[(5-{[4-(tetrahydrofuran-2-ylcarbonyl)piperazin-1-yl]sulfonyl}thien-2-yl)methyl]benzamide
4-chloro-N-[(5-{[4-(6-chloropyridin-2-yl)piperazin-1-yl]sulfonyl}thien-2-yl)methyl]benzamide
4-chloro-N-[(5-{[4-(4-chlorophenyl)piperazin-1-yl]sulfonyl}thien-2-yl)methyl]benzamide
N-[(5-{[4-(2H-1,2,3-benzotriazol-2-yl)piperidin-1-yl]sulfonyl}thien-2-yl)methyl]-4-chlorobenzamide
4-chloro-N-[(5-{[4-(4-chlorobenzoyl)piperidin-1-yl]sulfonyl}thien-2-yl)methyl]benzamide
4-chloro-N-({5-[(4-phenoxypiperidin-1-yl)sulfonyl]thien-2-yl}methyl)benzamide
N-{[5-({4-[benzyl(methyl)amino]piperidin-1-yl}sulfonyl)thien-2-yl]methyl}-4-chlorobenzamide
4-chloro-N-{[5-({4-[3-(2,4-dichlorophenyl)-1H-pyrazol-5-yl]piperidin-1-yl}sulfonyl)thien-2-yl]methyl}benzamide
4-chloro-N-[(5-{[4-(5-thien-2-yl-1H-pyrazol-3-yl)piperidin-1-yl]sulfonyl}thien-2-yl)methyl]benzamide
4-chloro-N-[(5-{[4-(2,3,4,5,6-pentamethylbenzoyl)piperidin-1-yl]sulfonyl}thien-2-yl)methyl]benzamide
4-chloro-N-[(5-{[4-(phenylacetyl)-1,4-diazepan-1-yl]sulfonyl}thien-2-yl)methyl]benzamide
4-chloro-N-{[5-({4-[5-(4-methoxyphenyl)-1H-pyrazol-3-yl]piperidin-1-yl}sulfonyl)thien-2-yl]methyl}benzamide
N-({5-[(4-anilinopiperidin-1-yl)sulfonyl]thien-2-yl}methyl)-4-chlorobenzamide
4-chloro-N-[(5-{[4-(3-phenyl-1,2,4-thiadiazol-5-yl)piperazin-1-yl]sulfonyl}thien-2-yl)methyl]benzamide
4-chloro-N-[(5-{[4-(2-phenylethyl)piperazin-1-yl]sulfonyl}thien-2-yl)methyl]benzamide
4-chloro-N-({5-[(4-heptylpiperazin-1-yl)sulfonyl]thien-2-yl}methyl)benzamide
4-chloro-N-({5-[(4-octylpiperazin-1-yl)sulfonyl]thien-2-yl}methyl)benzamide
N-[(5-{[4-(1H-1,2,3-benzotriazol-1-yl)piperidin-1-yl]sulfonyl}thien-2-yl)methyl]-4-chlorobenzamide
2-(5-{[4-(1H-1,2,3-benzotriazol-1-yl)piperidin-1-yl]sulfonyl}thien-2-yl)-N-(4-chlorophenyl)acetamide
2-{1-[(5-{[(4-chlorobenzoyl)amino]methyl}thien-2-yl)sulfonyl]piperidin-4-yl}-2H-1,2,3-benzotriazole-5-carboxylic acid
4-chloro-N-[(5-{[4-(5-chloro-1H-1,2,3-benzotriazol-1-yl)piperidin-1-yl]sulfonyl}thien-2-yl)methyl]benzamide
methyl 1-{1-[(5-{[(4-chlorobenzoyl)amino]methyl}thien-2-yl)sulfonyl]piperidin-4-yl}-1H-1,2,3-benzotriazole-5-carboxylate
methyl 1-{1-[(5-{[(4-chlorobenzoyl)amino]methyl}thien-2-yl)sulfonyl]piperidin-4-yl}-1H-1,2,3-benzotriazole-6-carboxylate
methyl 2-{1-[(5-{[(4-chlorobenzoyl)amino]methyl}thien-2-yl)sulfonyl]piperidin-4-yl}-2H-1,2,3-benzotriazole-5-carboxylate
4-chloro-N-[(5-{[4-(6-chloro-1H-1,2,3-benzotriazol-1-yl)piperidin-1-yl]sulfonyl}thien-2-yl)methyl]benzamide
4-chloro-N-{[5-({4-[5-(trifluoromethyl)-1H-1,2,3-benzotriazol-1-yl]piperidin-1-yl}sulfonyl)thien-2-yl]methyl}benzamide
N-[(5-{[4-(7-aza-1H-benzimidazol-1-yl)piperidin-1-yl]sulfonyl}thien-2-yl)methyl]-4-chlorobenzamide
1-{1-[(5-{[(4-chlorobenzoyl)amino]methyl}thien-2-yl)sulfonyl]piperidin-4-yl}-1H-1,2,3-benzotriazole-5-carboxylic acid
1-{1-[(5-{[(4-chlorobenzoyl)amino]methyl}thien-2-yl)sulfonyl]piperidin-4-yl}-1H-1,2,3-benzotriazole-6-carboxylic acid
N-[(5-{[4-(2-amino-9H-purin-9-yl)piperidin-1-yl]sulfonyl}thien-2-yl)methyl]-4-chlorobenzamide
4-chloro-N-[(5-{[4-(9H-purin-9-yl)piperidin-1-yl]sulfonyl}thien-2-yl)methyl]benzamide
N-[(5-{[4-(6-amino-9H-purin-9-yl)piperidin-1-yl]sulfonyl}thien-2-yl)methyl]-4-chlorobenzamide
4-chloro-N-({5-[(4-{6-nitro-1H-benzimidazol-1-yl}piperidin-1-yl)sulfonyl]thien-2-yl}methyl)benzamide
4-chloro-N-({5-[(4-{5-nitro-1H-benzimidazol-1-yl}piperidin-1-yl)sulfonyl]thien-2-yl}methyl)benzamide
4-chloro-N-[(5-{[4-(2H-1,2,3-triazol-2-yl)piperidin-1-yl]sulfonyl}thien-2-yl)methyl]benzamide
N-[(5-{[4-(1H-benzimidazol-1-yl)piperidin-1-yl]sulfonyl}thien-2-yl)methyl]-4-chlorobenzamide
4-chloro-N-{[5-({4-[3-propylanilino]piperidin-1-yl}sulfonyl)thien-2-yl]methyl}benzamide
4-chloro-N-{[5-({4-[3-(trifluoromethyl)anilino]piperidin-1-yl}sulfonyl)thien-2-yl]methyl}benzamide
4-chloro-N-{[5-({4-[3-(dimethylamino)anilino]piperidin-1-yl}sulfonyl)thien-2-yl]methyl}benzamide
methyl 3-([1-[(5-{[(4-chlorobenzoyl)amino]-methyl}thien-2-yl)sulfonyl-piperidin-4-yl]amino)-benzoate
4-chloro-N-{[5-({4-[3-(methylsulfanyl)anilino]piperidin-1-yl}sulfonyl)thien-2-yl]methyl}benzamide
4-chloro-N-({5-[(4-{3-nitroanilino}piperidin-1-yl)sulfonyl]thien-2-yl}methyl)benzamide 4-chloro-N-[(5-{[4-(2-methoxyanilino)piperidin-1-yl]sulfonyl}thien-2-yl)methyl]benzamide
3-({1-[(5-{[(4-chlorobenzoyl)amino]methyl}thien-2-yl)sulfonyl]piperidin-4-yl}amino)benzamide
4-chloro-N-{[5-({4-[2-(trifluoromethyl)anilino]piperidin-1-yl}sulfonyl)thien-2-yl]methyl}benzamide
4-chloro-N-({5-[(4-{2-nitro-4-[(trifluoromethyl)sulfonyl]anilino}piperidin-1-yl)sulfonyl]thien-2-yl}methyl)benzamide
4-chloro-N-[(5-{[4-(4-chloroanilino)piperidin-1-yl]sulfonyl}thien-2-yl)methyl]benzamide
4-chloro-N-{[5-({4-[4-(trifluoromethyl)anilino]piperidin-1-yl}sulfonyl)thien-2-yl]methyl}benzamide
4-chloro-N-({5-[(4-{4-[(trifluoromethyl)sulfonyl]anilino}piperidin-1-yl)sulfonyl]thien-2-yl}methyl)benzamide
4-chloro-N-({5-[(4-{2-nitroanilino}piperidin-1-yl)sulfonyl]thien-2-yl}methyl)benzamide
N-{[5-({4-[4-(aminocarbonyl)anilino]piperidin-1-yl}sulfonyl)thien-2-yl]methyl}-4-chlorobenzamide
4-chloro-N-{[5-({4-[4-(1,3-dithiolan-2-yl)anilino]piperidin-1-yl}sulfonyl)thien-2-yl]methyl}benzamide
N-[(5-{[4-(3-chloroanilino)piperidin-1-yl]sulfonyl}thien-2-yl)methyl]-3-nitrobenzamide
4-chloro-N-[(5-{[4-(3-chloroanilino)piperidin-1-yl]sulfonyl}thien-2-yl)methyl]benzamide
4-chloro-N-[(5-{[4-(3-methoxyanilino)piperidin-1-yl]sulfonyl}thien-2-yl)methyl]benzamide
4-chloro-N-{[5-({4-[3-(methylsulfonyl)anilino]piperidin-1-yl}sulfonyl)thien-2-yl]methyl}benzamide
N-({5-[(4-{3-[amino(imino)methyl]anilino}piperidin-1-yl)sulfonyl]thien-2-yl}methyl)-4-chlorobenzamide
4-chloro-N-({5-[(4-{3-[(2-hydroxyethyl)sulfonyl]anilino}piperidin-1-yl)sulfonyl]thien-2-yl}methyl)benzamide
N-[(5-{[4-(2-aminoanilino)piperidin-1-yl]sulfonyl}thien-2-yl)methyl]-4-chlorobenzamide
4-chloro-N-[(5-{[4-(2-hydroxyanilino)piperidin-1-yl]sulfonyl}thien-2-yl)methyl]benzamide
4-chloro-N-[(5-{[4-(4-hydroxyanilino)piperidin-1-yl]sulfonyl}thien-2-yl)methyl]benzamide
4-chloro-N-({5-[(4-{3-[(trifluoromethyl)sulfanyl]anilino}piperidin-1-yl)sulfonyl]thien-2-yl}methyl)benzamide
4-chloro-N-[(5-{[4-(3-toluidino)piperidin-1-yl]sulfonyl}thien-2-yl)methyl]benzamide
4-chloro-N-({5-[(4-{[3-chloro-5-(trifluoromethyl)pyridin-2-yl]amino}piperidin-1-yl)sulfonyl]thien-2-yl}methyl)benzamide
4-chloro-N-{[5-({4-[3-(1,3-oxazol-5-yl)anilino]piperidin-1-yl}sulfonyl)thien-2-yl]methyl}benzamide
N-[(5-{[4-(3-tert-butylanilino)piperidin-1-yl]sulfonyl}thien-2-yl)methyl]-4-chlorobenzamide
4-chloro-N-[(5-{[4-(2-propylanilino)piperidin-1-yl]sulfonyl}thien-2-yl)methyl]benzamide
4-chloro-N-{[5-({4-[(2,2-dioxido-1,3-dihydro-2-benzothien-5-yl)amino]piperidin-1-yl}sulfonyl)thien-2-yl]methyl}benzamide
4-chloro-N-[(5-{[4-(2,3-dihydro-1H-inden-5-ylamino)piperidin-1-yl]sulfonyl}thien-2-yl)methyl]benzamide
4-chloro-N-[(5-{[4-(4-propylanilino)piperidin-1-yl]sulfonyl}thien-2-yl)methyl]benzamide
4-chloro-N-[(5-{[4-({3-nitropyridin-2-yl}amino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-4-chlorobenzamide
N-[(5-{[4-([1,1'-biphenyl]-3-ylamino)piperidin-1-yl]sulfonyl}thien-2-yl)methyl]-4-chlorobenzamide
N-[(5-{[4-(3-benzylanilino)piperidin-1-yl]sulfonyl}thien-2-yl)methyl]-4-chlorobenzamide
4-chloro-N-[(5-{[4-(pyrimidin-2-ylamino)piperidin-1-yl]sulfonyl}thien-2-yl)methyl]benzamide
4-chloro-N-{[5-({4-[4-(morpholin-4-ylsulfonyl)anilino]piperidin-1-yl}sulfonyl)thien-2-yl]methyl}benzamide
4-chloro-N-({5-[(4-{[4-(trifluoromethyl)pyrimidin-2-yl]amino}piperidin-1-yl)sulfonyl]thien-2-yl}methyl)benzamide
4-chloro-N-[(5-{[4-(3-cyclohexyl-4-hydroxyanilino)piperidin-1-yl]sulfonyl}thien-2-yl)methyl]benzamide
N-({5-[(4-{3-[(butylamino)sulfonyl]anilino}piperidin-1-yl)sulfonyl]thien-2-yl}methyl)-4-chlorobenzamide
4-chloro-N-[(5-{[4-(3-ethylanilino)piperidin-1-yl]sulfonyl}thien-2-yl)methyl]benzamide
4-chloro-N-[(5-{[4-(5,6,7,8-tetrahydronaphthalen-1-ylamino)piperidin-1-yl]sulfonyl}thien-2-yl)methyl]benzamide
N-{[5-({4-[3-(aminosulfonyl)anilino]piperidin-1-yl}sulfonyl)thien-2-yl]methyl}-4-chlorobenzamide
4-chloro-N-[(5-{[4-(quinolin-5-ylamino)piperidin-1-yl]sulfonyl}thien-2-yl)methyl]benzamide
4-chloro-N-[(5-{[4-(quinolin-8-ylamino)piperidin-1-yl]sulfonyl}thien-2-yl)methyl]benzamide
4-Chloro-N-[(5-{[4-(3-propylphenoxy)piperidin-1-yl]sulfonyl}thien-2-yl)methyl]benzamide
4-chloro-N-{[5-({4-[(2E)-3-phenylprop-2-enoyl]piperazin-1-yl}sulfonyl)thien-2-yl]methyl}benzamide
4-chloro-N-({5-[(4-{4-nitrobenzoyl}piperazin-1-yl)sulfonyl]thien-2-yl}methyl)benzamide
N-({5-[(4-benzoylpiperazin-1-yl)sulfonyl]thien-2-yl}methyl)-4-chlorobenzamide
4-chloro-N-{[5-({4-[4-(trifluoromethyl)benzoyl]piperazin-1-yl}sulfonyl)thien-2-yl]methyl}benzamide
4-chloro-N-{[5-({4-[4-(dimethylamino)benzoyl]piperazin-1-yl}sulfonyl)thien-2-yl]methyl}benzamide
4-chloro-N-[(5-{[4-(2-fluorobenzoyl)piperazin-1-yl]sulfonyl}thien-2-yl)methyl]benzamide
4-chloro-N-[(5-{[4-(2,6-difluorobenzoyl)piperazin-1-yl]sulfonyl}thien-2-yl)methyl]benzamide
4-chloro-N-[(5-{[4-(3-fluorobenzoyl)piperazin-1-yl]sulfonyl}thien-2-yl)methyl]benzamide
4-chloro-N-[(5-{[4-(2-naphthoyl)piperazin-1-yl]sulfonyl}thien-2-yl)methyl]benzamide
4-chloro-N-[(5-{[4-(1-naphthoyl)piperazin-1-yl]sulfonyl}thien-2-yl)methyl]benzamide
4-chloro-N-({5-[(4-{2-nitrobenzoyl}piperazin-1-yl)sulfonyl]thien-2-yl}methyl)benzamide
4-chloro-N-[(5-{[4-(pyridin-3-ylcarbonyl)piperazin-1-yl]sulfonyl}thien-2-yl)methyl]benzamide
N-[(5-{[4-(2,1,3-benzoxadiazol-5-ylcarbonyl)piperazin-1-yl]sulfonyl}thien-2-yl)methyl]-4-chlorobenzamide
4-chloro-N-[(5-{[4-(2,4-difluorobenzoyl)piperazin-1-yl]sulfonyl}thien-2-yl)methyl]benzamide
4-chloro-N-[(5-({[4-(2,4,6-trifluorobenzoyl)piperazin-1-yl]sulfonyl}thien-2-yl)methyl]benzamide
4-chloro-N-[(5-{[4-(2,6-dichlorobenzoyl)piperazin-1-yl]sulfonyl}thien-2-yl)methyl]benzamide
4-chloro-N-({5-[(4-heptanoylpiperazin-1-yl)sulfonyl]thien-2-yl}methyl)benzamide
4-chloro-N-[(5-{[4-(quinolin-8-ylsulfonyl)piperazin-1-yl]sulfonyl}thien-2-yl)methyl]benzamide
4-nitro-N-({5-[(4-{3-[(trifluoromethyl)sulfonyl]anilino}piperidin-1-yl)sulfonyl]thien-2-yl}methyl)benzamide N-[(5-{[4-(1H-1,2,3-benzotriazol-1-yl)piperidin-1-yl]sulfonyl}thien-2-yl)methyl]-3-nitrobenzamide
4-nitro-N-({5-[(4-{3-[(trifluoromethyl)sulfonyl]anilino}piperidin-1-yl)sulfonyl]thien-2-yl}methyl)benzamide
N-[(5-{[4-(2,4-difluorobenzoyl)piperidin-1-yl]sulfonyl}thien-2-yl)methyl]-4-nitrobenzamide
N-[(5-{[4-(1H-1,2,3-benzotriazol-1-yl)piperidin-1-yl]sulfonyl}thien-2-yl)methyl]-4-nitrobenzamide
N-[(5-{[4-(1H-1,2,3-benzotriazol-1-yl)piperidin-1-yl]sulfonyl}thien-2-yl)methyl]-3-nitrobenzamide
4-nitro-N-({5-[(4-{3-[(trifluoromethyl)sulfonyl]anilino}piperidin-1-yl)sulfonyl]thien-2-yl}methyl)benzamide
N-[(5-{[4-(2,4-difluorobenzoyl)piperidin-1-yl]sulfonyl}thien-2-yl)methyl]-4-nitrobenzamide
N-[(5-{[4-(1H-1,2,3-benzotriazol-1-yl)piperidin-1-yl]sulfonyl}thien-2-yl)methyl]-4-nitrobenzamide
3-nitro-N-[(5-{[4-(3-methoxyanilino)piperidin-1-yl]sulfonyl}thien-2-yl)methyl]benzamide
3-nitro-N-{[5-({4-[3-(trifluoromethyl)anilino]piperidin-1-yl}sulfonyl)thien-2-yl]methyl}benzamide
N-{[5-({4-[3-(dimethylamino)anilino]piperidin-1-yl}sulfonyl)thien-2-yl]methyl}-3-nitrobenzamide
3-nitro-N-{[5-({4-[3-(methylsulfonyl)anilino]piperidin-1-yl}sulfonyl)thien-2-yl]methyl}benzamide
3-nitro-N-{[5-({4-[3-(methylsulfanyl)anilino]piperidin-1-yl}sulfonyl)thien-2-yl]methyl}benzamide
N-{[5-({4-[3-(aminosulfonyl)anilino]piperidin-1-yl}sulfonyl)thien-2-yl]methyl}-3-nitrobenzamide
methyl 3-{[1-({5-[({3-nitrobenzoyl}amino)methyl]-thien-2-yl}sulfonyl)-piperidin-4-yl]amino}benzoate
N-{[5-({4-[3-(aminocarbonyl)anilino]piperidin-1-yl}sulfonyl)thien-2-yl]methyl}-3-nitrobenzamide
3-nitro-N-({5-[(4-{3-nitroanilino}piperidin-1-yl)sulfonyl]thien-2-yl}methyl)benzamide
3-nitro-N-[(5-{[4-(2-methoxyanilino)piperidin-1-yl]sulfonyl}thien-2-yl)methyl]benzamide
3-nitro-N-{[5-({4-[2-(trifluoromethyl)anilino]piperidin-1-yl}sulfonyl)thien-2-yl]methyl}benzamide
3-nitro-N-({5-[(4-{2-nitroanilino}piperidin-1-yl)sulfonyl]thien-2-yl}methyl)benzamide
N-[(5-{[4-(4-chloroanilino)piperidin-1-yl]sulfonyl}thien-2-yl)methyl]-3-nitrobenzamide
3-nitro-N-{[5-({4-[4-(trifluoromethyl)anilino]piperidin-1-yl}sulfonyl)thien-2-yl]methyl}benzamide
3-nitro-N-({5-[(4-{4-[(trifluoromethyl)sulfonyl]anilino}piperidin-1-yl)sulfonyl]thien-2-yl}methyl)benzamide
N-{[5-({4-[4-(aminocarbonyl)anilino]piperidin-1-yl}sulfonyl)thien-2-yl]methyl}-3-nitrobenzamide
N-[(5-{[4-(3-propylanilino)piperidin-1-yl]sulfonyl}thien-2-yl)methyl]-3-nitrobenzamide
N-[(5-{[4-(3-chloroanilino)piperidin-1-yl]sulfonyl}thien-2-yl)methyl]-4-nitrobenzamide
4-nitro-N-[(5-{[4-(3-methoxyanilino)piperidin-1-yl]sulfonyl}thien-2-yl)methyl]benzamide
4-nitro-N-{[5-({4-[3-(trifluoromethyl)anilino]piperidin-1-yl}sulfonyl)thien-2-yl]methyl}benzamide
N-{[5-({4-[3-(dimethylamino)anilino]piperidin-1-yl}sulfonyl)thien-2-yl]methyl}-4-nitrobenzamide
4-nitro-N-[(5-{[4-(3-propylanilino)piperidin-1-yl]sulfonyl}thien-2-yl)methyl]benzamide
4-nitro-N-{[5-({4-[3-(methylsulfonyl)anilino]piperidin-1-yl}sulfonyl)thien-2-yl]methyl}benzamide
4-nitro-N-{[5-({4-[3-(methylsulfanyl)anilino]piperidin-1-yl}sulfonyl)thien-2-yl]methyl}benzamide
N-{[5-({4-[3-(aminosulfonyl)anilino]piperidin-1-yl}sulfonyl)thien-2-yl]methyl}-4-nitrobenzamide
3-{[1-({5-[({4-nitrobenzoyl}amino)methyl]thien-2-yl}sulfonyl)piperidin-4-yl]amino}benzoate
3-{[1-({5-[({4-nitrobenzoyl}amino)methyl]thien-2-yl}sulfonyl)piperidin-4-yl]amino}benzoate
4-nitro-N-({5-[(4-{3-nitroanilino}piperidin-1-yl)sulfonyl]thien-2-yl}methyl)benzamide
4-nitro-N-[(5-{[4-(2-methoxyanilino)piperidin-1-yl]sulfonyl}thien-2-yl)methyl]benzamide
4-nitro-N-{[5-({4-[2-(trifluoromethyl)anilino]piperidin-1-yl}sulfonyl)thien-2-yl]methyl}benzamide
4-nitro-N-({5-[(4-{2-nitroanilino}piperidin-1-yl)sulfonyl]thien-2-yl}methyl)benzamide
N-[(5-{[4-(4-chloroanilino)piperidin-1-yl]sulfonyl}thien-2-yl)methyl]-4-nitrobenzamide
4-nitro-N-{[5-({4-[4-(trifluoromethyl)anilino]piperidin-1-yl}sulfonyl)thien-2-yl]methyl}benzamide
4-nitro-N-({5-[(4-{4-[(trifluoromethyl)sulfonyl]anilino}piperidin-1-yl)sulfonyl]thien-2-yl}methyl)benzamide
N-{[5-({4-[4-(aminocarbonyl)anilino]piperidin-1-yl}sulfonyl)thien-2-yl]methyl}-4-nitrobenzamide
N-{[5-({4-[4-(1,3-dithiolan-2-yl)anilino]piperidin-1-yl}sulfonyl)thien-2-yl]methyl}-4-nitrobenzamide
N-({5-[(4-{3-[amino(imino)methyl]anilino}piperidin-1-yl)sulfonyl]thien-2-yl}methyl)-3-nitrobenzamide
N-({5-[(4-{3-[(2-hydroxyethyl)sulfonyl]anilino}piperidin-1-yl)sulfonyl]thien-2-yl}methyl)-3-nitrobenzamide
N-({5-[(4-anilinopiperidin-1-yl)sulfonyl]thien-2-yl}methyl)-3-nitrobenzamide
N-({5-[(4-{3-[(2-hydroxyethyl)sulfonyl]anilino}piperidin-1-yl)sulfonyl]thien-2-yl}methyl)-4-nitrobenzamide
N-({5-[(4-anilinopiperidin-1-yl)sulfonyl]thien-2-yl}methyl)-4-nitrobenzamide
N-({5-[(4-{3-[amino(imino)methyl]anilino}piperidin-1-yl)sulfonyl]thien-2-yl}methyl)-4-nitrobenzamide
3-nitro-N-({5-[(4-{3-[(trifluoromethyl)sulfanyl]anilino}piperidin-1-yl)sulfonyl]thien-2-yl}methyl)benzamide
4-nitro-N-({5-[(4-{3-[(trifluoromethyl)sulfanyl]anilino}piperidin-1-yl)sulfonyl]thien-2-yl}methyl)benzamide
3-nitro-N-[(5-{[4-({3-nitropyridin-2-yl}amino)piperidin-1-yl]sulfonyl}thien-2-yl)methyl]benzamide
N-{[5-({4-[(2,2-dioxido-1,3-dihydro-2-benzothien-5-yl)amino]piperidin-1-yl}sulfonyl)thien-2-yl]methyl}-3-nitrobenzamide
N-[(5-{[4-(2,3-dihydro-1H-inden-5-ylamino)piperidin-1-yl]sulfonyl}thien-2-yl)methyl]-3-nitrobenzamide
3-nitro-N-[(5-{[4-(2-propylanilino)piperidin-1-yl]sulfonyl}thien-2-yl)methyl]benzamide
3-nitro-N-[(5-{[4-(4-propylanilino)piperidin-1-yl]sulfonyl}thien-2-yl)methyl]benzamide
N-[(5-{[4-(3-tert-butylanilino)piperidin-1-yl]sulfonyl}thien-2-yl)methyl]-3-nitrobenzamide
3-nitro-N-{[5-({4-[3-(1,3-oxazol-5-yl)amino]piperidin-1-yl}sulfonyl)thien-2-yl]methyl}benzamide
3-nitro-N-[(5-{[4-(2-phenylethyl)piperidin-1-yl]sulfonyl}thien-2-yl)methyl]benzamide
N-({5-[(4-{[3-chloro-5-(trifluoromethyl)pyridin-2-yl]amino}piperidin-1-yl)sulfonyl]thien-2-yl}methyl)-3-nitrobenzamide
N-[(5-{[4-([1,1'-biphenyl]-3-ylamino)piperidin-1-yl]sulfonyl}thien-2-yl)methyl]-3-nitrobenzamide
N-[(5-{[4-(3-benzylanilino)piperidin-1-yl]sulfonyl}thien-2-yl)methyl]-3-nitrobenzamide 3-nitro-N-{[5-({4-(3-(morpholin-4-ylsulfonyl)anilino]piperidin-1-yl}sulfonyl)thien-2-yl]methyl}benzamide
3-nitro-N-[(5-{[4-(3-propylphenoxy)piperidin-1-yl]sulfonyl}thien-2-yl)methyl]benzamide
4-nitro-N-[(5-{[4-(pyrimidin-2-ylamino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}4-nitrobenzamide
4-nitro-N-[(5-{[4-({3-nitropyridin-2-yl}amino)piperidin-1-yl]sulfonyl}thien-2-yl)methyl]benzamide
N-[(5-{[4-(2,3-dihydro-1H-inden-5-ylamino)piperidin-1-yl]sulfonyl}thien-2-yl)methyl]-4-nitrobenzamide
4-nitro-N-[(5-{[4-(2-propylanilino)piperidin-1-yl]sulfonyl}thien-2-yl)methyl]benzamide
4-nitro-N-[(5-{[4-(4-propylanilino)piperidin-1-yl]sulfonyl}thien-2-yl)methyl]benzamide
N-[(5-{[4-(3-tert-butylanilino)piperidin-1-yl]sulfonyl}thien-2-yl)methyl]-4-nitrobenzamide
4-nitro-N-{[5-({4-[3-(1,3-oxazol-5-yl)anilino]piperidin-1-yl}sulfonyl)thien-2-yl]methyl}benzamide
4-nitro-N-[(5-{[4-(2-phenylethyl)piperidin-1-yl]sulfonyl}thien-2-yl)methyl]benzamide
N-({5-[(4-{[3-chloro-5-(trifluoromethyl)pyridin-2-yl]amino}piperidin-1-yl)sulfonyl]thien-2-yl}methyl)-4-nitrobenzamide
N-[(5-{[4-([1,1'-biphenyl]-3-ylamino)piperidin-1-yl]sulfonyl}thien-2-yl)methyl]-4-nitrobenzamide
N-[(5-{[4-(3-benzylanilino)piperidin-1-yl]sulfonyl}thien-2-yl)methyl]-4-nitrobenzamide
4-nitro-N-{[5-({4-[3-(morpholin-4-ylsulfonyl)anilino]piperidin-1-yl}sulfonyl)thien-2-yl]methyl}benzamide
N-[(5-{[4-(2-aminoanilino)piperidin-1-yl]sulfonyl}thien-2-yl)methyl]-3-nitrobenzamide
3-nitro-N-[(5-{[4-(pyrimidin-2-ylamino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-3-nitrobenzamide
N-({5-[(4-{2-nitro-4-[(trifluoromethyl)sulfonyl]anilino}piperidin-1-yl)sulfonyl]thien-2-yl}methyl)-3-methoxybenzamide
3-nitro-N-[(5-{[4-(3-phenylpropyl)piperazin-1-yl]sulfonyl}thien-2-yl)methyl]benzamide
3-nitro-N-({5-{[(4-{[4-(trifluoromethyl)pyrimidin-2-yl]amino}piperidin-1-yl)sulfonyl]thien-2-yl}methyl)benzamide
N-[(5-{[4-(3-cyclohexyl-4-hydroxyanilino)piperidin-1-yl]sulfonyl}thien-2-yl)methyl]-3-nitrobenzamide
N-({5-[(4-{3-[(butylamino)sulfonyl]anilino}piperidin-1-yl)sulfonyl]thien-2-yl}methyl)-3-nitrobenzamide
N-[(5-{[4-(3-ethylanilino)piperidin-1-yl]sulfonyl}thien-2-yl)methyl]-3-nitrobenzamide
3-nitro-N-[(5-{[4-(5,6,7,8-tetrahydronaphthalen-1-ylamino)piperidin-1-yl]sulfonyl}thien-2-yl)methyl]benzamide
4-nitro-N-[(5-{[4-(3-propylphenoxy)piperidin-1-yl]sulfonyl}thien-2-yl)methyl]benzamide
N-[(5-{[4-(2,4-difluorobenzoyl)piperidin-1-yl]sulfonyl}thien-2-yl)methyl]-3-nitrobenzamide
N-[(5-{[4-(2,4-difluorobenzoyl)piperidin-1-yl]sulfonyl}thien-2-yl)methyl]-3-methoxybenzamide
2-Hydroxy-N-({5-[(4-{3-[(trifluoromethyl)sulfonyl]anilino}piperidin-1-yl)sulfonyl]thien-2-yl}methyl)benzamide
N-[(5-{[4-(1H-1,2,3-benzotriazol-1-yl)piperidin-1-yl]sulfonyl}thien-2-yl)methyl]-3-methoxybenzamide
N-[(5-{[4-(1H-1,2,3-benzotriazol-1-yl)piperidin-1-yl]sulfonyl}thien-2-yl)methyl]-2-hydroxybenzamide
N-{[5-({4-[4-(1,3-dithiolan-2-yl)anilino]piperidin-1-yl}sulfonyl)thien-2-yl]methyl}-3-nitrobenzamide
3-methoxy-N-[(5-{[4-(3-methoxyanilino)piperidin-1-yl]sulfonyl}thien-2-yl)methyl]benzamide
3-methoxy-N-{[5-({4-[3-(trifluoromethyl)anilino]piperidin-1-yl}sulfonyl)thien-2-yl]methyl}benzamide
N-{[5-({4-[3-(dimethylamino)anilino]piperidin-1-yl}sulfonyl)thien-2-yl]methyl}-3-methoxybenzamide
3-methoxy-N-[(5-{[4-(3-propylanilino)piperidin-1-yl]sulfonyl}thien-2-yl)methyl]benzamide
3-methoxy-N-{[5-({4-[3-(methylsulfonyl)anilino]piperidin-1-yl}sulfonyl)thien-2-yl]methyl}benzamide
3-methoxy-N-{[5-({4-[3-(methylsulfanyl)anilino]piperidin-1-yl}sulfonyl)thien-2-yl]methyl}benzamide
N-{[5-({4-[3-(aminosulfonyl)anilino]piperidin-1-yl}sulfonyl)thien-2-yl]methyl}-3-methoxybenzamide
methyl 3-({1-[(5-{[(3-methoxybenzoyl)amino]methyl}thien-2-yl)sulfonyl]-piperidin-4-yl}amino)-benzoate
N-{[5-({4-[3-(aminocarbonyl)anilino]piperidin-1-yl}sulfonyl)thien-2-yl]methyl}-3-methoxybenzamide
3-methoxy-N-[(5-{[4-(2-methoxyanilino)piperidin-1-yl]sulfonyl}thien-2-yl)methyl]benzamide
N-({5-[(4-{3-nitroanilino}piperidin-1-yl)sulfonyl]thien-2-yl}methyl)-3-methoxybenzamide
3-methoxy-N-{[5-({4-[2-(trifluoromethyl)anilino]piperidin-1-yl}sulfonyl)thien-2-yl]methyl}benzamide
N-({5-[(4-{2-nitroanilino}piperidin-1-yl)sulfonyl]thien-2-yl}methyl)-3-methoxybenzamide
N-{[5-({4-[4-(aminocarbonyl)anilino]piperidin-1-yl}sulfonyl)thien-2-yl]methyl}-3-methoxybenzamide
N-{[5-({4-[4-(1,3-dithiolan-2-yl)anilino]piperidin-1-yl}sulfonyl)thien-2-yl]methyl}-3-methoxybenzamide
N-[(5-{[4-(3-chloroanilino)piperidin-1-yl]sulfonyl}thien-2-yl)methyl]-3-methoxybenzamide
N-[(5-{[4-(4-chloroanilino)piperidin-1-yl]sulfonyl}thien-2-yl)methyl]-3-methoxybenzamide
3-methoxy-N-({5-[(4-{4-[(trifluoromethyl)sulfonyl]anilino}piperidin-1-yl)sulfonyl]thien-2-yl}methyl)benzamide
N-({5-[(4-{3-[amino(imino)methyl]anilino}piperidin-1-yl)sulfonyl]thien-2-yl}methyl)-3-methoxybenzamide
N-({5-[(4-{3-[(2-hydroxyethyl)sulfonyl]anilino}piperidin-1-yl)sulfonyl]thien-2-yl}methyl)-3-methoxybenzamide
3-methoxy-N-({5-[(4-{3-[(trifluoromethyl)sulfonyl]anilino}piperidin-1-yl)sulfonyl]thien-2-yl}methyl)benzamide
N-({5-[(4-anilinopiperidin-1-yl)sulfonyl]thien-2-yl}methyl)-3-methoxybenzamide
3-methoxy-N-({5-[(4-{3-[(trifluoromethyl)sulfanyl]anilino}piperidin-1-yl)sulfonyl]thien-2-yl}methyl)benzamide
N-[(5-{[4-(4-hydroxyanilino)piperidin-1-yl]sulfonyl}thien-2-yl)methyl]-3-methoxybenzamide
3-nitro-N-({5-[(4-{3-[(trifluoromethyl)sulfanyl]anilino}piperidin-1-yl)sulfonyl]thien-2-yl}methyl)benzamide
4-nitro-N-({5-[(4-{3-[(trifluoromethyl)sulfanyl]anilino}piperidin-1-yl)sulfonyl]thien-2-yl}methyl)benzamide
N-[(5-{[4-(2-hydroxyanilino)piperidin-1-yl]sulfonyl}thien-2-yl)methyl]-3-methoxybenzamide
3-methoxy-N-[(5-{[4-(pyrimidin-2-ylamino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-3-methoxybenzamide N-[(5-{[4-({3-nitropyridin-2-yl}amino)piperidin-1-yl]
sulfonyl}thien-2-yl)methyl]-3-methoxybenzamide
N-{[5-({4-[(2,2-dioxido-1,3-dihydro-2-benzothien-5-yl)
amino]piperidin-1-yl}sulfonyl)thien-2-yl]methyl}-3-
methoxybenzamide
N-[(5-{[4-(2,3-dihydro-1H-inden-5-ylamino)piperidin-1-yl]
sulfonyl}thien-2-yl)methyl]-3-methoxybenzamide
3-methoxy-N-[(5-{[4-(2-propylanilino)piperidin-1-yl]
sulfonyl}thien-2-yl)methyl]benzamide
3-methoxy-N-[(5-{[4-(4-propylanilino)piperidin-1-yl]
sulfonyl}thien-2-yl)methyl]benzamide
N-[(5-{[4-(3-tert-butylanilino)piperidin-1-yl]
sulfonyl}thien-2-yl)methyl]-3-methoxybenzamide
N-({5-[(4-{[chloro-5-(trifluoromethyl)pyridin-2-yl]
amino}piperidin-1-yl)sulfonyl]thien-2-yl}methyl)-3-
methoxybenzamide
3-methoxy-N-{[5-({4-[3-(1,3-oxazol-5-yl)anilino]piperidin-1-yl}sulfonyl)thien-2-yl]methyl}benzamide
N-[(5-{[4-([1,1'-biphenyl]-3-ylamino)piperidin-1-yl]
sulfonyl}thien-2-yl)methyl]-3-methoxybenzamide
3-methoxy-N-[(5-{[4-(3-propylphenoxy)piperidin-1-yl]
sulfonyl}thien-2-yl)methyl]benzamide
3-methoxy-N-{[5-({4-[3-(morpholin-4-ylsulfonyl)anilino]
piperidin-1-yl}sulfonyl)thien-2-yl]methyl}benzamide
3-methoxy-N-[(5-{[4-(2-phenylethyl)piperidin-1-yl]
sulfonyl}thien-2-yl)methyl]benzamide
N-[(5-{[4-(3-benzylanilino)piperidin-1-yl]sulfonyl}thien-2-yl)methyl]-3-methoxybenzamide
3-methoxy-N-[(5-{[4-(3-phenylpropyl)piperazin-1-yl]
sulfonyl}thien-2-yl)methyl]benzamide
3-methoxy-N-({5-[(4-{[4-(trifluoromethyl)pyrimidin-2-yl]
amino}piperidin-1-yl)sulfonyl]thien-2-yl}methyl)benzamide
N-[(5-{[4-(3-cyclohexyl-4-hydroxyanilino)piperidin-1-yl]
sulfonyl}thien-2-yl)methyl]-3-methoxybenzamide
N-({5-[(4-{3-[(butylamino)sulfonyl]anilino}piperidin-1-yl)
sulfonyl]thien-2-yl}methyl)-3-methoxybenzamide
N-[(5-{[4-(3-ethylanilino)piperidin-1-yl]sulfonyl}thien-2-yl)methyl]-3-methoxybenzamide
3-methoxy-N-[(5-{[4-(5,6,7,8-tetrahydronapthalen-1-ylamino)piperidin-1-yl]sulfonyl}thien-2-yl)methyl]benzamide
N-(5-{[4-(1H-1,2,3-benzotriazol-1-yl)piperidin-1-yl]
sulfonyl}thien-2-yl)methyl]-5-nitro-1H-pyrazole-3-carboxamide
N-[(5-{[4-(1H-1,2,3-benzotriazol-1-yl)piperidin-1-yl]
sulfonyl}thien-2-yl)methyl]-2-oxo-1,2-dihydropyridine-3-carboxamide
N-[(5-{[4-(1H-1,2,3-benzotriazol-1-yl)piperidin-1-yl]
sulfonyl}thien-2-yl)methyl]-2-thioxo-1,2-dihydropyridine-3-carboxamide
N-[(5-{[4-(1H-1,2,3-benzotriazol-1-yl)piperidin-1-yl]
sulfonyl}thien-2-yl)methyl]-3,4-dihydroxybenzamide
N-[(5-{[4-(1H-1,2,3-benzotriazol-1-yl)piperidin-1-yl]
sulfonyl}thien-2-yl)methyl]pyridine-2-carboxamide
N-[(5-{[4-(hexyloxy)piperidin-1-yl]sulfonyl}thien-2-yl)
methyl]-3-methoxybenzamide
N-({5-[(4-heptanoylpiperidin-1-yl)sulfonyl]thien-2-yl}methyl)-3-methoxybenzamide
4-chloro-N-[(5-{[4-(3-propylanilino)piperidin-1-yl]sulfonyl}-2-furyl)methyl]benzamide
4-chloro-N-[(5-{[4-(3-chloroanilino)piperidin-1-yl]sulfonyl}-2-furyl)methyl]benzamide
4-chloro-N-[(5-{[4-(3-methoxyanilino)piperidin-1-yl]sulfonyl}-2-furyl)methyl]benzamide
4-chloro-N-{[5-({4-[3-(trifluoromethyl)anilino]piperidin-1-yl}sulfonyl)-2-furyl]methyl}benzamide
4-chloro-N-{[5-{(4-[3-(dimethylamino)anilino]piperidin-1-yl}sulfonyl)-2-furyl]methyl}benzamide
4-chloro-N-{[5-({4-[3-(methylsulfonyl)anilino]piperidin-1-yl}sulfonyl)-2-furyl]methyl}benzamide
4-chloro-N-{[5-({4-[3-(methylsulfanyl)anilino]piperidin-1-yl}sulfonyl)-2-furyl]methyl}benzamide
N-{[5-({4-[3-(aminosulfonyl)anilino]piperidin-1-yl}sulfonyl)-2-furyl]methyl}-4-chlorobenzamide
methyl 3-({1-[(5-{[(4-chlorobenzoyl)amino]methyl}-2-furyl)sulfonyl]piperidin-4-yl}amino)benzoate
3-({1-[(5-{[(4-chlorobenzoyl)amino]methyl}-2-furyl)sulfonyl]piperidin-4-yl}amino)benzamide
4-chloro-N-({5-[(4-{3-nitroanilino}piperidin-1-yl)sulfonyl]-2-furyl}methyl)benzamide
4-chloro-N-[(5-{[4-(2-methoxyanilino)piperidin-1-yl]sulfonyl}-2-furyl)methyl]benzamide
4-chloro-N-{[5-({4-[2-(trifluoromethyl)anilino]piperidin-1-yl}sulfonyl)-2-furyl]methyl}benzamide
4-chloro-N-({5-[(4-{2-nitroanilino}piperidin-1-yl)sulfonyl]-2-furyl}methyl)benzamide
4-chloro-N-[(5-{[4-(4-chloroanilino)piperidin-1-yl]sulfonyl}-2-furyl)methyl]benzamide
4-chloro-N-{[5-({4-[4-(trifluoromethyl)anilino]piperidin-1-yl}sulfonyl)-2-furyl]methyl}benzamide
4-chloro-N-({5-[(4-{4-[(trifluoromethyl)sulfonyl]
anilino}piperidin-1-yl)sulfonyl]-2-furyl}methyl)benzamide
N-{[5-({4-[4-(aminocarbonyl)anilino]piperidin-1-yl}sulfonyl)-2-furyl]methyl}-4-chlorobenzamide
4-chloro-N-{[5-({4-[4-(1,3-dithiolan-2-yl)anilino]piperidin-1-yl}sulfonyl)-2-furyl]methyl}benzamide
N-({5-[(4-{3-[amino(imino)methyl]anilino}piperidin-1-yl)
sulfonyl]-2-furyl}methyl)-4-chlorobenzamide
4-chloro-N-({5-[(4-{3-[(trifluoromethyl)sulfonyl]
anilino}piperidin-1-yl)sulfonyl]-2-furyl}methyl)benzamide
N-({5-[(4-anilinopiperidin-1-yl)sulfonyl]-2-furyl}methyl)-4-chlorobenzamide
4-nitro-N-({5-[(4-{3-[(trifluoromethyl)sulfanyl]
anilino}piperidin-1-yl)sulfonyl]2-furyl}methyl)benzamide
4-chloro-N-({5-[(3-{3-[(trifluoromethyl)sulfonyl]
anilino}pyrrolidin-1-yl)sulfonyl]thien-2-yl}methyl)benzamide
4-chloro-N-({5-[(4-{3-[(trifluoromethyl)sulfonyl]
anilino}azepan-1-yl)sulfonyl]thien-2-yl}methyl)benzamide
5-{[(3-methoxybenzoyl)amino]methyl}-2-[(4-{3-[(trifluoromethyl)sulfonyl]-anilino}piperidin-1-yl)sulfonyl]
thiophene-3-carboxylic acid
5-{[(3-methoxybenzoyl)amino]methyl}-2-{[4-(octylamino)
piperidin-1-yl]sulfonyl}thiopene-3-carboxylic acid
N-(2-hydroxyethyl)-5-{[(3-methoxybenzoyl)amino]methyl}-2-[(4-{3-[(trifluoro-methyl)sulfonyl]
anilino}piperidin-1-yl)sulfonyl]thiophene-3-carboxamide
N-({4-(hydrazinocarbonyl)-5-[(4-{3-[(trifluoromethyl)sulfonyl]anilino}-piperidin-1-yl)sulfonyl]thien-2-yl}methyl)-3-methoxybenzamide
5-{[(3-methoxybenzoyl)amino]methyl}-2-[(4-{3-[(trifluoromethyl)sulfonyl]-anilino}piperidin-1-yl)sulfonyl]
thiophene-3-carboxamide
N-[2-(dimethylamino)ethyl-5-{[(3-methoxybenzoyl)
amino]methyl}-2-[(4-{3-[(trifluoromethyl)sulfonyl]
anilino}piperidin-1-yl)sulfonyl]thiophene-3-carboxamide N-({4-(hydroxymethyl)-5-[(4-{3-[(trifluoromethyl)sulfonyl]anilino}piperidin-1-yl)sulfonyl]thien-2-yl}methyl)-3-methoxybenzamide 4-chloro-N-[(5-{[4-(hexylamino)piperidin-1-yl]sulfonyl}thien-2-yl)methyl]benzamide 3-Methoxy-N-{[5-({4-[(4-trifluoromethylbenzyl)amino]piperidin-1-yl}sulfonyl)thien-2-yl]methyl}benzamide 4-chloro-N-[(5-{[4-(1,3-thiazol-2-ylamino)piperidin-1-yl]sulfonyl}thien-2-yl)methyl]benzamide 4-chloro-N-[(5-{[4-(heptylamino)piperidin-1-yl]sulfonyl}thien-2-yl)methyl]benzamide 4-chloro-N-[(5-{[4-(pentylamino)piperidin-1-yl]sulfonyl}thien-2-yl)methyl]benzamide 4-chloro-N-[(5-{[4-(butylamino)piperidin-1-yl]sulfonyl}thien-2-yl)methyl]benzamide 4-chloro-N-[(5-{[4-(dodecylamino)piperidin-1-yl]sulfonyl}thien-2-yl)methyl]benzamide 4-chloro-N-{[5-({4-[(2-cyclohexylethyl)amino]piperidin-1-yl}sulfonyl)thien-2-yl]methyl}benzamide 4-chloro-N-{[5-({4-[(cyclohexylmethyl)amino]piperidin-1-yl}sulfonyl)thien-2-yl]methyl}benzamide 4-chloro-N-({5-[(4-{[(1R)-1-cyclohexylethyl]amino}piperidin-1-yl)sulfonyl]thien-2-yl}methyl)benzamide N-{[5-({4-[(1R,2R,4S)-bicyclo[2.2.1]hept-2-ylamino]piperidin-1-yl}sulfonyl)thien-2-yl]methyl}-4-chlorobenzamide 4-chloro-N-{[5-({4-[(2-propoxyethyl)amino]piperidin-1-yl}sulfonyl)thien-2-yl]methyl}benzamide N-{[5-({4-[(1-adamantylmethyl)amino]piperidin-1-yl}sulfonyl)thien-2-yl]methyl}-4-chlorobenzamide 4-chloro-N-{[5-({4-[(2-pyridin-2-ylethyl)amino]piperidin-1-yl}sulfonyl)thien-2-yl]methyl}benzamide 4-chloro-N-{[5-({4-[(2-piperidin-1-ylethyl)amino]piperidin-1-yl}sulfonyl)thien-2-yl]methyl}benzamide 4-chloro-N-{[5-({4-[(2-ethylhexyl)amino]piperidin-1-yl}sulfonyl)thien-2-yl]methyl}benzamide 4-chloro-N-({5-[(4-{[3-(1H-imidazol-1-yl)propyl]amino}piperidin-1-yl)sulfonyl]thien-2-yl}methyl)benzamide 4-chloro-N-[(5-{[4-(octylamino)piperidin-1-yl]sulfonyl}thien-2-yl)methyl]benzamide N-[(5-{[4-(heptylamino)piperidin-1-yl]sulfonyl}thien-2-yl)methyl]-3-methoxybenzamide 3-methoxy-N-[(5-{[4-(octylamino)piperidin-1-yl]sulfonyl}thien-2-yl)methyl]benzamide 3-methoxy-N-[(5-{[4-(pentylamino)piperidin-1-yl]sulfonyl}thien-2-yl)methyl]benzamide N-[(5-{[4-(butylamino)piperidin-1-yl]sulfonyl}thien-2-yl)methyl]-3-methoxybenzamide N-[(5-{[4-(dodecylamino)piperidin-1-yl]sulfonyl}thien-2-yl)methyl]-3-methoxybenzamide N-{[5-({4-[(2-cyclohexylethyl)amino]piperidin-1-yl}sulfonyl)thien-2-yl]methyl}-3-methoxybenzamide N-({5-[(4-{[(1R)-1-cyclohexylethyl]amino}piperidin-1-yl)sulfonyl]thien-2-yl}methyl)-3-methoxybenzamide N-{[5-({4-[(1R,2R,4S)-bicyclo[2.2.1]hept-2-ylamino]piperidin-1-yl}sulfonyl)thien-2-yl]methyl}-3-methoxybenzamide 3-methoxy-N-{[5-({4-[(2-propoxyethyl)amino]piperidin-1-yl}sulfonyl)thien-2-yl]methyl}benzamide N-{[5-({4-[(1-adamantylmethyl)amino]piperidin-1-yl}sulfonyl)thien-2-yl]methyl}-3-methoxybenzamide N-{[5-({4-[(3,3-diethoxypropyl)amino]piperidin-1-yl}sulfonyl)thien-2-yl]methyl}-3-methoxybenzamide 3-methoxy-N-{[5-({4-[(3-morpholin-4-ylpropyl)amino]piperidin-1-yl}sulfonyl)thien-2-yl]methyl}benzamide 3-methoxy-N-{[5-({4-[(2-pyridin-2-ylethyl)amino]piperidin-1-yl}sulfonyl)thien-2-yl]methyl}benzamide 3-methoxy-N-{[5-({4-[(2-piperidin-1-ylethyl)amino]piperidin-1-yl}sulfonyl)thien-2-yl]methyl}benzamide N-{[5-({4-[(2-ethylhexyl)amino]piperidin-1-yl}sulfonyl)thien-2-yl]methyl}-3-methoxybenzamide N-({5-[(4-{[3-(1H-imidazol-1-yl)propyl]amino}piperidin-1-yl)sulfonyl]thien-2-yl}methyl)-3-methoxybenzamide N-[(5-{[4-hexylamino)piperidin-1-yl]sulfonyl}thien-2-yl)methyl]-3-methoxybenzamide N-[(5-{[4-(heptylamino)azepan-1-yl]sulfonyl}thien-2-yl)methyl]-3-methoxybenzamide 3-methoxy-N-[(5-{[4-(octylamino)azepan-1-yl]sulfonyl}thien-2-yl)methyl]benzamide 3-methoxy-N-[(5-{[4-(pentylamino)azepan-1-yl]sulfonyl}thien-2-yl)methyl]benzamide N-[(5-{[4-(butylamino)azepan-1-yl]sulfonyl}thien-2-yl)methyl]-3-methoxybenzamide N-[(5-{[4-(dodecylamino)azepan-1-yl]sulfonyl}thien-2-yl)methyl]-3-methoxybenzamide N-{[5-({4-[(2-cyclohexylethyl)amino]azepan-1-yl}sulfonyl)thien-2-yl]methyl}-3-methoxybenzamide N-({5-[(4-{[(1R)-1-cyclohexylethyl]amino}azepan-1-yl)sulfonyl]thien-2-yl}methyl)-3-methoxybenzamide N-{[5-({4-[(1R,2R,4S)-bicyclo[2.2.1]hept-2-ylamino]azepan-1-yl}sulfonyl)thien-2-yl]methyl}-3-methoxybenzamide 3-methoxy-N-{[5-({4-[(2-propoxyethyl)amino]azepan-1-yl}sulfonyl)thien-2-yl]methyl}benzamide N-{[5-({4-[(cyclohexylmethyl)amino]azepan-1-yl}sulfonyl)thien-2-yl]methyl}-3-methoxybenzamide N-{[5-({4-[(1-adamantylmethyl)amino]azepan-1-yl}sulfonyl)thien-2-yl]methyl}-3-methoxybenzamide 3-methoxy-N-{[5-({4-[(3-morpholin-4-ylpropyl)amino]azepan-1-yl}sulfonyl)thien-2-yl]methyl}benzamide 3-methoxy-N-{[5-({4-[(2-pyridin-2-ylethyl)amino]azepan-1-yl}sulfonyl)thien-2-yl]methyl}benzamide 3-methoxy-N-{[5-({4-[(2-piperidin-1-ylethyl)amino]azepan-1-yl}sulfonyl)thien-2-yl]methyl}benzamide N-{[5-({4-[(2-ethylhexyl)amino]azepan-1-yl}sulfonyl)thien-2-yl]methyl}-3-methoxybenzamide N-({5-[(4-{[3-(1H-imidazol-1-yl)propyl]amino}azepan-1-yl)sulfonyl]thien-2-yl}methyl)-3-methoxybenzamide 4-chloro-N-[(5-{[4-(heptylamino)azepan-1-yl]sulfonyl}thien-2-yl)methyl]benzamide 4-chloro-N-[(5-{[4-(octylamino)azepan-1-yl]sulfonyl}thien-2-yl)methyl]benzamide 4-chloro-N-[(5-{[4-(pentylamino)azepan-1-yl]sulfonyl}thien-2-yl)methyl]benzamide N-[(5-{[4-(butylamino)azepan-1-yl]sulfonyl}thien-2-yl)methyl]-4-chlorobenzamide 4-chloro-N-[(5-{[4-(dodecylamino)azepan-1-yl]sulfonyl}thien-2-yl)methyl]benzamide 4-chloro-N-{[5-({4-[(2-cyclohexylethyl)amino]azepan-1-yl}sulfonyl)thien-2-yl]methyl}benzamide N-{[5-({4-[(1R,2R,4S)-bicyclo[2.2.1]hept-2-ylamino]azepan-1-yl}sulfonyl)thien-2-yl]methyl}-4-chlorobenzamide 4-chloro-N-{[5-({4-[(2-propoxyethyl)amino]azepan-1-yl}sulfonyl)thien-2-yl]methyl}benzamide 4-chloro-N-{[5-({4-[(2-ethylhexyl)amino]azepan-1-yl}sulfonyl)thien-2-yl]methyl}benzamide 4-chloro-N-[(5-{[4-(hexylamino)azepan-1-yl]sulfonyl}thien-2-yl)methyl]benzamide N-[(5-{[4-(hexylamino)azepan-1-yl]sulfonyl}thien-2-yl)methyl]-3-methoxybenzamide 3-methoxy-N-[(5-{[4-({2-[3-(trifluoromethyl)phenyl]
  ethyl}amino)piperidin-1-yl]sulfonyl}thien-2-yl)methyl]
  benzamide
3-methoxy-N-({5-[(4-{[2-(4-methylphenyl)ethyl]
  amino}piperidin-1-yl)sulfonyl]thien-2-yl}methyl)benza-
  mide
3-methoxy-N-({5-[(4-{[(1S,2R)-2-phenylcyclopropyl]
  amino}piperidin-1-yl)sulfonyl]thien-2-yl}methyl)benza-
  mide
3-methoxy-N-{[5-({4-[(1-naphthylmethyl)amino]piperidin-
  1-yl}sulfonyl)thien-2-yl]methyl}benzamide
3-methoxy-N-{[5-({4-[(2-phenylpropyl)amino]piperidin-1-
  yl}sulfonyl)thien-2-yl]methyl}benzamide
N-({5-[(4-{[2-(4-hydroxyphenyl)ethyl]amino}piperidin-1-
  yl)sulfonyl]thien-2-yl}methyl)-3-methoxybenzamide
3-methoxy-N-{([5-({4-[(3-phenylpropyl)amino]piperidin-
  1-yl}sulfonyl)thien-2-yl]methyl}benzamide
N-{[5-({4-[(2,3-dihydroxypropyl)amino]piperidin-1-
  yl}sulfonyl)thien-2-yl]methyl}-3-methoxybenzamide
N-{[5-({4-[(2-hydroxyethyl)amino]piperidin-1-yl}sulfonyl)
  thien-2-yl]methyl}-3-methoxybenzamide
3-methoxy-N-[(5-{[4-(nonylamino)piperidin-1-yl]
  sulfonyl}thien-2-yl)methyl]benzamide
3-methoxy-N-[(5-{[4-(decylamino)piperidin-1-yl]
  sulfonyl}thien-2-yl)methyl]benzamide
3-methoxy-N-[(5-{[4-(ethylamino)piperidin-1-yl]
  sulfonyl}thien-2-yl)methyl]benzamide
N-{[5-({4-[(2-[1,1'-biphenyl]-4-ylethyl)amino]piperidin-1-
  yl}sulfonyl)thien-2-yl]methyl}-3-methoxybenzamide
N-{[5-({4-[([1,1'-biphenyl]-3-ylmethyl)amino]piperidin-1-
  yl}sulfonyl)thien-2-yl]methyl}-3-methoxybenzamide
3-methoxy-N-{[5-({4-[(2-thien-2-ylethyl)amino]piperidin-
  1-yl}sulfonyl)thien-2-yl]methyl}benzamide
3-methoxy-N-[(5-{[4-({4-[(trifluoromethyl)sulfonyl]
  benzyl}amino)piperidin-1-yl]sulfonyl}thien-2-yl)methyl]
  benzamide
3-methoxy-N-{[5-({4-[(quinolin-4-ylmethyl)amino]piperi-
  din-1-yl}sulfonyl)thien-2-yl]methyl}benzamide
N-{[5-({4-[([1,1'-biphenyl]-4-ylmethyl)amino]-1-
  piperidinyl}sulfonyl)-2-thienyl]methyl}-3-methoxyben-
  zamide
4-chloro-N-{[5-({4-[(2-{[(trifluoromethyl)sulfonyl]
  amino}ethyl)amino]-1-piperidinyl}sulfonyl)-2-thienyl]
  methyl}benzamide
4-chloro-N-[(5-{[4-(propylamino)-1-piperidinyl]sulfonyl}-
  2-thienyl)methyl]benzamide
4-chloro-N-[(5-{[4-({4-[(trifluoromethyl)sulfonyl]
  benzyl}amino)-1-piperidinyl]sulfonyl}-2-thienyl)methyl]
  benzamide
4-chloro-N-{[5-({4-[(3,4-dihydroxybenzyl)amino]-1-
  piperidinyl}sulfonyl)-2-thienyl]methyl}benzamide
methyl   [{1-[(5-{[(4-chlorobenzoyl)amino]methyl}-2-thie-
  nyl)sulfonyl]-4-piperidinyl}(hexyl)amino]acetate
tert-butyl   [{1-[(5-{[(4-chlorobenzoyl)amino]methyl}-2-
  thienyl)sulfonyl]-4-piperidinyl}hexyl)amino]acetate
[{1-[(5-{[(4-chlorobenzoyl)amino]methyl}-2-thienyl)sulfo-
  nyl]-4-piperidinyl}(hexyl)amino]acetic acid
N-[(5-{[3-(heptylamino)pyrrolidin-1-yl]sulfonyl}thien-2-
  yl)methyl]-3-methoxybenzamide
3-methoxy-N-[(5-{[3-(octylamino)pyrrolidin-1-yl]
  sulfonyl}thien-2-yl)methyl]benzamide
3-methoxy-N-[(5-{[3-(pentylamino)pyrrolidin-1-yl]
  sulfonyl}thien-2-yl)methyl]benzamide
N-[(5-{[3-(butylamino)pyrrolidin-1-yl]sulfonyl}thien-2-yl)
  methyl]-3-methoxybenzamide
N-[(5-{[3-(dodecylamino)pyrrolidin-1-yl]sulfonyl}thien-2-
  yl)methyl]-3-methoxybenzamide
N-{[5-({3-[(2-cyclohexylethyl)amino]pyrrolidin-1-
  yl}sulfonyl)thien-2-yl]methyl}-3-methoxybenzamide
N-({5-[(3-{[(1R)-1-cyclohexylethyl]amino}pyrrolidin-1-yl)
  sulfonyl]thien-2-yl}methyl)-3-methoxybenzamide
N-{[5-({3-[(1R,2R,4S)-bicyclo[2.2.1]hept-2-ylamino]pyr-
  rolidin-1-yl}sulfonyl)thien-2-yl]methyl}-3-methoxyben-
  zamide
3-methoxy-N-{[5-({3-[(2-propoxyethyl)amino]pyrrolidin-
  1-yl}sulfonyl)thien-2-yl]methyl}benzamide
N-{[5-({3-[(cyclohexylmethyl)amino]pyrrolidin-1-
  yl}sulfonyl)thien-2-yl]methyl}-3-methoxybenzamide
N-{[5-({3-[(1-adamantylmethyl)amino]pyrrolidin-1-
  yl}sulfonyl)thien-2-yl]methyl}-3-methoxybenzamide
3-methoxy-N-{[5-({3-[(3-morpholin-4-ylpropyl)amino]
  pyrrolidin-1-yl}sulfonyl)thien-2-yl]methyl}benzamide
3-methoxy-N-{[5-({3-[(2-pyridin-2-ylethyl)amino]pyrroli-
  din-1-yl) sulfonyl}thien-2-yl]methyl}benzamide
3-methoxy-N-{[5-({3-[(2-piperidin-1-ylethyl)amino]pyrro-
  lidin-1-yl}sulfonyl)thien-2-yl]methyl}benzamide
N-{[5-({3-[(2-ethylhexyl)amino]pyrrolidin-1-yl}sulfonyl)
  thien-2-yl]methyl}-3-methoxybenzamide
N-[(5-{[3-(hexylamino)pyrrolidin-1-yl]sulfonyl}thien-2-yl)
  methyl]-3-methoxybenzamide
4-chloro-N-[(5-{[3-(heptylamino)pyrrolidin-1-yl]
  sulfonyl}thien-2-yl)methyl]benzamide
4-chloro-N-[(5-{[3-(hexylaminopyrrolidin-1-yl]
  sulfonyl}thien-2-yl)methyl]benzamide
4-chloro-N-[(5-{[3-(pentylamino)pyrrolidin-1-yl]
  sulfonyl}thien-2-yl)methyl]benzamide
N-[(5-{[3-(butylamino)pyrrolidin-1-yl]sulfonyl}thien-2-yl)
  methyl]-4-chlorobenzamide
4-chloro-N-{[5-({3-[(2-cyclohexylethyl)amino]pyrrolidin-
  1-yl}sulfonyl)thien-2-yl]methyl}benzamide
N-{[5-({3-[(1R,2R,4S)-bicyclo[2.2.1]hept-2-ylamino]pyr-
  rolidin-1-yl}sulfonyl)thien-2-yl]methyl}-4-chlorobenza-
  mide
4-chloro-N-({5-[(3-{[(1-hydroxycyclohexyl)methyl]
  amino}pyrrolidin-1-yl)sulfonyl]thien-2-yl}methyl)ben-
  zamide
N-{[5-({3-[(1-adamantylmethyl)amino]pyrrolidin-1-
  yl}sulfonyl)thien-2-yl]methyl}-4-chlorobenzamide
4-chloro-N-{[5-({3-[(3-morpholin-4-ylpropyl)amino]pyrro-
  lidin-1-yl}sulfonyl)thien-2-yl]methyl}benzamide
4-chloro-N-{[5-({3-[(2-pyridin-2-ylethyl)amino]pyrrolidin-
  1-yl}sulfonyl)thien-2-yl]methyl}benzamide
4-chloro-N-{[5-({3-[(2-piperidin-1-ylethyl)amino]pyrroli-
  din-1-yl}sulfonyl)thien-2-yl]methyl}benzamide
4-chloro-N-{[5-({3-[(2-ethylhexyl)amino]pyrrolidin-1-
  yl}sulfonyl)thien-2-yl]methyl}benzamide
4-chloro-N-[(5-{[3-(octylamino)pyrrolidin-1-yl]
  sulfonyl}thien-2-yl)methyl]benzamide
methyl   (2S)-1-[(5-{[(4-chlorobenzoyl)amino]methyl}-2-
  thienyl)sulfonyl]-4-hexylamino)-2-pyrrolidinecarboxy-
  late
3-methoxy-N-{[5-({4-[(pentylamino)methyl]piperidin-1-
  yl}sulfonyl)thien-2-yl]methyl}benzamide
N-{[5-({4-[2-(butylamino)ethyl]piperidin-1-yl}sulfonyl)
  thien-2-yl]methyl}-3-methoxybenzamide
N-{[5-({4-[(4-butylanilino)methyl]-1-
  piperidinyl}sulfonyl)-2-thienyl]methyl}-3-methoxyben-
  zamide
4-chloro-N-{[5-({4-[hexyl(methyl)amino]piperidin-1-
  yl}sulfonyl)thien-2-yl]methyl}benzamide
4-chloro-N-{[5-({4-[(cyclohexylmethyl)(hexyl)amino]pip-
  eridin-1-yl}sulfonyl)thien-2-yl]methyl}benzamide
N-{[5-({4-[benzyl(hexyl)amino]piperidin-1-yl}sulfonyl)
  thien-2-yl]methyl}-4-chlorobenzamide 4-chloro-N-{[5-({4-[hexyl(pyridin-3-ylmethyl)amino]piperidin-1-yl}sulfonyl)thien-2-yl]methyl}benzamide
4-chloro-N-{[5-({4-[hexyl(pyridin-4-ylmethyl)amino]piperidin-1-yl}sulfonyl)thien-2-yl]methyl}benzamide
4-chloro-N-{[5-({4-[hexyl(pyridin-2-ylmethyl)amino]piperidin-1-yl}sulfonyl)thien-2-yl]methyl}benzamide
N-{[5-({4-[butyl(hexyl)amino]piperidin-1-yl}sulfonyl)thien-2-yl]methyl}-4-chlorobenzamide
4-chloro-N-{[5-({4-[hexyl(3-phenylpropyl)amino]piperidin-1-yl}sulfonyl)thien-2-yl]methyl}benzamide
4-chloro-N-{[5-({4-[hexyl(2-phenylethyl)amino]piperidin-1-yl}sulfonyl)thien-2-yl]methyl}benzamide
N-{[5-({4-[[(5-bromo-2-furyl)methyl](hexyl)amino]piperidin-1-yl}sulfonyl)thien-2-yl]methyl}-4-chlorobenzamide
3-methoxy-N-({5-[(4-{methyl[4-(trifluoromethyl)benzyl]amino}-1-piperidinyl)sulfonyl]-2-thienyl}methyl)benzamide
4-chloro-N-{[5-({4-[(3-chlorobenzyl)amino]piperidin-1-yl}sulfonyl)thien-2-yl]methyl}benzamide
3-methoxy-N-({5-[(4-{[4-(trifluoromethyl)benzyl]amino}piperidin-1-yl)sulfonyl]thien-2-yl}methyl)benzamide
3-methoxy-N-{[5-({4-[(3-methylbenzyl)amino]piperidin-1-yl}sulfonyl)thien-2-yl]methyl}benzamide
3-methoxy-N-{[5-({4-[(4-propylbenzyl)amino]piperidin-1-yl)sulfonyl)thien-2-yl]methyl}benzamide
3-methoxy-N-({5-[(4-{[3-(trifluoromethyl)benzyl]amino}piperidin-1-yl)sulfonyl]thien-2-yl}methyl)benzamide
3-methoxy-N-({5-[(4-{[4-(trifluoromethoxy)benzyl]amino}piperidin-1-yl)sulfonyl]thien-2-yl}methyl)benzamide
N-({5-[(4-{[4-(difluoromethoxy)benzyl]amino}piperidin-1-yl)sulfonyl]thien-2-yl}methyl)-3-methoxybenzamide
3-methoxy-N-{[5-({4-[(2,3,4,5,6-pentamethylbenzyl)amino]piperidin-1-yl}sulfonyl)thien-2-yl]methyl}benzamide
3-methoxy-N-{[5-({4-[(4-propoxybenzyl)amino]piperidin-1-yl}sulfonyl)thien-2-yl]methyl}benzamide
N-{[5-({4-[(4-butoxybenzyl)amino]piperidin-1-yl}sulfonyl)thien-2-yl]methyl}-3-methoxybenzamide
3-methoxy-N-{[5-({4-[(4-methoxybenzyl)amino]piperidin-1-yl}sulfonyl)thien-2-yl]methyl}benzamide
3-methoxy-N-{[5-({4-[(pyridin-4-ylmethyl)amino]piperidin-1-yl}sulfonyl)thien-2-yl]methyl}benzamide
3-methoxy-N-{[5-({4-[(pyridin-2-ylmethyl)amino]piperidin-1-yl}sulfonyl)thien-2-yl]methyl}benzamide
3-methoxy-N-{[5-({4-[(pyridin-3-ylmethyl)amino]piperidin-1-yl}sulfonyl)thien-2-yl]methyl}benzamide
N-{[5-({4-[(4-tert-butylbenzyl)amino]piperidin-1-yl}sulfonyl)thien-2-yl]methyl}-3-methoxybenzamide
N-{[5-({4-[(3-ethoxybenzyl)amino]piperidin-1-yl}sulfonyl)thien-2-yl]methyl}-3-methoxybenzamide
3-methoxy-N-{[5-({4-[(4-phenoxybenzyl)amino]piperidin-1-yl}sulfonyl)thien-2-yl]methyl}benzamide
3-methoxy-N-(5-{[4-({4-[(trifluoromethyl)sulfanyl]benzyl}amino)piperidin-1-yl]sulfonyl}thien-2-yl)methyl]benzamide
3-methoxy-N-({5-[(4-{[4-(methylsulfonyl)benzyl]amino}-1-piperidinyl)sulfonyl]-2-thienyl}methyl)benzamide
N-({5-[(4-{[3,5-bis(trifluoromethyl)benzyl]amino}-1-piperidinyl)sulfonyl]-2-thienyl}methyl)-3-methoxybenzamide
N-({5-[(4-{[2,5-bis(trifluoromethyl)benzyl]amino}-1-piperidinyl)sulfonyl]-2-thienyl}methyl)-3-methoxybenzamide
N-({5-[(4-{[4-(ethylsulfanyl)benzyl]amino}-1-piperidinyl)sulfonyl]-2-thienyl}methyl)-3-methoxybenzamide
3-methoxy-N-[(5-{[4-({3-[(trifluoromethyl)sulfanyl]benzyl}amino)-1-piperidinyl]sulfonyl}-2-thienyl)methyl]benzamide
N-({5-[(4-{[(2,2-difluoro-1,3-benzodioxol-5-yl)methyl]amino}-1-piperidinyl)sulfonyl]-2-thienyl}methyl)-3-methoxybenzamide
N-{[5-({4-[(4-iodobenzyl)amino]-1-piperidinyl}sulfonyl)-2-thienyl]methyl}-3-methoxybenzamide
N-({5-[(4-{[4-(benzyloxy)benzyl]amino}-1-piperidinyl)sulfonyl]-2-thienyl}methyl)-3-methoxybenzamide
N-{[5-({4-[(mesitylmethyl)amino]-1-piperidinyl}sulfonyl)-2-thienyl]methyl}-3-methoxybenzamide
N-{[5-({4-[(4-chlorobenzyl)amino)]-1-piperidinyl}sulfonyl)-2-thienyl]methyl}-3-methoxybenzamide
N-{[5-({4-[(4-ethylbenzyl)amino]-1-piperidinyl}sulfonyl)-2-thienyl]methyl}-3-methoxybenzamide
3-methoxy-N-{[5-({4-[(4-pentylbenzyl)amino]-1-piperidinyl}sulfonyl)-2-thienyl]methyl}benzamide
3-methoxy-N-[(5-{[4-({1-[4-(trifluoromethyl)phenyl]ethyl}amino)-1-piperidinyl]sulfonyl}-2-thienyl)methyl]benzamide
3-methoxy-N-{[5-({4-[(4-methylbenzyl)amino]-1-piperidinyl}sulfonyl)-2-thienyl]methyl}benzamide
N-{[5-({4-[(4-butylbenzyl)amino]-1-piperidinyl}sulfonyl)-2-thienyl]methyl}-3-methoxybenzamide
N-{[5-({4-[(4-isopropylbenzyl)amino]-1-piperidinyl}sulfonyl)-2-thienyl]methyl}-3-methoxybenzamide
N-{[5-({4-[(4-isobutylbenzyl)amino]-1-piperidinyl}sulfonyl)-2-thienyl]methyl}-3-methoxybenzamide
N-({5-[(4-{[(1-hydroxy-1lambda-5-pyridin-4-yl)methyl]amino}-1-piperidinyl)sulfonyl]-2-thienyl}methyl)-3-methoxybenzamide
N-{[5-({4-[(2,3-dihydro-1,4-benzodioxin-6-ylmethyl)amino]-1-piperidinyl}sulfonyl)-2-thienyl]methyl}-3-methoxybenzamide
N-{[5-({4-[(2,3-dihydro-1-benzofuran-5-ylmethyl)amino]-1-piperidinyl}sulfonyl)-2-thienyl]methyl}-3-methoxybenzamide
4-chloro-N-{[5-({4-[(4-propylbenzyl)amino]-1-piperidinyl}sulfonyl)-2-thienyl]methyl}benzamide
4-chloro-N-({5-[(4-{[4-(trifluoromethoxy)benzyl]amino}-1-piperidinyl)sulfonyl]-2-thienyl}methyl)benzamide
4-chloro-N-({5-[(4-{[4-(difluoromethoxy)benzyl]amino}-1-piperidinyl)sulfonyl]-2-thienyl}methyl)benzamide
4-chloro-N-{[5-({4-[(4-propoxybenzyl)amino]-1-piperidinyl}sulfonyl)-2-thienyl]methyl}benzamide
N-{[5-({4-[(4-butoxybenzyl)amino]-1-piperidinyl}sulfonyl)-2-thienyl]methyl}-4-chlorobenzamide
4-chloro-N-{[5-({4-[(4-quinolinylmethyl)amino]-1-piperidinyl}sulfonyl)-2-thienyl]methyl}benzamide
N-{[5-({4-[(4-tert-butylbenzyl)amino]-1-piperidinyl}sulfonyl)-2-thienyl]methyl}-4-chlorobenzamide
4-chloro-N-{[5-({4-[(4-phenoxybenzyl)amino]-1-piperidinyl}sulfonyl)-2-thienyl]methyl}benzamide
4-chloro-N-[(5-{[4-({4-[(trifluoromethyl)sulfanyl]benzyl}amino)-1-piperidinyl]sulfonyl}-2-thienyl)methyl]benzamide
4-chloro-N-({5-[(4-{[4-(trifluoroethyl)benzyl]amino}-1-1-piperidinyl]sulfonyl]-2-thienyl}methyl)benzamide 3-methoxy-N-({5-[(4-{[2-(trifluoromethyl)benzyl]amino}-1-piperidinyl)sulfonyl]-2-thienyl}methyl)benzamide
3-methoxy-N-[(5-{[4-({[6-(trifluoromethyl)-3-pyridinyl]methyl}amino)-1-piperidinyl]sulfonyl}-2-thienyl)methyl]benzamide
N-[(5-{[4-(benzylamino)-1-piperidinyl]sulfonyl}-2-thienyl)methyl]-3-methoxybenzamide
3-methoxy-N-[(5-{[4-({1-[4-(trifluoromethyl)phenyl]propyl}amino)-1-piperidinyl]sulfonyl}-2-thienyl)methyl]benzamide
3-methoxy-N-[(5-{[4-({1-methyl-1-[4-(trifluoromethyl)phenyl]ethyl}amino)-1-piperidinyl]sulfonyl}-2-thienyl)methyl]benzamide
4-chloro-N-[(5-{[4-({1-[4-(trifluoromethyl)phenyl]ethyl}amino)-1-piperidinyl]sulfonyl}-2-thienyl)methyl]benzamide
4-chloro-N-[(5-{[4-({1-methyl-1-[4-(trifluoromethyl)phenyl]ethyl}amino)-1-piperidinyl]sulfonyl}-2-thienyl)methyl]benzamide
4-chloro-N-[(5-{[2-({[4-(trifluoromethyl)benzyl]amino}methyl)-1-pyrrolidinyl]sulfonyl}-2-thienyl)methyl]benzamide
4-chloro-N-[(5-{[(3R)-3-({[4-(trifluoromethyl)benzyl]amino}methyl)pyrrolidinyl]sulfonyl}-2-thienyl)methyl]benzamide
4-chloro-N-({5-[(3-{[4-(trifluoromethyl)benzyl]amino}-1-piperidinyl)sulfonyl]-2-thienyl}methyl)benzamide
4-chloro-N-{[5-({3-[(hexylamino)methyl]-1-piperidinyl}sulfonyl)-2-thienyl]methyl}benzamide
4-chloro-N-({5-[(3-{[4-(trifluoromethyl)benzyl]amino}-1-pyrrolidinyl)sulfonyl]-2-thienyl}methyl)benzamide
4-chloro-N-{[5-({(3R)-3-[(hexylamino)methyl]pyrrolidinyl}sulfonyl)-2-thienyl]methyl}benzamide
4-chloro-N-[(5-{[3-({[4-(trifluoromethyl)benzyl]amino}methyl)-1-piperidinyl]sulfonyl}-2-thienyl)methyl]benzamide
2-oxo-N-({5-[(4-{[4-(trifuoromethyl)benzyl]amino}-1-piperidinyl)sulfonyl]-2-thienyl}methyl)-1,2-dihydro-3-pyridinecarboxamide
N-[(5-{[4-(hexylamino)-1-piperidinyl]sulfonyl}-2-thienyl)methyl]-2-oxo-1,2-dihydro-3-pyridinecarboxamide
N-[(5-{[4-(hexylamino)-1-piperidinyl]sulfonyl}-2-thienyl)methyl]-2-hydroxybenzamide
2-hydroxy-N-({5-[(4-{[4-(trifluoromethyl)benzyl]amino}-1-piperidinyl)sulfonyl]-2-thienyl}methyl)benzamide
N-[(5-{[4-(hexylamino)-1-piperidinyl]sulfonyl}-2-thienyl)methyl]-2-thioxo-1,2-dihydro-3-pyridinecarboxamide
2-thioxo-N-({5-[(4-{[4-(trifluoromethyl)benzyl]amino}-1-piperidinyl)sulfonyl]-2-thienyl}methyl)-1,2-dihydro-3-pyridinecarboxamide
N-[(5-{[4-(butylamino)-1-piperidinyl]sulfonyl}-2-thienyl)methyl]-2-oxo-1,2-dihydro-3-pyridinecarboxamide
N-({5-[(4-{ethyl[4-(trifluoromethyl)benzyl]amino}-1-piperidinyl)sulfonyl]-2-thienyl}methyl)-3-methoxybenzamide
4-chloro-N-[(5-{[4-({imino[4-(trifluoromethyl)phenyl]methyl}amino)-1-piperidinyl]sulfonyl}-2-thienyl)methyl]benzamide
1-[(5-{[(4-chlorobenzoyl)amino]methyl}-2-thienyl)sulfonyl]-4-(hexylamino)proline
ethyl 2-{[4-(hexylamino)piperidin-1-yl]sulfonyl}-5-{[(3-methoxybenzoyl)amino]methyl}thiophene-3-carboxylate
N-{[5-{[4-(hexylamino)piperidin-1-yl]sulfonyl}-4-(trimethylsilyl)thien-2-yl]methyl}-3-methoxybenzamide
N-({5-{[4-(hexylamino)piperidin-1-yl]sulfonyl}-4-[hydroxy(phenyl)methyl]thien-2-yl}methyl)-3-methoxybenzamide
5-[(3-Methoxy-benzoylamino)-methyl]-2-[4-(4-trifluoromethyl-benzylamino)-piperidine-1-sulfonyl]-thiophene-3-carboxylic acid ethyl ester
N-[(4-chloro-5-{[4-(hexylamino)piperidin-1-yl]sulfonyl}thien-2-yl)methyl]-3-methoxybenzamide The compounds of formula (I) may be obtained according to the methods described in any of WO 01/23378, WO 02/28856 and WO 02/26733.

A further aspect of the present invention is related to a pharmaceutical composition composition a comprising a sulfonamide derivative according to formula (I) and at least one further drug (in particular an anti-diabetes agent). In one embodiment the further diabetes agents are selected from the group comprising or consisting of insulin (or insulin mimicks), aldose reductase inhibitors, alpha-glucosidase inhibitors, sulfonyl urea agents, to biguanides (e.g. metformin), thiazolidines (e.g. pioglitizone, rosiglitazone, cf. WO 02/100396) or PPARs agonists or GSK-3 inhibitors.

Insulins useful with the method of the present invention include rapid acting insulins, intermediate acting insulins, long acting insulins and combination of intermediate and rapid acting insulins.

Aldose reductase inhibitors useful in the method of this invention include those known in the art. These include the non-limiting list of:

a) the spiro-isoquinoline-pyrrolidine tetrone compounds disclosed in U.S. Pat. No. 4,927,831 (Malamas), the contents of which are incorporated herein by reference, which includes ARI-509, also known as minalrestat or Spiro[isoquinoline-4(1H), 3'-pyrrolidine]-1,2',3,5'(2H)-tetrone, and analogs thereof.

b) 2-[(4-bromo-2-fluorophenyl)methyl]-6-fluoro-(9CI);

c) the compounds of U.S. Pat. No. 4,439,617, the contents of which are incorporated herein by reference, which includes Tolrestat, also known as Glycine, N-[[6-methoxy-5-(trifluoromethyl)-1-naphtalenyl]thioxomethyl]-N-methyl-(9CI) or AY-27773 and analogs thereof;

d) Sorbinil (Registra No. 68367-52-2) also known as Spiro [4H-1-benzopyman-4,4'-imidazole]-2',5'-dione, 6-fluoro-2,3-dihydro-, (4S)-(9CI) or CP 45634;

e) Methosorbinil;

f) Zopolrestat, which is 1-Phtalazineacetic acid, 3,44-dihydro-4-oxo-3-[[5-(trifluoromethyl)-2-benzothiazolyl]methyl]-(9CI) (Registry No. 110703-94-1);

g) Epalrestat, which is 3-Thiazolidineacetic acid, 5-[(2E)-2-methyl-3-phenyl-2-propenylidene]-4-oxo-2-thioxo-, (5Z)-(9CI) (Registry No. 82150-09-9);

h) Zenarestat (Registry No. 112733-40-6) or 3-[(4-bromo-2-fluorophenyl)-methyl]-7-chloro-3,4-dihydro-2,4-dioxo-1 (2H)-quinazoline acetic acid;

i) Imirestat; also known as 2,7-difluorospiro(9H-fluorene-9, 4'-imidazolidine)-2',5'-dione;

j) Ponalrestat (registry No. 72702-95-5), which is 1-Phtalazineacetic acid, 3-[(4-bromo-2-fluorophenyl)methyl]3,4-dihydro-4-oxo-(9CI) and also known as Stalil or Statyl;

k) ONO-2235, which is 3-Thiazolidineacetic acid, 5-[(2E)-2-methyl-3-phenyl-2-propenylidene-4-oxo-2-thioxo-, (5Z)-(9CI);

l) GP-1447, which is {3-[(4,5,7-trifluorobenzothiazol-2-yl) methyl]-5-methylphenylacetic acid};

m) CT-112, which is 5-(3-ethoxy-4-pentyloxyphenyl)-2,4-thiazolidinedione;

n) BAL-ARI 8, which is Glycine, N[(7-fluoro-9-oxo-9H-xanthen-2-yl)sulfonyl]-N-methyl-)9CI), Reg. No. 124066-40-6));

o) AD-5467, which is 2,3-dihydro-2,8-bis(1-methylethyl)-3-thioxox-4H-1,4-benzoxazine-4-acetic acid of the chloride salt form (4H-1,4-Benzoxazine-4-acetic acid, 2,3-dihydro-2,8-bis(1-methylethyl)-3-thioxo-(9CI);
p) ZD5522, which is (3',5'-dimethyl-4'-nitromethylsulfonyl-2-(2-tolyl)acetanilide);
q) 3,4-dihydro-2,8-diisopropyl-3-thioxo-2H-1,4-benzoxazine-4-acetic acid,
r) 1-[(3-bromo-2-benzofuranyl)sulfonyl]-2,4-imidazolidinedione (M-16209),
s) NZ-314, which is 1-Imidazolidineacetic acid, 3-[(3-nitrophenyl)methyl]-2,4,5-trioxo-9(CI) (Registry No. 128043-99-2),
t) 1-phtalazineacetic acid, 3,4-dihydro-4-oxo-3-[(5-trifluoromethyl)-2-benzothiazolyl]-methyl];
u) M-79175, which is Spiro[4H-1-benzopyran-4,4'-imidazolidine]-2',5'-dione; 6-fluoro-2,3-dihydro-2-methyl-, (2R, 4S)-(9CI);
v) SPR-210, which is 2H-1,4-Benzothiazine-2-acetic acid, 3,4-dihydro-3-oxo-4-[(4,5,7-trifluoro-2-benzothiazolyl) methyl]-(9CI);
w) Spiro[pyrrolidine-3,6'(5'H)-pyrrolo[1,2,3-de][1,4]benzoxazine]-2,5,5'-trione, 8'-chloro-2'-3'-dihydro-(9CI)(also known as AND 138 or 8-chloro-2',3'-dihydrospiro[pyrolizine-3,6'(5H)-pyrrolo-[1,2,3-de]-[1,4]benzoxazine]2,5,5'-trione);
x) 6-fluoro-2,3-dihydro-2',5'-dioxo-(2S-cis)-spiro[4H-1-benzopyran-4,4'-imidazolidine]-2-carboxamide (also known as SNK-860);

Among the more preferred aldose reductase inhibitors of this invention are minalrestat, Tolrestat, Sorbinil, Methosorbinil, Zopolrestat, Epalrestat, Zenarestat, Imirestat and Ponalrestat or the pharmaceutically acceptable salt forms thereof.

The alpha-glucosidase inhibitors useful for the method of the present invention include miglitol or acarbose, or the pharmaceutically acceptable salt form thereof.

Sulfonylurea agents useful with the method of the present invention include glipizide, Glyburide (Glibenclamide) Clorpropamide, Tolbutamide, Tolazamide and Glimepiride, or the pharmaceutically acceptable salt forms thereof.

Preferably, said supplementary pharmaceutically active agent is selected from the group consisting of a rapid acting insulin, an intermediate acting insulin, a long acting insulin, a combination of intermediate and rapid acting insulins, Inalrestat, Tolrestat, Sorbinil, Methosorbinil, Zopolrestat, Epalrestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, or SNK-860, Miglitol Acarbose, Glipizide, Glyburide, Chlorpropamide, Tolbutamide, Tolazamide, or Glimepriride.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the sulfonamide derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, intrathecal, intraperitoneal and intranasal. Depending on the intended route of delivery, the compounds are preferably formulated as either injectable, topical or oral compositions. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the sulfonamide compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the sulfonamide derivatives of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in Remington's Pharmaceutical Sciences.

Example 1

Preparation of a Pharmaceutical Formulation

The following formulation examples illustrate representative pharmaceutical compositions according to the present invention being not restricted thereto.

Formulation 1—Tablets

A sulfonamide compound of formula I is admixed as a dry powder with a dry gelatin binder in an approximate 1:2 weight ration. A minor amount of magnesium stearate is added as a lubricant The mixture is formed into 240-270 mg tablets (80-90 mg of active sulfonamide compound per tablet) in a tablet press.

Formulation 2—Capsules

A sulfonamide compound of formula I is admixed as a dry powder with a starch diluent in an approximate 1:1 weight ratio. The mixture is filled into 250 mg capsules (125 mg of active sulfonamide compound per capsule).

Formulation 3—Liquid

A sulfonamide compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A sulfonamide compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active sulfonamide compound) in a tablet press.

Formulation 5—Injection

A sulfonamide compound of formula I is dissolved in a buffered sterile saline injectable aqueous medium to a concentration of approximately 5 mg/ml.

Example 2

Biological Assay

In Vivo Assay in db/db Mice

The following assay aims at determining the anti-diabetic effect of the test compounds of formula (I) in a model of postprandial glycemia in db/db mice, in vivo.

The assay was performed as follows:

A total of 18 db/db mice (about 8-9 weeks; obtained from IFFACREDO, l'Arbreste, France) were fasted during 20 hours.

3 groups, each consisting of 6 animals were formed:
Group 1: The animals were administered (per os) a dose of 10 mg/kg of vehicle.
Group 2: The animals were administered (per os) a dose of 30 mg/kg of the test compound according to formula (I).
Group 3: The animals were administered (per os) a dose of 50 mg/kg of the test compound according to formula (I).

After oral administration of the compounds of formula (I) solubilized or suspended in CarboxyMethylCellulose (0.5%), Tween 20 (0.25%) and water as vehicle, the animals had access to commercial food (D04, UAR, Villemoisson/Orge, France) ad libitum. The diabetic state of the mice was verified by determining the blood glucose level before drug administration. Blood glucose and serum insulin levels were then determined 4 hrs after drug administration.

The determination of the blood glucose level was performed using a glucometer (Precision Q.I.D., Medisense, Abbot, ref. 212.62.31).

The determination of the Insulin level was performed using an ELISA kit (Crystal CHEM, Ref. INSK R020).

Changes in blood glucose and serum insulin of drug treated mice were expressed as a percentage of control (group 1: vehicle treated mice).

Treatment (per os) of the animals with test compounds of formula (I), at a dosage of 50 mg/kg, decreased the blood glucose level induced by food intake by about 20-45% and the blood insulin level by about 20-65% compared to the animals treated by the vehicle (Group 1).

For instance, upon using 4-chloro N-[(5-{[(butylamino) piperidin-1-yl]sulfonyl}thien-2-yl)methyl]benzamide as test compound (50 mg/kg, p.o.), a decrease of 42% in blood glucose level as well as a decrease of 61% in the insulin level was determined (compared to the animals treated by the vehicle (Group 1)).

REFERENCE LIST

1. Reaven et al (*American Journal of Medicine*, 60, 80 (1976);
2. Stout, *Metabolism*, 34, 7 (1985)
3. Diamanti-Kandarakis et al.; *European Journal of Endocrinology* 138, 269-274 (1998),
4. Andrea Dunaif; *Endocrine Reviews* 18(6), 774-800 (1997)).
5. WO 01/23378;
6. WO 02/28856;
7. WO 02/26733

The invention claimed is:

1. A method for treating type II diabetes, comprising:
    administering to a mammal in need of treatment an effective amount of at least one sulfonamide compound according to formula I to treat type II diabetes

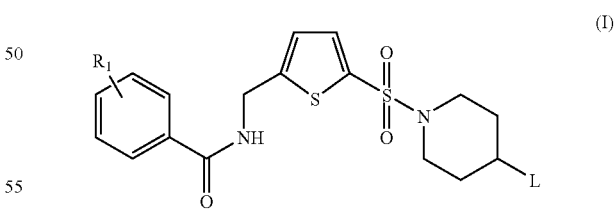

a geometrical isomer thereof, an optically active form as an enantiomer thereof, a diastereomer thereof, a racemate thereof, and a pharmaceutically acceptable salt thereof;
wherein $R^1$ is selected from the group consisting of hydrogen, $C_1$-$C_6$-alkoxy, $C_1$-$C_6$-alkyl, and halogen; and
L is $NHR^3$, wherein $R^3$ is a straight or branched $C_4$-$C_{12}$-alkyl, or a benzyl group.

2. The method as claimed in claim 1, wherein the sulfonamide derivative of formula (I) is administered to the mammal in combination with at least one supplementary drug selected from the group consisting of insulin, 2-[(4-bromo-2-fluorophenyl)methyl]-6-fluoro-(9CI); Glycine, N-[[6-methoxy-5-(trifluoromethyl)-1-naphtalenyl]thioxomethyl]-N-methyl-(9CI); Spiro[4H-1-benzopyran-4,4'-imidazoline]-2',5'-dione, 6-fluoro-2,3-dihydro-, (4S)-(9CI); Methosorbinil; 1-Phtalazineacetic acid, 3,44-dihydro-4-oxo-3-[[5-(trifluoromethyl)-2-benzothiazolyl]methyl]-(9CI); 3-Thiazolidineacetic acid, 5-[(2E)-2-methyl-3-phenyl-2-propenylidene]-4-oxo-2-thioxo-, (5Z)-(9CI); 3-[(4-bromo-2-fluorophenyl)-methyl]-7-chloro-3,4-dihydro-2,4-dioxo-1 (2H)-quinazoline acetic acid; 2,7-difluorospiro(9H-fluorene-9,4'-imidazolidine)-2',5'-dione; 1-Phtalazineacetic acid, 3-[(4-bromo-2-fluorophenyl)methyl]3,4-dihydro-4-oxo-(9CI); 3-Thiazolidineacetic acid, 5-[(2E)-2-methyl-3-phenyl-2-propenylidene]-4-oxo-2-thioxo-, (5Z)-(9CI); {3-[(4,5,7-trifluorobenzothiazol-2-yl)methyl]-5-methylphenylacetic acid}; 5-(3-ethoxy-4-pentyloxyphenyl)-2,4-thiazolidinedione; Glycine, N[(7-fluoro-9-oxo-9H-xanthen-2-yl)sulfonyl]-N-methyl-)9CI), Reg. No. 124066-40-6)); 2,3-dihydro-2,8-bis(1-methylethyl)-3-thioxox-4H-1,4-benzoxazine-4-acetic acid of the chloride salt form (4H-1,4-Benzoxazine-4-acetic acid, 2,3-dihydro-2,8-bis(1-methylethyl)-3-thioxo-(9CI); (3',5'-dimethyl-4'-nitromethylsulfonyl-2-(2-tolyl) acetanilide); 3,4-dihydro-2,8-diisopropyl-3-thioxo-2H-1,4-benzoxazine-4-acetic acid; 1-[(3-bromo-2-benzofuranyl) sulfonyl]-2,4-imidazolidinedione; 1-Imidazolidineacetic acid, 3-[(3-nitrophenyl)methyl]-2,4,5-trioxo-9(CI); 1-phtalazineacetic acid, 3,4-dihydro-4-oxo-3-[(5-trifluoromethyl)-2-benzothiazolyl]-methyl]; Spiro[4H-1-benzopyran-4,4'-imidazolidine]-2',5'-dione; 6-fluoro-2,3-dihydro-2-methyl-, (2R,4S)-(9CI); 2H-1,4-Benzothiazine-2-acetic acid, 3,4-dihydro-3-oxo-4-[(4,5,7-trifluoro-2-benzothiazolyl)methyl]-(9CI); Spiro[pyrrolidine-3,6'(5'H)-pyrrolo[1,2,3-de][1,4] benzoxazine]-2,5,5'-trione, 8'-chloro-2'-3'-dihydro-(9CI) (also known as AND 138 or 8-chloro-2',3'-dihydrospiro[pyrolizine-3,6'(5H)-pyrrolo-[1,2,3-de]-[1,4]benzoxazine]2,5, 5'-trione); 6-fluoro-2,3-dihydro-2',5'-dioxo-(2S-cis)-spiro [4H-1-benzopyran-4,4'-imidazolidine]-2-carboxamide;

miglitol or acarbose, or the pharmaceutically acceptable salt form thereof;

glipizide, Glyburide (Glibenclamide) Clorpropamide, Tolbutamide, Tolazamide and Glimepiride, and pharmaceutically acceptable salt forms thereof.

3. The method as claimed in claim 1, wherein the sulfonamide derivative of formula (I) is administered to the mammal in combination with at least one supplementary drug selected from the group consisting of a rapid acting insulin, an intermediate acting insulin, a long acting insulin, a combination of intermediate and rapid acting insulins, Minalrestat, Tolrestat, Sorbinil, Methosorbinil, Zopolrestat, Epalrestat, Zenarestat, Imirestat, Ponalrestat, ONO-2235, GP-1447, CT-112, BAL-AR1 8, AD-5467, ZD5522, M-16209, NZ-314, M-79175, SPR-210, ADN 138, SNK-860, Miglitol, Acarbose, Glipizide, Glyburide, Chlorpropamide, Tolbutamide, Tolazamide, and Glimepriride.

4. The method as claimed in claim 1, wherein the sulfonamide derivative of formula (I) is administered orally, rectally, transdermally, subcutaneously, intraveneously, intramuscularly, intrathecally, intraperiodontally, and intranasaly.

5. A method for treating type II diabetes, comprising:

administering to a mammal in need of treatment an effective amount of at least one sulfonamide compound selected from the group consisting of 4-chloro-N-[5-(piperazine-1-sulfonyl)-thiophen-2-yl-methyl]-benzamide;

4-Chloro-N-{5-[4-(3-trifluoromethanesulfonyl-phenylamino)-piperidine-1-sulfonyl]-thiophen-2-ylmethyl}-benzamide;

4-chloro-N-({5-[(4-pyridin-2-ylpiperazin-1-yl)sulfonyl] thien-2-yl}methyl)benzamide;

4-chloro-N-[(5-{[4-(4-fluorobenzoyl)piperidin-1-yl] sulfonyl}thien-2-yl)methyl]benzamide;

4-chloro-N-{5-({4-[4-(trifluoromethyl)phenyl]piperazin-1-yl}sulfonyl)thien-2-yl]methyl}benzamide;

4-chloro-N-({5-[(4-{2-nitrophenyl}piperazin-1-yl)sulfonyl]thien-2-yl}methyl)benzamide;

4-chloro-N-({5-[(4-{4-nitrophenyl}piperazin-1-yl)sulfonyl]thien-2-yl}methyl)benzamide;

4-chloro-N-[(5-{[4-(2-furoyl)piperazin-1-yl] sulfonyl}thien-2-yl)methyl]benzamide;

4-chloro-N-[(5-{[4-(4-hydroxyphenyl)piperazin-1-yl] sulfonyl}thien-2-yl)methyl]benzamide;

4-chloro-N-[(5-{[4-(2-oxo-2-pyrrolidin-1-ylethyl)piperazin-1-yl]sulfonyl}thien-2-yl)methyl]benzamide;

4-chloro-N-[(5-{[4-(2-morpholin-4-yl-2-oxoethyl)piperazin-1-yl]sulfonyl}thien-2-yl)methyl]benzamide;

4-chloro-N-[(5-{[4-(pyridin-4-ylmethyl)piperazin-1-yl] sulfonyl}thien-2-yl)methyl]benzamide;

4-chloro-N-[(5-{[4-(2-thien-2-ylethyl)piperazin-1-yl] sulfonyl}thien-2-yl)methyl]benzamide;

4-chloro-N-[(5-{[4-(3,5-dimethoxyphenyl)piperazin-1-yl]sulfonyl}thien-2-yl)methyl]benzamide;

4-chloro-N-[(5-{[4-(cyclohexylmethyl)piperazin-1-yl] sulfonyl}thien-2-yl)methyl]benzamide;

4-chloro-N-[(5-{[4-(2-methoxyphenyl)piperazin-1-yl] sulfonyl}thien-2-yl)methyl]benzamide;

N-({5-[(4-benzylpiperazin-1-yl)sulfonyl]thien-2-yl}methyl)-4-chlorobenzamide;

4-chloro-N-[(5-{[4-(2-phenylethyl)piperazin-1-yl] sulfonyl}thien-2-yl)methyl]benzamide;

4-chloro-N-[(5-{[4-(4-fluorobenzyl)piperazin-1-yl] sulfonyl}thien-2-yl)methyl]benzamide;

4-chloro-N-[(5-{[4-(2-cyanophenyl)piperazin-1-yl] sulfonyl}thien-2-yl)methyl]benzamide;

4-chloro-N-{5-({4-[4-chloro-3-(trifluoromethyl)phenyl] piperazin-1-yl}sulfonyl)thien-2-yl]methyl}benzamide;

4-chloro-N-[(5-{[4-(3-piperidin-1-ylpropyl)piperazin-1-yl]sulfonyl}thien-2-yl)methyl]benzamide;

4-chloro-N-({5-[(4-{4-chloro-2-nitrophenyl}piperazin-1-yl)sulfonyl]thien-2-yl}methyl)benzamide;

4-chloro-N-[(5-{[4-(6-methylpyridin-2-yl)piperazin-1-yl]sulfonyl}thien-2-yl)methyl]benzamide;

4-chloro-N-({5-[(4-hydroxy-4-phenylpiperidin-1-yl)sulfonyl]thien-2-yl}methyl)benzamide;

N-({5-[(4-benzoylpiperidin-1-yl)sulfonyl]thien-2-yl}methyl)-4-chlorobenzamide;

4-chloro-N-[(5-{[4-(2-oxo-2,3-dihydro-1H-benzimidazol-1-yl)piperidin-1-yl]sulfonyl}thien-2-yl)methyl] benzamide;

N-({5-[(4-benzylpiperidin-1-yl)sulfonyl]thien-2-yl}methyl)-4-chlorobenzamide;

4-chloro-N-({5-[(4-oxo-1-phenyl-1,3,8-triazaspiro[4,5] dec-8-yl)sulfonyl]thien-2-yl}methyl)benzamide;

4-chloro-N-{5-({4-[2-(methylanilino)-2-oxoethyl]piperazin-1-yl}sulfonyl)thien-2-yl]methyl}benzamide;

4-chloro-N-{5-({4-[hydroxy(diphenyl)methyl]piperidin-1-yl}sulfonyl)thien-2-yl]methyl}benzamide;

4-chloro-N-[(5-{[4-(3-cyanopyrazin-2-yl)piperazin-1-yl] sulfonyl}thien-2-yl)methyl]benzamide;

4-chloro-N-({5-[(4-{5-nitropyridin-2-yl}piperazin-1-yl) sulfonyl]thien-2-yl}methyl)benzamide;

4-chloro-N-{[5-({4-[3-chloro-5-(trifluoromethyl)pyridin-2-yl]piperazin-1-yl}sulfonyl)thien-2-yl]methyl}benzamide;
4-chloro-N-{[5-({4-[5-(trifluoromethyl)pyridin-2-yl]piperazin-1-yl}sulfonyl)thien-2-yl]methyl}benzamide;
4-chloro-N-{[5-({4-[3-(trifluoromethyl)pyridin-2-yl]piperazin-1-yl}sulfonyl)thien-2-yl]methyl}benzamide;
4-chloro-N-[(5-{[4-(2,4-difluorobenzoyl)piperidin-1-yl]sulfonyl}thien-2-yl)methyl]benzamide;
methyl 5-{4-[(5-{[(4-chlorobenzoyl)amino]methyl}thien-2-yl)sulfonyl]piperazin-1-yl}-7-(trifluoromethyl)thieno[3,2-b]pyridine-3-carboxylate;
ethyl 2-{4-[(5-{[(4-chlorobenzoyl)amino]methyl}thien-2-yl)sulfonyl]piperazin-1-yl}-5-cyano-6-methylnicotinate;
4-chloro-N-{[5-({4-[5-cyano-4,6-bis(dimethylamino)pyridin-2-yl]piperazin-1-yl}sulfonyl)thien-2-yl]methyl}benzamide;
4-chloro-N-{[5-({4-[6-methyl-2-(trifluoromethyl)quinolin-4-yl]piperazin-1-yl}sulfonyl)thien-2-yl]methyl}benzamide;
tert-butyl 4-[(5-{[(4-chlorobenzoyl)amino]methyl}thien-2-yl)sulfonyl]piperazine-1-carboxylate;
2-{4-[(5-{[(4-chlorobenzoyl)amino]methyl}thien-2-yl)sulfonyl]piperazin-1-yl}-8-ethyl-5-oxo-5,8-dihydropyrido[2,3-d]pyrimidine-6-carboxylic acid;
7-{4-[(5-{[(4-chlorobenzoyl)amino]methyl}thien-2-yl)sulfonyl]piperazin-1-yl}-1-ethyl-6-fluoro-4-oxo-1,4-dihydro[1,8]naphthyridine-3-carboxylic acid;
7-{4-[(5-{[(4-chlorobenzoyl)amino]methyl}thien-2-yl)sulfonyl]piperazin-1-yl}-1-ethyl-6-fluoro-4-oxo-1,4-dihydroquinoline-3-carboxylic acid;
4-chloro-N-[(5-{[4-(2,3-dihydro-1,4-benzodioxin-2-ylcarbonyl)piperazin-1-yl]sulfonyl}thien-2-yl)methyl]benzamide;
4-chloro-N-{[5-({4-[(2E)-3-phenylprop-2-enyl]piperazin-1-yl}sulfonyl)thien-2-yl]methyl}benzamide;
4-chloro-N-[(5-{[4-(3-phenylpropyl)piperazin-1-yl]sulfonyl}thien-2-yl)methyl]benzamide;
4-chloro-N-[(5-{[4-(3,4,5-trimethoxyphenyl)piperazin-1-yl]sulfonyl}thien-2-yl)methyl]benzamide;
N-[(5-{[4-(4-tert-butylbenzyl)piperazin-1-yl]sulfonyl}thien-2-yl)methyl]-4-chlorobenzamide;
4-chloro-N-[(5-{[4-(4-fluorophenyl)piperazin-1-yl]sulfonyl}thien-2-yl)methyl]benzamide;
4-chloro-N-[(5-{[4-(2-hydroxyphenyl)piperazin-1-yl]sulfonyl}thien-2-yl)methyl]benzamide;
4-chloro-N-{[5-({4-[4-(trifluoromethyl)pyridin-2-yl]piperazin-1-yl}sulfonyl)thien-2-yl]methyl}benzamide;
4-chloro-N-[(5-{[4-(5-cyanopyridin-2-yl)piperazin-1-yl]sulfonyl}thien-2-yl)methyl]benzamide;
tert-butyl 1-[(5-{[(4-chlorobenzoyl)amino]methyl}thien-2-yl)sulfonyl]piperidin-4-ylcarbamate;
4-chloro-N-({5-[(4-phenylpiperazin-1-yl)sulfonyl]thien-2-yl}methyl)benzamide;
4-chloro-N-{[5-(piperidin-1-ylsulfonyl)thien-2-yl]methyl}benzamide;
4-chloro-N-[(5-{[4-(1-naphthyl)piperazin-1-yl]sulfonyl}thien-2-yl)methyl]benzamide;
4-chloro-N-[(5-{[4-(3,4-dichlorophenyl)piperazin-1-yl]sulfonyl}thien-2-yl)methyl]benzamide;
4-chloro-N-{[5-({4-[3-(trifluoromethyl)phenyl]piperazin-1-yl}sulfonyl)thien-2-yl]methyl}benzamide;
4-chloro-N-{[5-({3-hydroxy-4-[3-(trifluoromethyl)phenyl]piperidin-1-yl}sulfonyl)thien-2-yl]methyl}benzamide;
4-chloro-N-[(5-{[4-(2-methylphenyl)piperazin-1-yl]sulfonyl}thien-2-yl)methyl]benzamide;
N-[(5-{[(1R,4R)-5-benzyl-2,5-diazabicyclo[2.2.1]hept-2-yl]sulfonyl}thien-2-yl)methyl]-4-chlorobenzamide;
N-[(5-{[4-(benzyloxy)piperidin-1-yl]sulfonyl}thien-2-yl)methyl]-4-chlorobenzamide;
4-chloro-N-[(5-{[4-(2-chlorodibenzo[b,f][1,4]oxazepin-11-yl)piperazin-1-yl]sulfonyl}thien-2-yl)methyl]benzamide;
N-(4-chlorophenyl)-2-(5-{[4-(2-oxo-2,3-dihydro-1H-benzimidazol-1-yl)piperidin-1-yl]sulfonyl}thien-2-yl)acetamide;
4-chloro-N-({5-[(4-hydroxypiperidin-1-yl)sulfonyl]thien-2-yl}methyl)benzamide;
N-[(5-{[4-(4-acetylphenyl)piperazin-1-yl]sulfonyl}thien-2-yl)methyl]-4-chlorobenzamide;
4-chloro-N-[(5-{[4-(3,5-dichloropyridin-4-yl)piperazin-1-yl]sulfonyl}thien-2-yl)methyl]benzamide;
4-chloro-N-[(5-{[4-(3-methoxyphenyl)piperazin-1-yl]sulfonyl}thien-2-yl)methyl]benzamide;
N-({5-[(4-benzyl-4-hydroxypiperidin-1-yl)sulfonyl]thien-2-yl}methyl)-4-chlorobenzamide;
N-{[5-({4-[(2-tert-butyl-1H-indol-5-yl)amino]piperidin-1-yl}sulfonyl)thien-2-yl]methyl}-4-chlorobenzamide
4-chloro-N-{[5-({4-[(phenylacetyl)amino]piperidin-1-yl}sulfonyl)thien-2-yl]methyl}benzamide;
4-chloro-N-[(5-{[4-(tetrahydrofuran-2-ylcarbonyl)piperazin-1-yl]sulfonyl}thien-2-yl)methyl]benzamide;
4-chloro-N-[(5-{[4-(6-chloropyridin-2-yl)piperazin-1-yl]sulfonyl}thien-2-yl)methyl]benzamide;
4-chloro-N-[(5-{[4-(4-chlorophenyl)piperazin-1-yl]sulfonyl}thien-2-yl)methyl]benzamide;
N-[(5-{[4-(2H-1,2,3-benzotriazol-2-yl)piperidin-1-yl]sulfonyl}thien-2-yl)methyl]-4-chlorobenzamide;
4-chloro-N-[(5-{[4-(4-chlorobenzoyl)piperidin-1-yl]sulfonyl}thien-2-yl)methyl]benzamide;
4-chloro-N-({5-[(4-phenoxypiperidin-1-yl)sulfonyl]thien-2-yl}methyl)benzamide;
N-{[5-({4-[benzyl(methyl)amino]piperidin-1-yl}sulfonyl)thien-2-yl]methyl}-4-chlorobenzamide;
4-chloro-N-{[5-({4-[3-(2,4-dichlorophenyl)-1H-pyrazol-5-yl]piperidin-1-yl}sulfonyl)thien-2-yl]methyl}benzamide;
4-chloro-N-[(5-{[4-(5-thien-2-yl-1H-pyrazol-3-yl)piperidin-1-yl]sulfonyl}thien-2-yl)methyl]benzamide;
4-chloro-N-[(5-{[4-(2,3,4,5,6-pentamethylbenzoyl)piperidin-1-yl]sulfonyl}thien-2-yl)methyl]benzamide;
4-chloro-N-[(5-{[4-(phenylacetyl)-1,4-diazepan-1-yl]sulfonyl}thien-2-yl)methyl]benzamide;
4-chloro-N-{[5-({4-[5-(4-methoxyphenyl)-1H-pyrazol-3-yl]piperidin-1-yl}sulfonyl}thien-2-yl]methyl benzamide
N-({5-[(4-anilinopiperidin-1-yl)sulfonyl]thien-2-yl}methyl)-4-chlorobenzamide;
4-chloro-N-[(5-{[4-(3-phenyl-1,2,4-thiadiazol-5-yl)piperazin-1-yl]sulfonyl}thien-2-yl)methyl]benzamide;
4-chloro-N-[(5-{[4-(2-phenylethyl)piperidin-1-yl]sulfonyl}thien-2-yl)methyl]benzamide;
4-chloro-N-({5-[(4-heptylpiperazin-1-yl)sulfonyl]thien-2-yl}methyl)benzamide;
4-chloro-N-({5-[(4-octylpiperazin-1-yl)sulfonyl]thien-2-yl}methyl)benzamide;
N-[(5-{[4-(1H-1,2,3-benzotriazol-1-yl)piperidin-1-yl]sulfonyl}thien-2-yl)methyl]-4-chlorobenzamide;
2-(5-{[4-(1H-1,2,3-benzotriazol-1-yl)piperidin-1-yl]sulfonyl}thien-2-yl)-N-(4-chlorophenyl)acetamide;

2-{1-[(5-{[(4-chlorobenzoyl)amino]methyl}thien-2-yl)
sulfonyl]piperidin-4-yl}-2H-1,2,3-benzotriazole-5-carboxylic acid;
4-chloro-N-[(5-{[4-(5-chloro-1H-1,2,3-benzotriazol-1-yl)piperidin-1-yl]sulfonyl}thien-2-yl)methyl]benzamide;
methyl 1-{1-[(5-{[(4-chlorobenzoyl)amino]methyl}thien-2-yl)sulfonyl]piperidin-4-yl}-1H-1,2,3-benzotriazole-5-carboxylate;
methyl 1-{1-[(5-{[(4-chlorobenzoyl)amino]methyl}thien-2-yl)sulfonyl]piperidin-4-yl}-1H-1,2,3-benzotriazole-6-carboxylate;
methyl 2-{1-[(5-{[(4-chlorobenzoyl)amino]methyl}thien-2-yl)sulfonyl]piperidin-4-yl}-2H-1,2,3-benzotriazole-5-carboxylate;
4-chloro-N-[(5-{[4-(6-chloro-1H-1,2,3-benzotriazol-1-yl)piperidin-1-yl]sulfonyl}thien-2-yl)methyl]benzamide;
4-chloro-N-{[5-({4-[5-(trifluoromethyl)-1H-1,2,3-benzotriazol-1-yl]piperidin-1-yl}sulfonyl)thien-2-yl]methyl}benzamide;
N-[(5-{[4-(7-aza-1H-benzimidazol-1-yl)piperidin-1-yl]sulfonyl}thien-2-yl)methyl]-4-chlorobenzamide;
1-{1-[(5-{[(4-chlorobenzoyl)amino]methyl}thien-2-yl)sulfonyl]piperidin-4-yl}-1H-1,2,3-benzotriazole-5-carboxylic acid;
1-{1-[(5-{[(4-chlorobenzoyl)amino]methyl}thien-2-yl)sulfonyl]piperidin-4-yl}-1H-1,2,3-benzotriazole-6-carboxylic acid;
N-[(5-{[4-(2-amino-9H-purin-9-yl)piperidin-1-yl]sulfonyl}thien-2-yl)methyl]-4-chlorobenzamide;
4-chloro-N-[(5-{[4-(9H-purin-9-yl)piperidin-1-yl]sulfonyl}thien-2-yl)methyl]benzamide;
N-[(5-{[4-(6-amino-9H-purin-9-yl)piperidin-1-yl]sulfonyl}thien-2-yl)methyl]-4-chlorobenzamide;
4-chloro-N-({5-[(4-{6-nitro-1H-benzimidazol-1-yl}piperidin-1-yl)sulfonyl]thien-2-yl}methyl)benzamide;
4-chloro-N-({5-[(4-{5-nitro-1H-benzimidazol-1-yl}piperidin-1-yl)sulfonyl]thien-2-yl}methyl)benzamide;
4-chloro-N-[(5-{[4-(2H-1,2,3-triazol-2-yl)piperidin-1-yl]sulfonyl}thien-2-yl)methyl]benzamide;
N-[(5-{[4-(1H-benzimidazol-1-yl)piperidin-1-yl]sulfonyl}thien-2-yl)methyl]-4-chlorobenzamide;
4-chloro-N-{[5-({4-[3-propylanilino]piperidin-1-yl}sulfonyl)thien-2-yl]methyl}benzamide;
4-chloro-N-{[5-({4-[3-(trifluoromethyl)anilino]piperidin-1-yl}sulfonyl)thien-2-yl]methyl}benzamide;
4-chloro-N-{[5-({4-[3-(dimethylamino)anilino]piperidin-1-yl}sulfonyl)thien-2-yl]methyl}benzamide;
methyl 3-({1-[(5-{[(4-chlorobenzoyl)amino]methyl}thien-2-yl)sulfonyl]-piperidin-4-yl}amino)-benzoate;
4-chloro-N-{[5-({4-[3-(methylsulfanyl)anilino]piperidin-1-yl}sulfonyl)thien-2-yl]methyl}benzamide;
4-chloro-N-({5-[(4-{3-nitroanilino}piperidin-1-yl)sulfonyl]thien-2-yl}methyl)benzamide;
4-chloro-N-[(5-{[4-(2-methoxyanilino)piperidin-1-yl]sulfonyl}thien-2-yl)methyl]benzamide;
3-({1-[(5-{[(4-chlorobenzoyl)amino]methyl}thien-2-yl)sulfonyl]piperidin-4-yl}amino)benzoate;
4-chloro-N-{[5-({4-[2-(trifluoromethyl)anilino]piperidin-1-yl}sulfonyl)thien-2-yl]methyl}benzamide;
4-chloro-N-({5-[(4-{2-nitro-4-[(trifluoromethyl)sulfonyl]anilino}piperidin-1-yl)sulfonyl]thien-2-yl}methyl)benzamide;

4-chloro-N-[(5-{[4-(4-chloroanilino)piperidin-1-yl]sulfonyl}thien-2-yl)methyl]benzamide;
4-chloro-N-{[5-({4-[4-(trifluoromethyl)anilino]piperidin-1-yl}sulfonyl)thien-2-yl]methyl}benzamide
4-chloro-N-({5-[(4-{4-[(trifluoromethyl)sulfonyl]anilino}piperidin-1-yl)sulfonyl]thien-2-yl}methyl)benzamide;
4-chloro-N-({5-[(4-{2-nitroanilino}piperidin-1-yl)sulfonyl]thien-2-yl}methyl)benzamide;
N-{[5-({4-[4-(aminocarbonyl)anilino]piperidin-1-yl}sulfonyl)thien-2-yl]methyl}-4-chlorobenzamide;
4-chloro-N-{[5-({4-[4-(1,3-dithiolan-2-yl)anilino]piperidin-1-yl}sulfonyl)thien-2-yl]methyl}benzamide;
N-[(5-{[4-(3-chloroanilino)piperidin-1-yl]sulfonyl}thien-2-yl)methyl]-3-nitrobenzamide;
4-chloro-N-[(5-{[4-(3-chloroanilino)piperidin-1-yl]sulfonyl}thien-2-yl)methyl]benzamide;
4-chloro-N-[(5-{[4-(3-methoxyanilino)piperidin-1-yl]sulfonyl}thien-2-yl)methyl]benzamide;
4-chloro-N-{[5-({4-1,3-(methylsulfonyl)anilino]piperidin-1-yl}sulfonyl)thien-2-yl]methyl}benzamide;
N-({5-[(4-{3-[amino(imino)methyl]anilino}piperidin-1-yl)sulfonyl]thien-2-yl}methyl)-4-chlorobenzamide;
4-chloro-N-({5-[(4-{3-[(2-hydroxyethyl)sulfonyl]anilino}piperidin-1-yl)sulfonyl]thien-2-yl}methyl)benzamide;
N-[(5-{[4-(2-aminoanilino)piperidin-1-yl]sulfonyl}thien-2-yl)methyl]-4-chlorobenzamide;
4-chloro-N-[(5-{[4-(2-hydroxyanilino)piperidin-1-yl]sulfonyl}thien-2-yl)methyl]benzamide;
4-chloro-N-[(5-{[4-(4-hydroxyanilino)piperidin-1-yl]sulfonyl}thien-2-yl)methyl]benzamide;
4-chloro-N-({5-[(4-{3-[(trifluoromethyl)sulfanyl]anilino}piperidin-1-yl)sulfonyl]thien-2-yl}methyl)benzamide;
4-chloro-N-[(5-{[4-(3-toluidino)piperidin-1-yl]sulfonyl}thien-2-yl)methyl]benzamide;
4-chloro-N-({5-[(4-{[3-chloro-5-(trifluoromethyl)pyridin-2-yl]amino}piperidin-1-yl)sulfonyl]thien-2-yl}methyl)benzamide;
4-chloro-N-{[5-({4-[3-(1,3-oxazol-5-yl)anilino]piperidin-1-yl}sulfonyl)thien-2-yl]methyl}benzamide;
N-[(5-{[4-(3-tert-butylanilino)piperidin-1-yl]sulfonyl}thien-2-yl)methyl]-4-chlorobenzamide;
4-chloro-N-[(5-{[4-(2-propylanilino)piperidin-1-yl]sulfonyl}thien-2-yl)methyl]benzamide;
4-chloro-N-{[5-({4-[(2,2-dioxido-1,3-dihydro-2-benzothien-5-yl)amino]piperidin-1-yl}sulfonyl)thien-2-yl]methyl}benzamide;
4-chloro-N-[(5-{[4-(2,3-dihydro-1H-inden-5-ylamino)piperidin-1-yl]sulfonyl}thien-2-yl)methyl]benzamide;
4-chloro-N-[(5-{[4-(4-propylanilino)piperidin-1-yl]sulfonyl}thien-2-yl)methyl]benzamide;
4-chloro-N-[(5-{[4-({3-nitropyridin-2-yl}amino)piperidin-1-yl]sulfonyl}thien-2-yl)methyl]benzamide;
N-{[5-({4-[(3-aminopyridin-2-yl)amino]piperidin-1-yl}sulfonyl)thien-2-yl]methyl}-4-chlorobenzamide;
N-[(5-{[4-([1,1'-biphenyl]-3-ylamino)piperidin-1-yl]sulfonyl}thien-2-yl)methyl]-4-chlorobenzamide;
N-[(5-{[4-(3-benzylanilino)piperidin-1-yl]sulfonyl}thien-2-yl)methyl]-4-chlorobenzamide;
4-chloro-N-[(5-{[4-(pyrimidin-2-ylamino)piperidin-1-yl]sulfonyl}thien-2-yl)methyl]benzamide;
4-chloro-N-{[5-({4-[4-(morpholin-4-ylsulfonyl)anilino]piperidin-1-yl}sulfonyl)thien-2-yl]methyl}benzamide;

4-chloro-N-({5-[(4-{[4-(trifluoromethyl)pyrimidin-2-yl]amino}piperidin-1-yl)sulfonyl]thien-2-yl}methyl)benzamide;
4-chloro-N-[(5-{[4-(3-cyclohexyl-4-hydroxyanilino)piperidin-1-yl]sulfonyl-4-thien-2-yl)methyl]benzamide;
N-({5-[(4-{3-[(butylamino)sulfonyl]anilino}piperidin-1-yl)sulfonyl]thien-2-yl}methyl)-4-chlorobenzamide;
4-chloro-N-[(5-{[4-(3-ethylanilino)piperidin-1-yl]sulfonyl}thien-2-yl)methyl]benzamide;
4-chloro-N-[(5-{[4-(5,6,7,8-tetrahydronaphthalen-1-ylamino)piperidin-1-yl]sulfonyl}thien-2-yl)methyl]benzamide;
N-{[5-({4-[3-(aminosulfonyl)anilino]piperidin-1-yl}sulfonyl)thien-2-yl]methyl}-4-chlorobenzamide;
4-chloro-N-[(5-{[4-(quinolin-5-ylamino)piperidin-1-yl]sulfonyl}thien-2-yl)methyl]benzamide;
4-chloro-N-[(5-{[4-(quinolin-8-ylamino)piperidin-1-yl]sulfonyl}thien-2-yl)methyl]benzamide;
4-Chloro-N-[(5-{[4-(3-propylphenoxy)piperidin-1-yl]sulfonyl}thien-2-yl)methyl]benzamide;
4-chloro-N-{[5-({4-[(2E)-3-phenylprop-2-enoyl]piperazin-1-yl}sulfonyl)thien-2-yl]methyl}benzamide;
4-chloro-N-({5-[(4-{4-nitrobenzoyl}piperazin-1-yl)sulfonyl]thien-2-yl}methyl)benzamide;
N-({5-[(4-benzoylpiperazin-1-yl)sulfonyl]thien-2-yl}methyl)-4-chlorobenzamide;
4-chloro-N-{[5-({4-[4-(trifluoromethyl)benzoyl]piperazin-1-yl}sulfonyl)thien-2-yl]methyl}benzamide;
4-chloro-N-{[5-({4-[4-(dimethylamino)benzoyl]piperazin-1-yl}sulfonyl)thien-2-yl]methyl}benzamide;
4-chloro-N-[(5-{[4-(2-fluorobenzoyl)piperazin-1-yl]sulfonyl}thien-2-yl)methyl]benzamide;
4-chloro-N-[(5-{[4-(2,6-difluorobenzoyl)piperazin-1-yl]sulfonyl}thien-2-yl)methyl]benzamide;
4-chloro-N-[(5-{[4-(3-fluorobenzoyl)piperazin-1-yl]sulfonyl}thien-2-yl)methyl]benzamide;
4-chloro-N-[(5-{[4-(2-naphthoyl)piperazin-1-yl]sulfonyl}thien-2-yl)methyl]benzamide;
4-chloro-N-[(5-{[4-(1-naphthoyl)piperazin-1-yl]sulfonyl}thien-2-yl)methyl]benzamide;
4-chloro-N-({5-[(4-{2-nitrobenzoyl}piperazin-1-yl)sulfonyl]thien-2-yl}methyl)benzamide;
4-chloro-N-[(5-{[4-(pyridin-3-ylcarbonyl)piperazin-1-yl]sulfonyl}thien-2-yl)methyl]benzamide;
N-[(5-{[4-(2,1,3-benzoxadiazol-5-ylcarbonyl)piperazin-1-yl]sulfonyl}thien-2-yl)methyl]-4-chlorobenzamide;
4-chloro-N-[(5-{[4-(2,4-difluorobenzoyl)piperazin-1-yl]sulfonyl}thien-2-yl)methyl]benzamide;
4-chloro-N-[(5-{[4-(2,4,6-trifluorobenzoyl)piperazin-1-yl]sulfonyl}thien-2-yl)methyl]benzamide;
4-chloro-N-[(5-{[4-(2,6-dichlorobenzoyl)piperazin-1-yl]sulfonyl}thien-2-yl)methyl]benzamide;
4-chloro-N-({5-[(4-heptanoylpiperazin-1-yl)sulfonyl]thien-2-yl}methyl)benzamide;
4-chloro-N-[(5-{[4-(quinolin-8-ylsulfonyl)piperazin-1-yl]sulfonyl}thien-2-yl)methyl]benzamide;
4-nitro-N-({5-[(4-{3-[(trifluoromethyl)sulfonyl]anilino}piperidin-1-yl)sulfonyl]thien-2-yl}methyl)benzamide;
N-[(5-{[4-(1H-1,2,3-benzotriazol-1-yl)piperidin-1-yl]sulfonyl}thien-2-yl)methyl]-3-nitrobenzamide;
4-nitro-N-({5-[(4-{3-[(trifluoromethyl)sulfonyl]anilino}piperidin-1-yl)sulfonyl]thien-2-yl}methyl)benzamide;
N-[(5-{[4-(2,4-difluorobenzoyl)piperidin-1-yl]sulfonyl}thien-2-yl)methyl]-4-nitrobenzamide;
N-[(5-{[4-(1H-1,2,3-benzotriazol-1-yl)piperidin-1-yl]sulfonyl}thien-2-yl)methyl]-4-nitrobenzamide;
N-[(5-{[4-(1H-1,2,3-benzotriazol-1-yl)piperidin-1-yl]sulfonyl}thien-2-yl)methyl]-3-nitrobenzamide;
4-nitro-N-({5-[(4-{3-[(trifluoromethyl)sulfonyl]anilino}piperidin-1-yl)sulfonyl]thien-2-yl}methyl)benzamide;
N-[(5-{[4-(2,4-difluorobenzoyl)piperidin-1-yl]sulfonyl}thien-2-yl)methyl]-4-nitrobenzamide;
N-[(5-{[4-(1H-1,2,3-benzotriazol-1-yl)piperidin-1-yl]sulfonyl}thien-2-yl)methyl]-4-nitrobenzamide;
3-nitro-N-[(5-{[4-(3-methoxyanilino)piperidin-1-yl]sulfonyl}thien-2-yl)methyl]benzamide;
3-nitro-N-{[5-({4-[3-(trifluoromethyl)anilino]piperidin-1-yl}sulfonyl)thien-2-yl]methyl}benzamide;
N-{[5-({4-[3-(dimethylamino)anilino]piperidin-1-yl}sulfonyl)thien-2-yl]methyl}-3-nitrobenzamide;
3-nitro-N-{[5-({4-[3-(methylsulfonyl)anilino]piperidin-1-yl}sulfonyl)thien-2-yl]methyl}benzamide;
3-nitro-N-{[5-({4-[3-(methylsulfanyl)anilino]piperidin-1-yl}sulfonyl)thien-2-yl]methyl}benzamide;
N-{[5-({4-[3-(aminosulfonyl)anilino]piperidin-1-yl}sulfonyl)thien-2-yl]methyl}-3-nitrobenzamide;
methyl 3-{[1-({5-[({3-nitrobenzoyl}amino)methyl]-thien-2-yl}sulfonyl)-piperidin-4-yl]amino}benzoate;
N-{[5-({4-[3-(aminocarbonyl)anilino]piperidin-1-yl}sulfonyl)thien-2-yl]methyl}-3-nitrobenzamide;
3-nitro-N-({5-[(4-{3-nitroanilino}piperidin-1-yl)sulfonyl]thien-2-yl}methyl)benzamide;
3-nitro-N-[(5-{[4-(2-methoxyanilino)piperidin-1-yl]sulfonyl}thien-2-yl)methyl]benzamide;
3-nitro-N-{[5-({4-[2-(trifluoromethyl)anilino]piperidin-1-yl}sulfonyl)thien-2-yl]methyl}benzamide;
3-nitro-N-({5-[(4-{2-nitroanilino}piperidin-1-yl)sulfonyl]thien-2-yl}methyl)benzamide;
N-[(5-{[4-(4-chloroanilino)piperidin-1-yl]sulfonyl}thien-2-yl)methyl]-3-nitrobenzamide;
3-nitro-N-{[5-({4-[4-(trifluoromethyl)anilino]piperidin-1-yl}sulfonyl)thien-2-yl]methyl}benzamide;
3-nitro-N-({5-[(4-{4-[(trifluoromethyl)sulfonyl]anilino}piperidin-1-yl)sulfonyl]thien-2-yl}methyl)benzamide;
N-{[5-({4-[4-(aminocarbonyl)anilino]piperidin-1-yl}sulfonyl)thien-2-yl]methyl}-3-nitrobenzamide;
N-[(5-{[4-(3-propylanilino)piperidin-1-yl]sulfonyl}thien-2-yl)methyl]-3-nitrobenzamide;
N-[(5-{[4-(3-chloroanilino)piperidin-1-yl]sulfonyl}thien-2-yl)methyl]-4-nitrobenzamide;
4-nitro-N-[(5-{[4-(3-methoxyanilino)piperidin-1-yl]sulfonyl}thien-2-yl)methyl]benzamide;
4-nitro-N-{[5-({4-[3-(trifluoromethyl)anilino]piperidin-1-yl}sulfonyl)thien-2-yl]methyl}benzamide;
N-{[5-({4-[3-(dimethylamino)anilino]piperidin-1-yl}sulfonyl)thien-2-yl]methyl}-4-nitrobenzamide;
4-nitro-N-[(5-{[4-(3-propylanilino)piperidin-1-yl]sulfonyl}thien-2-yl)methyl]benzamide;
4-nitro-N-{[5-({4-[3-(methylsulfonyl)anilino]piperidin-1-yl}sulfonyl)thien-2-yl]methyl}benzamide;
4-nitro-N-{[5-({4-[3-(methylsulfanyl)anilino]piperidin-1-yl}sulfonyl)thien-2-yl]methyl}benzamide;
N-{[5-({4-[3-(aminosulfonyl)anilino]piperidin-1-yl}sulfonyl)thien-2-yl]methyl}-4-nitrobenzamide;
3-{[1-({5-[({4-nitrobenzoyl}amino)methyl]thien-2-yl}sulfonyl)piperidin-4-yl]amino}benzamide;
3-{[1-({5-[({4-nitrobenzoyl}amino)methyl]thien-2-yl}sulfonyl)piperidin-4-yl]amino}benzamide;

4-nitro-N-({5-[(4-{3-nitroanilino}piperidin-1-yl)sulfonyl]thien-2-yl}methyl)benzamide;
4-nitro-N-[(5-{[4-(2-methoxyanilino)piperidin-1-yl]sulfonyl}thien-2-yl)methyl]benzamide;
4-nitro-N-{[5-({4-[2-(trifluoromethyl)anilino]piperidin-1-yl}sulfonyl)thien-2-yl]methyl}benzamide;
4-nitro-N-({5-[(4-{2-nitroanilino}piperidin-1-yl)sulfonyl]thien-2-yl}methyl)benzamide;
N-[(5-{[4-(4-chloroanilino)piperidin-1-yl]sulfonyl}thien-2-yl)methyl]-4-nitrobenzamide;
4-nitro-N-{[5-({4-[4-(trifluoromethyl)anilino]piperidin-1-yl}sulfonyl)thien-2-yl]methyl}benzamide;
4-nitro-N-({5-[(4-{4-[(trifluoromethyl)sulfonyl]anilino}piperidin-1-yl)sulfonyl]thien-2-yl}methyl)benzamide;
N-{[5-({4-[4-(aminocarbonyl)anilino]piperidin-1-yl}sulfonyl)thien-2-yl]methyl}-4-nitrobenzamide;
N-{[5-({4-[4-(1,3-dithiolan-2-yl)anilino]piperidin-1-yl}sulfonyl)thien-2-yl]methyl}-4-nitrobenzamide;
N-({5-[(4-{3-[amino(imino)methyl]anilino}piperidin-1-yl)sulfonyl]thien-2-yl}methyl)-3-nitrobenzamide;
N-({5-[(4-{3-[(2-hydroxyethyl)sulfonyl]anilino}piperidin-1-yl)sulfonyl]thien-2-yl}methyl)-3-nitrobenzamide;
N-({5-[(4-anilinopiperidin-1-yl)sulfonyl]thien-2-yl}methyl)-3-nitrobenzamide;
N-({5-[(4-{3-[(2-hydroxyethyl)sulfonyl]anilino}piperidin-1-yl)sulfonyl]thien-2-yl}methyl)-4-nitrobenzamide;
N-({5-[(4-anilinopiperidin-1-yl)sulfonyl]thien-2-yl}methyl)-4-nitrobenzamide;
N-({5-[(4-{3-[amino(imino)methyl]anilino}piperidin-1-yl)sulfonyl]thien-2-yl}methyl)-4-nitrobenzamide;
3-nitro-N-({5-[(4-{3-[(trifluoromethyl)sulfanyl]anilino}piperidin-1-yl)sulfonyl]thien-2-yl}methyl)benzamide;
4-nitro-N-({5-[(4-{3-[(trifluoromethyl)sulfanyl]anilino}piperidin-1-yl)sulfonyl]thien-2-yl}methyl)benzamide;
3-nitro-N-[(5-{[4-({3-nitropyridin-2-yl}amino)piperidin-1-yl]sulfonyl}thien-2-yl)methyl]benzamide;
N-{[5-({4-[(2,2-dioxido-1,3-dihydro-2-benzothien-5-yl)amino]piperidin-1-yl}sulfonyl)thien-2-yl]methyl}-3-nitrobenzamide;
N-[(5-{[4-(2,3-dihydro-1H-inden-5-ylamino)piperidin-1-yl]sulfonyl}thien-2-yl)methyl]-3-nitrobenzamide;
3-nitro-N-[(5-{[4-(2-propylanilino)piperidin-1-yl]sulfonyl}thien-2-yl)methyl]benzamide;
3-nitro-N-[(5-{[4-(4-propylanilino)piperidin-1-yl]sulfonyl}thien-2-yl)methyl]benzamide;
N-[(5-{[4-(3-tert-butylanilino)piperidin-1-yl]sulfonyl}thien-2-yl)methyl]-3-nitrobenzamide;
3-nitro-N-{[5-({4-[3-(1,3-oxazol-5-yl)anilino]piperidin-1-yl}sulfonyl)thien-2-yl]methyl}benzamide;
3-nitro-N-[(5-{[4-(2-phenylethyl)piperidin-1-yl]sulfonyl}thien-2-yl)methyl]benzamide;
N-({5-[(4-{[3-chloro-5-(trifluoromethyl)pyridin-2-yl]amino}piperidin-1-yl)sulfonyl]thien-2-yl}methyl)-3-nitrobenzamide;
N-[(5-{[4-([1,1'-biphenyl]-3-ylamino)piperidin-1-yl]sulfonyl}thien-2-yl)methyl]-3-nitrobenzamide;
N-[(5-{[4-(3-benzylanilino)piperidin-1-yl]sulfonyl}thien-2-yl)methyl]-3-nitrobenzamide;
3-nitro-N-{[5-({4-[3-(morpholin-4-ylsulfonyl)anilino]piperidin-1-yl}sulfonyl)thien-2-yl]methyl}benzamide;
3-nitro-N-[(5-{[4-(3-propylphenoxy)piperidin-1-yl]sulfonyl}thien-2-yl)methyl]benzamide;

4-nitro-N-[(5-{[4-(pyrimidin-2-ylamino)piperidin-1-yl]sulfonyl}thien-2-yl)methyl]benzamide;
N-{[5-({4-[(3-aminopyridin-2-yl)amino]piperidin-1-yl}sulfonyl)thien-2-yl]methyl}-4-nitrobenzamide;
4-nitro-N-[(5-{[4-({3-nitropyridin-2-yl}amino)piperidin-1-yl]sulfonyl}thien-2-yl)methyl]benzamide;
N-[(5-{[4-(2,3-dihydro-1H-inden-5-ylamino)piperidin-1-yl]sulfonyl}thien-2-yl)methyl]-4-nitrobenzamide;
4-nitro-N-[(5-{[4-(2-propylanilino)piperidin-1-yl]sulfonyl}thien-2-yl)methyl]benzamide;
4-nitro-N-[(5-{[4-(4-propylanilino)piperidin-1-yl]sulfonyl}thien-2-yl)methyl]benzamide;
N-[(5-{[4-(3-tert-butylanilino)piperidin-1-yl]sulfonyl}thien-2-yl)methyl]-4-nitrobenzamide;
4-nitro-N-{[5-({4-[3-(1,3-oxazol-5-yl)anilino]piperidin-1-yl}sulfonyl)thien-2-yl]methyl}benzamide;
4-nitro-N-[(5-{[4-(2-phenylethyl)piperidin-1-yl]sulfonyl}thien-2-yl)methyl]benzamide;
N-({5-[(4-{[3-chloro-5-(trifluoromethyl)pyridin-2-yl]amino}piperidin-1-yl)sulfonyl]thien-2-yl}methyl)-4-nitrobenzamide;
N-[(5-{[4-([1,1'-biphenyl]-3-ylamino)piperidin-1-yl]sulfonyl}thien-2-yl)methyl]-4-nitrobenzamide;
N-[(5-{[4-(3-benzylanilino)piperidin-1-yl]sulfonyl}thien-2-yl)methyl]-4-nitrobenzamide;
4-nitro-N-{[5-({4-[3-(morpholin-4-ylsulfonyl)anilino]piperidin-1-yl}sulfonyl)thien-2-yl]methyl}benzamide;
N-[(5-{[4-(2-aminoanilino)piperidin-1-yl]sulfonyl}thien-2-yl)methyl]-3-nitrobenzamide;
3-nitro-N-[(5-{[4-(pyrimidin-2-ylamino)piperidin-1-yl]sulfonyl}thien-2-yl)methyl]benzamide;
N-{[5-({4-[(3-aminopyridin-2-yl)amino]piperidin-1-yl}sulfonyl)thien-2-yl]methyl}-3-nitrobenzamide;
N-({5-[(4-{2-nitro-4-[(trifluoromethyl)sulfonyl]anilino}piperidin-1-yl)sulfonyl]thien-2-yl}methyl)-3-methoxybenzamide;
3-nitro-N-[(5-{[4-(3-phenylpropyl)piperazin-1-yl]sulfonyl}thien-2-yl)methyl]benzamide;
3-nitro-N-({5-[(4-{[4-(trifluoromethyl)pyrimidin-2-yl]amino}piperidin-1-yl)sulfonyl]thien-2-yl}methyl)benzamide;
N-[(5-{[4-(3-cyclohexyl-4-hydroxyanilino)piperidin-1-yl]sulfonyl}thien-2-yl)methyl]-3-nitrobenzamide;
N-({5-[(4-{3-[(butylamino)sulfonyl]anilino}piperidin-1-yl)sulfonyl]thien-2-yl}methyl)-3-nitrobenzamide;
N-[(5-{[4-(3-ethylanilino)piperidin-1-yl]sulfonyl}thien-2-yl)methyl]-3-nitrobenzamide;
3-nitro-N-[(5-{[4-(5,6,7,8-tetrahydronaphthalen-1-ylamino)piperidin-1-yl]sulfonyl}thien-2-yl)methyl]benzamide;
4-nitro-N-[(5-{[4-(3-propylphenoxy)piperidin-1-yl]sulfonyl}thien-2-yl)methyl]benzamide;
N-[(5-{[4-(2,4-difluorobenzoyl)piperidin-1-yl]sulfonyl}thien-2-yl)methyl]-3-nitrobenzamide;
N-[(5-{[4-(2,4-difluorobenzoyl)piperidin-1-yl]sulfonyl}thien-2-yl)methyl]-3-methoxybenzamide;
2-Hydroxy-N-({5-[(4-{3-[(trifluoromethyl)sulfonyl]anilino}piperidin-1-yl)sulfonyl]thien-2-yl}methyl)benzamide;
N-[(5-{[4-(1H-1,2,3-benzotriazol-1-yl)piperidin-1-yl]sulfonyl}thien-2-yl)methyl]-3-methoxybenzamide;
N-[(5-{[4-(1H-1,2,3-benzotriazol-1-yl)piperidin-1-yl]sulfonyl}thien-2-yl)methyl]-2-hydroxybenzamide;
N-{[5-({4-[4-(1,3-dithiolan-2-yl)anilino]piperidin-1-yl}sulfonyl)thien-2-yl]methyl}-3-nitrobenzamide;
3-methoxy-N-[(5-{[4-(3-methoxyanilino)piperidin-1-yl]sulfonyl}thien-2-yl)methyl]benzamide;

3-methoxy-N-{[5-({4-[3-(trifluoromethyl)anilino]piperidin-1-yl}sulfonyl)thien-2-yl]methyl}benzamide;
N-{[5-({4-[3-(dimethylamino)anilino]piperidin-1-yl}sulfonyl)thien-2-yl]methyl}-3-methoxybenzamide;
3-methoxy-N-[(5-{[4-(3-propylanilino)piperidin-1-yl]sulfonyl}thien-2-yl)methyl]benzamide;
3-methoxy-N-{[5-({4-[3-(methylsulfonyl)anilino]piperidin-1-yl}sulfonyl)thien-2-yl]methyl}benzamide;
3-methoxy-N-{[5-({4-[3-(methylsulfanyl)anilino]piperidin-1-yl}sulfonyl)thien-2-yl]methyl}benzamide;
N-{[5-({4-[3-(aminosulfonyl)anilino]piperidin-1-yl}sulfonyl)thien-2-yl]methyl}-3-methoxybenzamide;
methyl 3-({1-[(5-{[(3-methoxybenzoyl)amino]methyl}thien-2-yl)sulfonyl]-piperidin-4-yl}amino)-benzoate;
N-{[5-({4-[3-(aminocarbonyl)anilino]piperidin-1-yl}sulfonyl)thien-2-yl]methyl}-3-methoxybenzamide;
3-methoxy-N-[(5-{[4-(2-methoxyanilino)piperidin-1-yl]sulfonyl}thien-2-yl)methyl]benzamide;
N-({5-[(4-{3-nitroanilino}piperidin-1-yl)sulfonyl]thien-2-yl}methyl)-3-methoxybenzamide;
3-methoxy-N-{[5-({4-[2-(trifluoromethyl)anilino]piperidin-1-yl}sulfonyl)thien-2-yl]methyl}benzamide;
N-({5-[(4-{2-nitroanilino}piperidin-1-yl)sulfonyl]thien-2-yl}methyl)-3-methoxybenzamide;
N-{[5-({4-[4-(aminocarbonyl)anilino]piperidin-1-yl}sulfonyl)thien-2-yl]methyl}-3-methoxybenzamide;
N-{[5-({4-[4-(1,3-dithiolan-2-yl)anilino]piperidin-1-yl}sulfonyl)thien-2-yl]methyl}-3-methoxybenzamide;
N-[(5-{[4-(3-chloroanilino)piperidin-1-yl]sulfonyl}thien-2-yl)methyl]-3-methoxybenzamide;
N-[(5-{[4-(4-chloroanilino)piperidin-1-yl]sulfonyl}thien-2-yl)methyl]-3-methoxybenzamide;
3-methoxy-N-({5-[(4-{4-[(trifluoromethyl)sulfonyl]anilino}piperidin-1-yl)sulfonyl]thien-2-yl}methyl)benzamide;
N-({5-[(4-{3-[amino(imino)methyl]anilino}piperidin-1-yl)sulfonyl]thien-2-yl}methyl)-3-methoxybenzamide;
N-({5-[(4-{3-[(2-hydroxyethyl)sulfonyl]anilino}piperidin-1-yl)sulfonyl]thien-2-yl}methyl)-3-methoxybenzamide;
3-methoxy-N-({5-[(4-{3-[(trifluoromethyl)sulfonyl]anilino}piperidin-1-yl)sulfonyl]thien-2-yl}methyl)benzamide;
N-({5-[(4-anilinopiperidin-1-yl)sulfonyl]thien-2-yl}methyl)-3-methoxybenzamide;
3-methoxy-N-({5-[(4-{3-[(trifluoromethyl)sulfanyl]anilino}piperidin-1-yl)sulfonyl]thien-2-yl}methyl)benzamide;
N-[(5-{[4-(4-hydroxyanilino)piperidin-1-yl]sulfonyl}thien-2-yl)methyl]-3-methoxybenzamide;
3-nitro-N-({5-[(4-{3-[(trifluoromethyl)sulfanyl]anilino}piperidin-1-yl)sulfonyl]thien-2-yl}methyl)benzamide;
4-nitro-N-({5-[(4-{3-[(trifluoromethyl)sulfanyl]anilino}piperidin-1-yl)sulfonyl]thien-2-yl}methyl)benzamide;
N-[(5-{[4-(2-hydroxyanilino)piperidin-1-yl]sulfonyl}thien-2-yl)methyl]-3-methoxybenzamide;
3-methoxy-N-[(5-{[4-(pyrimidin-2-ylamino)piperidin-1-yl]sulfonyl}thien-2-yl)methyl]benzamide;
N-{[5-({4-[(3-aminopyridin-2-yl)amino]piperidin-1-yl}sulfonyl)thien-2-yl]methyl}-3-methoxybenzamide;
N-[(5-{[4-({3-nitropyridin-2-yl}amino)piperidin-1-yl]sulfonyl}thien-2-yl)methyl]-3-methoxybenzamide;
N-{[5-({4-[(2,2-dioxido-1,3-dihydro-2-benzothien-5-yl)amino]piperidin-1-yl}sulfonyl)thien-2-yl]methyl}-3-methoxybenzamide;
N-[(5-{[4-(2,3-dihydro-1H-inden-5-ylamino)piperidin-1-yl]sulfonyl}thien-2-yl)methyl]-3-methoxybenzamide;
3-methoxy-N-[(5-{[4-(2-propylanilino)piperidin-1-yl]sulfonyl}thien-2-yl)methyl]benzamide;
3-methoxy-N-[(5-{[4-(4-propylanilino)piperidin-1-yl]sulfonyl}thien-2-yl)methyl]benzamide;
N-[(5-{[4-(3-tert-butylanilino)piperidin-1-yl]sulfonyl}thien-2-yl)methyl]-3-methoxybenzamide;
N-({5-[(4-{[3-chloro-5-(trifluoromethyl)pyridin-2-yl]amino}piperidin-1-yl)sulfonyl]thien-2-yl}methyl)-3-methoxybenzamide;
3-methoxy-N-{[5-({4-[3-(1,3-oxazol-5-yl)anilino]piperidin-1-yl}sulfonyl)thien-2-yl]methyl}benzamide;
N-[(5-{[4-([1,1'-biphenyl]-3-ylamino)piperidin-1-yl]sulfonyl}thien-2-yl)methyl]-3-methoxybenzamide;
3-methoxy-N-[(5-{[4-(3-propylphenoxy)piperidin-1-yl]sulfonyl}thien-2-yl)methyl]benzamide;
3-methoxy-N-{[5-({4-[3-(morpholin-4-ylsulfonyl)anilino]piperidin-1-yl}sulfonyl)thien-2-yl]methyl}benzamide;
3-methoxy-N-[(5-{[4-(2-phenylethyl)piperidin-1-yl]sulfonyl}thien-2-yl)methyl]benzamide;
N-[(5-{[4-(3-benzylanilino)piperidin-1-yl]sulfonyl}thien-2-yl)methyl]-3-methoxybenzamide;
3-methoxy-N-[(5-{[4-(3-phenylpropyl)piperazin-1-yl]sulfonyl}thien-2-yl)methyl]benzamide;
3-methoxy-N-({5-[(4-{[4-(trifluoromethyl)pyrimidin-2-yl]amino}piperidin-1-yl)sulfonyl]thien-2-yl}methyl)benzamide;
N-[(5-{[4-(3-cyclohexyl-4-hydroxyanilino)piperidin-1-yl]sulfonyl}thien-2-yl)methyl]-3-methoxybenzamide;
N-({5-[(4-{3-[(butylamino)sulfonyl]anilino}piperidin-1-yl)sulfonyl]thien-2-yl}methyl)-3-methoxybenzamide;
N-[(5-{[4-(3-ethylanilino)piperidin-1-yl]sulfonyl}thien-2-yl)methyl]-3-methoxybenzamide;
3-methoxy-N-[(5-{[4-(5,6,7,8-tetrahydronaphthalen-1-ylamino)piperidin-1-yl]sulfonyl}thien-2-yl)methyl]benzamide;
N-[(5-{[4-(1H-1,2,3-benzotriazol-1-yl)piperidin-1-yl]sulfonyl}thien-2-yl)methyl]-5-nitro-1H-pyrazole-3-carboxamide;
N-[(5-{[4-(1H-1,2,3-benzotriazol-1-yl)piperidin-1-yl]sulfonyl}thien-2-yl)methyl]-2-oxo-1,2-dihydropyridine-3-carboxamide;
N-[(5-{[4-(1H-1,2,3-benzotriazol-1-yl)piperidin-1-yl]sulfonyl}thien-2-yl)methyl]-2-thioxo-1,2-dihydropyridine-3-carboxamide;
N-[(5-{[4-(1H-1,2,3-benzotriazol-1-yl)piperidin-1-yl]sulfonyl}thien-2-yl)methyl]-3,4-dihydroxybenzamide;
N-[(5-{[4-(1H-1,2,3-benzotriazol-1-yl)piperidin-1-yl]sulfonyl}thien-2-yl)methyl]pyridine-2-carboxamide;
N-[(5-{[4-(hexyloxy)piperidin-1-yl]sulfonyl}thien-2-yl)methyl]-3-methoxybenzamide;
N-({5-[(4-heptanoylpiperidin-1-yl)sulfonyl]thien-2-yl}methyl)-3-methoxybenzamide;
4-chloro-N-[(5-{[4-(3-propylanilino)piperidin-1-yl]sulfonyl}-2-furyl)methyl]benzamide;
4-chloro-N-[(5-{[4-(3-chloroanilino)piperidin-1-yl]sulfonyl}-2-furyl)methyl]benzamide;
4-chloro-N-[(5-{[4-(3-methoxyanilino)piperidin-1-yl]sulfonyl}-2-furyl)methyl]benzamide;
4-chloro-N-{[5-({4-[3-(trifluoromethyl)anilino]piperidin-1-yl}sulfonyl)-2-furyl]methyl}benzamide;

4-chloro-N-{[5-({4-[3-(dimethylamino)anilino]piperidin-1-yl}sulfonyl)-2-furyl]methyl}benzamide;
4-chloro-N-{[5-({4-[3-(methylsulfonyl)anilino]piperidin-1-yl}sulfonyl)-2-furyl]methyl}benzamide;
4-chloro-N-{[5-({4-[3-(methylsulfanyl)anilino]piperidin-1-yl}sulfonyl)-2-furyl]methyl}benzamide;
N-{[5-({4-[3-(aminosulfonyl)anilino]piperidin-1-yl}sulfonyl)-2-furyl]methyl}-4-chlorobenzamide;
methyl 3-({1-[(5-{[(4-chlorobenzoyl)amino]methyl}-2-furyl)sulfonyl]piperidin-4-yl}amino)benzoate;
3-({1-[(5-{[(4-chlorobenzoyl)amino]methyl}-2-furyl)sulfonyl]piperidin-4-yl}amino)benzamide;
4-chloro-N-({5-[(4-{3-nitroanilino}piperidin-1-yl)sulfonyl]-2-furyl}methyl)benzamide;
4-chloro-N-[(5-{[4-(2-methoxyanilino)piperidin-1-yl]sulfonyl}-2-furyl)methyl]benzamide;
4-chloro-N-{[5-({4-[2-(trifluoromethyl)anilino]piperidin-1-yl}sulfonyl)-2-furyl]methyl}benzamide;
4-chloro-N-({5-[(4-{2-nitroanilino}piperidin-1-yl)sulfonyl]-2-furyl}methyl)benzamide;
4-chloro-N-[(5-{[4-(4-chloroanilino)piperidin-1-yl]sulfonyl}-2-furyl)methyl]benzamide;
4-chloro-N-{[5-({4-[4-(trifluoromethyl)anilino]piperidin-1-yl}sulfonyl)-2-furyl]methyl}benzamide;
4-chloro-N-({5-[(4-{4-[(trifluoromethyl)sulfonyl]anilino}piperidin-1-yl)sulfonyl]-2-furyl}methyl)benzamide;
N-{[5-({4-[4-(aminocarbonyl)anilino]piperidin-1-yl}sulfonyl)-2-furyl]methyl}-4-chlorobenzamide;
4-chloro-N-{[5-({4-[4-(1,3-dithiolan-2-yl)anilino]piperidin-1-yl}sulfonyl)-2-furyl]methyl}benzamide;
N-({5-[(4-{3-[amino(imino)methyl]anilino}piperidin-1-yl)sulfonyl]-2-furyl}methyl)-4-chlorobenzamide;
4-chloro-N-({5-[(4-{3-[(trifluoromethyl)sulfonyl]anilino}piperidin-1-yl)sulfonyl]-2-furyl}methyl)benzamide;
N-({5-[(4-anilinopiperidin-1-yl)sulfonyl]-2-furyl}methyl)-4-chlorobenzamide;
4-nitro-N-({5-[(4-{3-[(trifluoromethyl)sulfanyl]anilino}piperidin-1-yl)sulfonyl]-2-furyl}methyl)benzamide;
4-chloro-N-({5-[(3-{3-[(trifluoromethyl)sulfonyl]anilino}pyrrolidin-1-yl)sulfonyl]thien-2-yl}methyl)benzamide;
4-chloro-N-({5-[(4-{3-[(trifluoromethyl)sulfonyl]anilino}azepan-1-yl)sulfonyl]thien-2-yl}methyl)benzamide;
5-{[(3-methoxybenzoyl)amino]methyl}-2-[(4-{3-[(trifluoromethyl)sulfonyl]-anilino}piperidin-1-yl)sulfonyl]thiophene-3-carboxylic acid;
5-{[(3-methoxybenzoyl)amino]methyl}-2-{[4-(octylamino)piperidin-1-yl]sulfonyl}thiophene-3-carboxylic acid;
N-(2-hydroxyethyl)-5-{[(3-methoxybenzoyl)amino]methyl}-2-[(4-{3-[(trifluoro-methyl)sulfonyl]anilino}piperidin-1-yl)sulfonyl]thiophene-3-carboxamide;
N-({4-(hydrazinocarbonyl)-5-[(4-{3-[(trifluoromethyl)sulfonyl]anilino}-piperidin-1-yl)sulfonyl]thien-2-yl}methyl)-3-methoxybenzamide;
5-{[(3-methoxybenzoyl)amino]methyl}-2-[(4-{3-[(trifluoromethyl)sulfonyl]-anilino}piperidin-1-yl)sulfonyl]thiophene-3-carboxamide;
N-[2-(dimethylamino)ethyl]-5-{[(3-methoxybenzoyl)amino]methyl}-2-[(4-{3-[(trifluoromethyl)sulfonyl]anilino}piperidin-1-yl)sulfonyl]thiophene-3-carboxamide;
N-({4-(hydroxymethyl)-5-[(4-{3-[(trifluoromethyl)sulfonyl]anilino}piperidin-1-yl)sulfonyl]thien-2-yl}methyl)-3-methoxybenzamide;
4-chloro-N-[(5-{[4-(hexylamino)piperidin-1-yl]sulfonyl}thien-2-yl)methyl]benzamide;
3-Methoxy-N-{[5-({4-[(4-trifluoromethylbenzyl)amino]piperidin-1-yl}sulfonyl)thien-2-yl]methyl}benzamide;
4-chloro-N-[(5-{[4-(1,3-thiazol-2-ylamino)piperidin-1-yl]sulfonyl}thien-2-yl)methyl]benzamide;
4-chloro-N-[(5-{[4-(heptylamino)piperidin-1-yl]sulfonyl}thien-2-yl)methyl]benzamide;
4-chloro-N-[(5-{[4-(pentylamino)piperidin-1-yl]sulfonyl}thien-2-yl)methyl]benzamide;
4-chloro-N-[(5-{[4-(butylamino)piperidin-1-yl]sulfonyl}thien-2-yl)methyl]benzamide;
4-chloro-N-[(5-{[4-(dodecylamino)piperidin-1-yl]sulfonyl}thien-2-yl)methyl]benzamide;
4-chloro-N-{[5-({4-[(2-cyclohexylethyl)amino]piperidin-1-yl}sulfonyl)thien-2-yl]methyl}benzamide;
4-chloro-N-{[5-({4-[(cyclohexylmethyl)amino]piperidin-1-yl}sulfonyl)thien-2-yl]methyl}benzamide;
4-chloro-N-({5-[(4-{[(1R)-1-cyclohexylethyl]amino}piperidin-1-yl)sulfonyl]thien-2-yl}methyl)benzamide;
N-{[5-({4-[(1R,2R,4S)-bicyclo[2.2.1]hept-2-ylamino]piperidin-1-yl}sulfonyl)thien-2-yl]methyl}-4-chlorobenzamide;
4-chloro-N-{[5-({4-[(2-propoxyethyl)amino]piperidin-1-yl}sulfonyl)thien-2-yl]methyl}benzamide;
N-{[5-({4-[(1-adamantylmethyl)amino]piperidin-1-yl}sulfonyl)thien-2-yl]methyl}-4-chlorobenzamide;
4-chloro-N-{[5-({4-[(2-pyridin-2-ylethyl)amino]piperidin-1-yl}sulfonyl)thien-2-yl]methyl}benzamide;
4-chloro-N-{[5-({4-[(2-piperidin-1-ylethyl)amino]piperidin-1-yl}sulfonyl)thien-2-yl]methyl}benzamide;
4-chloro-N-{[5-({4-[(2-ethylhexyl)amino]piperidin-1-yl}sulfonyl)thien-2-yl]methyl}benzamide;
4-chloro-N-({5-[(4-{[3-(1H-imidazol-1-yl)propyl]amino}piperidin-1-yl)sulfonyl]thien-2-yl}methyl)benzamide;
4-chloro-N-[(5-{[4-(octylamino)piperidin-1-yl]sulfonyl}thien-2-yl)methyl]benzamide;
N-[(5-{[4-(heptylamino)piperidin-1-yl]sulfonyl}thien-2-yl)methyl]-3-methoxybenzamide;
3-methoxy-N-[(5-{[4-(octylamino)piperidin-1-yl]sulfonyl}thien-2-yl)methyl]benzamide;
3-methoxy-N-[(5-{[4-(pentylamino)piperidin-1-yl]sulfonyl}thien-2-yl)methyl]benzamide;
N-[(5-{[4-(butylamino)piperidin-1-yl]sulfonyl}thien-2-yl)methyl]-3-methoxybenzamide;
N-[(5-{[4-(dodecylamino)piperidin-1-yl]sulfonyl}thien-2-yl)methyl]-3-methoxybenzamide;
N-{[5-({4-[(2-cyclohexylethyl)amino]piperidin-1-yl}sulfonyl)thien-2-yl]methyl}-3-methoxybenzamide;
N-({5-[(4-{[(1R)-1-cyclohexylethyl]amino}piperidin-1-yl)sulfonyl]thien-2-yl}methyl)-3-methoxybenzamide;
N-{[5-({4-[(1R,2R,4S)-bicyclo[2.2.1]hept-2-ylamino]piperidin-1-yl}sulfonyl)thien-2-yl]methyl}-3-methoxybenzamide;
3-methoxy-N-{[5-({4-[(2-propoxyethyl)amino]piperidin-1-yl}sulfonyl)thien-2-yl]methyl}benzamide;
N-{[5-({4-[(1-adamantylmethyl)amino]piperidin-1-yl}sulfonyl)thien-2-yl]methyl}-3-methoxybenzamide;
N-{[5-({4-[(3,3-diethoxypropyl)amino]piperidin-1-yl}sulfonyl)thien-2-yl]methyl}-3-methoxybenzamide;
3-methoxy-N-{[5-({4-[(3-morpholin-4-ylpropyl)amino]piperidin-1-yl}sulfonyl)thien-2-yl]methyl}benzamide;

3-methoxy-N-{[5-({4-[(2-pyridin-2-ylethyl)amino]piperidin-1-yl}sulfonyl)thien-2-yl]methyl}benzamide;
3-methoxy-N-{[5-({4-[(2-piperidin-1-ylethyl)amino]piperidin-1-yl}sulfonyl)thien-2-yl]methyl}benzamide;
N-{[5-({4-[(2-ethylhexyl)amino]piperidin-1-yl}sulfonyl)thien-2-yl]methyl}-3-methoxybenzamide;
N-({5-[(4-{[3-(1H-imidazol-1-yl)propyl]amino}piperidin-1-yl)sulfonyl]thien-2-yl}methyl)-3-methoxybenzamide;
N-[(5-{[4-(hexylamino)piperidin-1-yl]sulfonyl}thien-2-yl)methyl]-3-methoxybenzamide;
N-[(5-{[4-(heptylamino)azepan-1-yl]sulfonyl}thien-2-yl)methyl]-3-methoxybenzamide;
3-methoxy-N-[(5-{[4-(octylamino)azepan-1-yl]sulfonyl}thien-2-yl)methyl]benzamide;
3-methoxy-N-[(5-{[4-(pentylamino)azepan-1-yl]sulfonyl}thien-2-yl)methyl]benzamide;
N-[(5-{[4-(butylamino)azepan-1-yl]sulfonyl}thien-2-yl)methyl]-3-methoxybenzamide;
N-[(5-{[4-(dodecylamino)azepan-1-yl]sulfonyl}thien-2-yl)methyl]-3-methoxybenzamide;
N-{[5-({4-[(2-cyclohexylethyl)amino]azepan-1-yl}sulfonyl)thien-2-yl]methyl}-3-methoxybenzamide;
N-({5-[(4-{[(1R)-1-cyclohexylethyl]amino}azepan-1-yl)sulfonyl]thien-2-yl}methyl)-3-methoxybenzamide;
N-{[5-({4-[(1R,2R,4S)-bicyclo[2.2.1]hept-2-ylamino]azepan-1-yl}sulfonyl)thien-2-yl]methyl}-3-methoxybenzamide;
3-methoxy-N-{[5-({4-[(2-propoxyethyl)amino]azepan-1-yl}sulfonyl)thien-2-yl]methyl}benzamide;
N-{[5-({4-[(cyclohexylmethyl)amino]azepan-1-yl}sulfonyl)thien-2-yl]methyl}-3-methoxybenzamide;
N-{[5-({4-[(1-adamantylmethyl)amino]azepan-1-yl}sulfonyl)thien-2-yl]methyl}-3-methoxybenzamide;
3-methoxy-N-{[5-({4-[(3-morpholin-4-ylpropyl)amino]azepan-1-yl}sulfonyl)thien-2-yl]methyl}benzamide;
3-methoxy-N-{[5-({4-[(2-pyridin-2-ylethyl)amino]azepan-1-yl}sulfonyl)thien-2-yl]methyl}benzamide;
3-methoxy-N-{[5-({4-[(2-piperidin-1-ylethyl)amino]azepan-1-yl}sulfonyl)thien-2-yl]methyl}benzamide;
N-{[5-({4-[(2-ethylhexyl)amino]azepan-1-yl}sulfonyl)thien-2-yl]methyl}-3-methoxybenzamide;
N-({5-[(4-{[3-(1H-imidazol-1-yl)propyl]amino}azepan-1-yl)sulfonyl]thien-2-yl}methyl)-3-methoxybenzamide;
4-chloro-N-[(5-{[4-(heptylamino)azepan-1-yl]sulfonyl}thien-2-yl)methyl]benzamide;
4-chloro-N-[(5-{[4-(octylamino)azepan-1-yl]sulfonyl}thien-2-yl)methyl]benzamide;
4-chloro-N-[(5-{[4-(pentylamino)azepan-1-yl]sulfonyl}thien-2-yl)methyl]benzamide;
N-[(5-{[4-(butylamino)azepan-1-yl]sulfonyl}thien-2-yl)methyl]-4-chlorobenzamide;
4-chloro-N-[(5-{[4-(dodecylamino)azepan-1-yl]sulfonyl}thien-2-yl)methyl]benzamide;
4-chloro-N-{[5-({4-[(2-cyclohexylethyl)amino]azepan-1-yl}sulfonyl)thien-2-yl]methyl}benzamide;
N-{[5-({4-[(1R,2R,4S)-bicyclo[2.2.1]hept-2-ylamino]azepan-1-yl}sulfonyl)thien-2-yl]methyl}-4-chlorobenzamide;
4-chloro-N-{[5-({4-[(2-propoxyethyl)amino]azepan-1-yl}sulfonyl)thien-2-yl]methyl}benzamide;
4-chloro-N-{[5-({4-[(2-ethylhexyl)amino]azepan-1-yl}sulfonyl)thien-2-yl]methyl}benzamide;
4-chloro-N-[(5-{[4-(hexylamino)azepan-1-yl]sulfonyl}thien-2-yl)methyl]benzamide;
N-[(5-{[4-(hexylamino)azepan-1-yl]sulfonyl}thien-2-yl)methyl]-3-methoxybenzamide;
3-methoxy-N-[(5-{[4-({2-[3-(trifluoromethyl)phenyl]ethyl}amino)piperidin-1-yl]sulfonyl}thien-2-yl)methyl]benzamide;
3-methoxy-N-({5-[(4-{[2-(4-methylphenyl)ethyl]amino}piperidin-1-yl)sulfonyl]thien-2-yl}methyl)benzamide;
3-methoxy-N-({5-[(4-{[(1S,2R)-2-phenylcyclopropyl]amino}piperidin-1-yl)sulfonyl]thien-2-yl}methyl)benzamide;
3-methoxy-N-{[5-({4-[(1-naphthylmethyl)amino]piperidin-1-yl}sulfonyl)thien-2-yl]methyl}benzamide;
3-methoxy-N-{[5-({4-[(2-phenylpropyl)amino]piperidin-1-yl}sulfonyl)thien-2-yl]methyl}benzamide;
N-({5-[(4-{[2-(4-hydroxyphenyl)ethyl]amino}piperidin-1-yl)sulfonyl]thien-2-yl}methyl)-3-methoxybenzamide;
3-methoxy-N-{[5-({4-[(3-phenylpropyl)amino]piperidin-1-yl}sulfonyl)thien-2-yl]methyl}benzamide;
N-{[5-({4-[(2,3-dihydroxypropyl)amino]piperidin-1-yl}sulfonyl)thien-2-yl]methyl}-3-methoxybenzamide;
N-{[5-({4-[(2-hydroxyethyl)amino]piperidin-1-yl}sulfonyl)thien-2-yl]methyl}-3-methoxybenzamide;
3-methoxy-N-[(5-{[4-(nonylamino)piperidin-1-yl]sulfonyl}thien-2-yl)methyl]benzamide;
3-methoxy-N-[(5-{[4-(decylamino)piperidin-1-yl]sulfonyl}thien-2-yl)methyl]benzamide;
3-methoxy-N-[(5-{[4-(ethylamino)piperidin-1-yl]sulfonyl}thien-2-yl)methyl]benzamide;
N-{[5-({4-[(2-[1,1'-biphenyl]-4-ylethyl)amino]piperidin-1-yl}sulfonyl)thien-2-yl]methyl}-3-methoxybenzamide;
N-{[5-({4-[([1,1'-biphenyl]-3-ylmethyl)amino]piperidin-1-yl}sulfonyl)thien-2-yl]methyl}-3-methoxybenzamide;
3-methoxy-N-{[5-({4-[(2-thien-2-ylethyl)amino]piperidin-1-yl}sulfonyl)thien-2-yl]methyl}benzamide;
3-methoxy-N-[(5-{[4-({4-[(trifluoromethyl)sulfonyl]benzyl}amino)piperidin-1-yl]sulfonyl}thien-2-yl)methyl]benzamide;
3-methoxy-N-{[5-({4-[(quinolin-4-ylmethyl)amino]piperidin-1-yl}sulfonyl)thien-2-yl]methyl}benzamide;
N-{[5-({4-[([1,1'-biphenyl]-4-ylmethyl)amino]-1-piperidinyl}sulfonyl)-2-thienyl]methyl}-3-methoxybenzamide;
4-chloro-N-{[5-({[4-[(2-{[(trifluoromethyl)sulfonyl]amino}ethyl)amino]-1-piperidinyl}sulfonyl)-2-thienyl]methyl}benzamide;
4-chloro-N-[(5-{[4-(propylamino)-1-piperidinyl]sulfonyl}-2-thienyl)methyl]benzamide;
4-chloro-N-[(5-{[4-({4-[(trifluoromethyl)sulfonyl]benzyl}amino)-1-piperidinyl]sulfonyl}-2-thienyl)methyl]benzamide;
4-chloro-N-{[5-({4-[(3,4-dihydroxybenzyl)amino]-1-piperidinyl}sulfonyl)-2-thienyl]methyl}benzamide;
methyl [{1-[(5-{[(4-chlorobenzoyl)amino]methyl}-2-thienyl)sulfonyl]-4-piperidinyl}(hexyl)amino]acetate;
tert-butyl [{1-[(5-{[(4-chlorobenzoyl)amino]methyl}-2-thienyl)sulfonyl]-4-piperidinyl}(hexyl)amino]acetate;
[{1-[(5-{[(4-chlorobenzoyl)amino]methyl}-2-thienyl)sulfonyl]-4-piperidinyl}(hexyl)amino]acetic acid;
N-[(5-{[3-(heptylamino)pyrrolidin-1-yl]sulfonyl}thien-2-yl)methyl]-3-methoxybenzamide;
3-methoxy-N-[(5-{[3-(octylamino)pyrrolidin-1-yl]sulfonyl}thien-2-yl)methyl]benzamide;

3-methoxy-N-[(5-{[3-(pentylamino)pyrrolidin-1-yl]sulfonyl}thien-2-yl)methyl]benzamide;
N-(5-{[3-(butylamino)pyrrolidin-1-yl]sulfonyl}thien-2-yl)methyl]-3-methoxybenzamide;
N-[(5-{[3-(dodecylamino)pyrrolidin-1-yl]sulfonyl}thien-2-yl)methyl]-3-methoxybenzamide;
N-{[5-({3-[(2-cyclohexylethyl)amino]pyrrolidin-1-yl}sulfonyl)thien-2-yl]methyl}-3-methoxybenzamide;
N-({5-[(3-{[(1R)-1-cyclohexylethyl]amino}pyrrolidin-1-yl)sulfonyl]thien-2-yl}methyl)-3-methoxybenzamide;
N-{[5-({3-[(1R,2R,4S)-bicyclo[2.2.1]hept-2-ylamino]pyrrolidin-1-yl}sulfonyl)thien-2-yl]methyl}-3-methoxybenzamide;
3-methoxy-N-{[5-({3-[(2-propoxyethyl)amino]pyrrolidin-1-yl}sulfonyl)thien-2-yl]methyl}benzamide;
N-{[5-({3-[(cyclohexylmethyl)amino]pyrrolidin-1-yl}sulfonyl)thien-2-yl]methyl}-3-methoxybenzamide;
N-{[5-({3-[(1-adamantylmethyl)amino]pyrrolidin-1-yl}sulfonyl)thien-2-yl]methyl}-3-methoxybenzamide;
3-methoxy-N-{[5-({3-[(3-morpholin-4-ylpropyl)amino]pyrrolidin-1-yl}sulfonyl)thien-2-yl]methyl}benzamide;
3-methoxy-N-{[5-({3-[(2-pyridin-2-ylethyl)amino]pyrrolidin-1-yl}sulfonyl)thien-2-yl]methyl}benzamide;
3-methoxy-N-{[5-({3-[(2-piperidin-1-ylethyl)amino]pyrrolidin-1-yl}sulfonyl)thien-2-yl]methyl}benzamide;
N-{[5-({3-[(2-ethylhexyl)amino]pyrrolidin-1-yl}sulfonyl)thien-2-yl]methyl}-3-methoxybenzamide;
N-[(5-{[3-(hexylamino)pyrrolidin-1-yl]sulfonyl}thien-2-yl)methyl]-3-methoxybenzamide;
4-chloro-N-[(5-{[3-(heptylamino)pyrrolidin-1-yl]sulfonyl}thien-2-yl)methyl]benzamide;
4-chloro-N-[(5-{[3-(hexylamino)pyrrolidin-1-yl]sulfonyl}thien-2-yl)methyl]benzamide;
4-chloro-N-[(5-{[3-(pentylamino)pyrrolidin-1-yl]sulfonyl}thien-2-yl)methyl]benzamide;
N-[(5-{[3-(butylamino)pyrrolidin-1-yl]sulfonyl}thien-2-yl)methyl]-4-chlorobenzamide;
4-chloro-N-{[5-({3-[(2-cyclohexylethyl)amino]pyrrolidin-1-yl}sulfonyl)thien-2-yl]methyl}benzamide;
N-{[5-({3-[(1R,2R,4S)-bicyclo[2.2.1]hept-2-ylamino]pyrrolidin-1-yl}sulfonyl)thien-2-yl]methyl}-4-chlorobenzamide;
4-chloro-N-({5-[(3-{[(1-hydroxycyclohexyl)methyl]amino}pyrrolidin-1-yl)sulfonyl]thien-2-yl}methyl)benzamide;
N-{[5-({3-[(1-adamantylmethyl)amino]pyrrolidin-1-yl}sulfonyl)thien-2-yl]methyl}-4-chlorobenzamide;
4-chloro-N-{[5-({3-[(3-morpholin-4-ylpropyl)amino]pyrrolidin-1-yl}sulfonyl)thien-2-yl]methyl}benzamide;
4-chloro-N-{[5-({3-[(2-pyridin-2-ylethyl)amino]pyrrolidin-1-yl}sulfonyl)thien-2-yl]methyl}benzamide;
4-chloro-N-{[5-({3-[(2-piperidin-1-ylethyl)amino]pyrrolidin-1-yl}sulfonyl)thien-2-yl]methyl}benzamide;
4-chloro-N-{[5-({3-[(2-ethylhexyl)amino]pyrrolidin-1-yl}sulfonyl)thien-2-yl]methyl}benzamide;
4-chloro-N-[(5-{[3-(octylamino)pyrrolidin-1-yl]sulfonyl}thien-2-yl)methyl]benzamide;
methyl (2S)-1-[(5-{[(4-chlorobenzoyl)amino]methyl}-2-thienyl)sulfonyl]-4-(hexylamino)-2-pyrrolidinecarboxylate;
3-methoxy-N-{[5-({4-[(pentylamino)methyl]piperidin-1-yl}sulfonyl)thien-2-yl]methyl}benzamide;
N-{[5-({4-[2-(butylamino)ethyl]piperidin-1-yl}sulfonyl)thien-2-yl]methyl}-3-methoxybenzamide;
N-{[5-({4-[(4-butylanilino)methyl]-1-piperidinyl}sulfonyl)-2-thienyl]methyl}-3-methoxybenzamide;
4-chloro-N-{[5-({4-[hexyl(methyl)amino]piperidin-1-yl}sulfonyl)thien-2-yl]methyl}benzamide;
4-chloro-N-{[5-({4-[(cyclohexylmethyl)(hexyl)amino]piperidin-1-yl}sulfonyl)thien-2-yl]methyl}benzamide;
N-{[5-({4-[benzyl(hexyl)amino]piperidin-1-yl}sulfonyl)thien-2-yl]methyl}-4-chlorobenzamide;
4-chloro-N-{[5-({4-[hexyl(pyridin-3-ylmethyl)amino]piperidin-1-yl}sulfonyl)thien-2-yl]methyl}benzamide;
4-chloro-N-{[5-({4-[hexyl(pyridin-4-ylmethyl)amino]piperidin-1-yl}sulfonyl)thien-2-yl]methyl}benzamide;
4-chloro-N-{[5-({4-[hexyl(pyridin-2-ylmethyl)amino]piperidin-1-yl}sulfonyl)thien-2-yl]methyl}benzamide;
N-{[5-({4-[butyl(hexyl)amino]piperidin-1-yl}sulfonyl)thien-2-yl]methyl}-4-chlorobenzamide;
4-chloro-N-{[5-({4-[hexyl(3-phenylpropyl)amino]piperidin-1-yl}sulfonyl)thien-2-yl]methyl}benzamide;
4-chloro-N-{[5-({4-[hexyl(2-phenylethyl)amino]piperidin-1-yl}sulfonyl)thien-2-yl]methyl}benzamide;
N-{[5-({4-[[(5-bromo-2-furyl)methyl](hexyl)amino]piperidin-1-yl}sulfonyl)thien-2-yl]methyl}-4-chlorobenzamide;
3-methoxy-N-({5-[(4-{methyl-[4-(trifluoromethyl)benzyl]amino}-1-piperidinyl)sulfonyl]-2-thienyl}methyl)benzamide;
4-chloro-N-{[5-({4-[(3-chlorobenzyl)amino]piperidin-1-yl}sulfonyl)thien-2-yl]methyl}benzamide;
3-methoxy-N-({5-[(4-{[4-(trifluoromethyl)benzyl]amino}piperidin-1-yl)sulfonyl]thien-2-yl}methyl)benzamide;
3-methoxy-N-{[5-({4-[(3-methylbenzyl)amino]piperidin-1-yl}sulfonyl)thien-2-yl]methyl}benzamide;
3-methoxy-N-{[5-({4-[(4-propylbenzyl)amino]piperidin-1-yl}sulfonyl)thien-2-yl]methyl}benzamide;
3-methoxy-N-({5-[(4-{[(3-trifluoromethyl)benzyl]amino}piperidin-1-yl)sulfonyl]thien-2-yl}methyl)benzamide;
3-methoxy-N-({5-[(4-{[4-(trifluoromethoxy)benzyl]amino}piperidin-1-yl)sulfonyl]thien-2-yl}methyl)benzamide;
N-({5-[(4-{[4-(difluoromethoxy)benzyl]amino}piperidin-1-yl)sulfonyl]thien-2-yl}methyl)-3-methoxybenzamide;
3-methoxy-N-{[5-({4-[(2,3,4,5,6-pentamethylbenzyl)amino]piperidin-1-yl}sulfonyl)thien-2-yl]methyl}benzamide;
3-methoxy-N-{[5-({4-[(4-propoxybenzyl)amino]piperidin-1-yl}sulfonyl)thien-2-yl]methyl}benzamide;
N-{[5-({4-[(4-butoxybenzyl)amino]piperidin-1-yl}sulfonyl)thien-2-yl]methyl}-3-methoxybenzamide;
3-methoxy-N-{[5-({4-[(4-methoxybenzyl)amino]piperidin-1-yl}sulfonyl)thien-2-yl]methyl}benzamide;
3-methoxy-N-{[5-({4-[(pyridin-4-ylmethyl)amino]piperidin-1-yl}sulfonyl)thien-2-yl]methyl}benzamide;
3-methoxy-N-{[5-({4-[(pyridin-2-ylmethyl)amino]piperidin-1-yl}sulfonyl)thien-2-yl]methyl}benzamide;
3-methoxy-N-{[5-({4-[(pyridin-3-ylmethyl)amino]piperidin-1-yl}sulfonyl)thien-2-yl]methyl}benzamide;
N-{[5-({4-[(4-tert-butylbenzyl)amino]piperidin-1-yl}sulfonyl)thien-2-yl]methyl}-3-methoxybenzamide;
N-{[5-({4-[(3-ethoxybenzyl)amino]piperidin-1-yl}sulfonyl)thien-2-yl]methyl}-3-methoxybenzamide;
3-methoxy-N-{[5-({4-[(4-phenoxybenzyl)amino]piperidin-1-yl}sulfonyl)thien-2-yl]methyl}benzamide;

3-methoxy-N-[(5-{[4-({4-[(trifluoromethyl)sulfanyl]
benzyl}amino)piperidin-1-yl]sulfonyl}thien-2-yl)me-
thyl]benzamide;
3-methoxy-N-({5-[(4-{[4-(methylsulfonyl)benzyl]
amino}-1-piperidinyl)sulfonyl]-2-thienyl}methyl)ben-
zamide;
N-({5-[(4-{[3,5-bis(trifluoromethyl)benzyl]amino}-1-pi-
peridinyl)sulfonyl]-2-thienyl}methyl)-3-methoxyben-
zamide;
N-({5-[(4-{[2,5-bis(trifluoromethyl)benzyl]amino}-1-pi-
peridinyl)sulfonyl]-2-thienyl}methyl)-3-methoxyben-
zamide;
N-({5-[(4-{[4-(ethylsulfanyl)benzyl]amino}-1-piperidi-
nyl)sulfonyl]-2-thienyl}methyl)-3-methoxybenzamide;
3-methoxy-N-[(5-{[4-({3-[(trifluoromethyl)sulfanyl]
benzyl}amino)-1-piperidinyl]sulfonyl}-2-thienyl)me-
thyl]benzamide;
N-({5-[4-{[(2,2-difluoro-1,3-benzodioxol-5-yl)methyl]
amino}-1-piperidinyl)sulfonyl]-2-thienyl}methyl)-3-
methoxybenzamide;
N-{[5-({4-[(4-iodobenzyl)amino]-1-
piperidinyl}sulfonyl)-2-thienyl]methyl}-3-methoxy-
benzamide;
N-({5-[(4-{[4-(benzyloxy)benzyl]amino}-1-piperidinyl)
sulfonyl]-2-thienyl}methyl)-3-methoxybenzamide;
N-{[5-({4-[(mesitylmethyl)amino]-1-
piperidinyl}sulfonyl)-2-thienyl]methyl}-3-methoxy-
benzamide;
N-{[5-({4-[(4-chlorobenzyl)amino]-1-
piperidinyl}sulfonyl)-2-thienyl]methyl}-3-methoxy-
benzamide;
N-{[5-({4-[(4-ethylbenzyl)amino]-1-
piperidinyl}sulfonyl)-2-thienyl]methyl}-3-methoxy-
benzamide;
3-methoxy-N-{[5-({4-[(4-pentylbenzyl)amino]-1-
piperidinyl}sulfonyl)-2-thienyl]methyl}benzamide;
3-methoxy-N-[(5-{[4-({1-[4-(trifluoromethyl)phenyl]
ethyl}amino)-1-piperidinyl]sulfonyl}-2-thienyl)me-
thyl]benzamide;
3-methoxy-N-{[5-({4-[(4-methylbenzyl)amino]-1-
piperidinyl}sulfonyl)-2-thienyl]methyl}benzamide;
N-{[5-({4-[(4-butylbenzyl)amino]-1-
piperidinyl}sulfonyl)-2-thienyl]methyl}-3-methoxy-
benzamide;
N-{[5-({4-[(4-isopropylbenzyl)amino]-1-
piperidinyl}sulfonyl)-2-thienyl]methyl}-3-methoxy-
benzamide;
N-{[5-({4-[(4-isobutylbenzyl)amino]-1-
piperidinyl}sulfonyl)-2-thienyl]methyl}-3-methoxy-
benzamide;
N-({5-[(4-{[(1-hydroxy-1lambda~5~-pyridin-4-yl)me-
thyl]amino}-1-piperidinyl)sulfonyl]-2-
thienyl}methyl)-3-methoxybenzamide;
N-{[5-({4-[(2,3-dihydro-1,4-benzodioxin-6-ylmethyl)
amino]-1-piperidinyl}sulfonyl)-2-thienyl]methyl}-3-
methoxybenzamide;
N-{[5-({4-[(2,3-dihydro-1-benzofuran-5-ylmethyl)
amino]-1-piperidinyl}sulfonyl)-2-thienyl]methyl}-3-
methoxybenzamide;
4-chloro-N-{[5-({4-[(4-propylbenzyl)amino]-1-
piperidinyl}sulfonyl)-2-thienyl]methyl}benzamide;
4-chloro-N-({5-[(4-{[4-(trifluoromethoxy)benzyl]
amino}-1-piperidinyl)sulfonyl]-2-thienyl}methyl)ben-
zamide;
4-chloro-N-({5-[(4-{[4-(difluoromethoxy)benzyl]
amino}-1-piperidinyl)sulfonyl]-2-thienyl}methyl)ben-
zamide;
4-chloro-N-{[5-({4-[(4-propoxybenzyl)amino]-1-
piperidinyl}sulfonyl)-2-thienyl]methyl}benzamide;
N-{[5-({4-[(4-butoxybenzyl)amino]-1-
piperidinyl}sulfonyl)-2-thienyl]methyl}-4-chloroben-
zamide;
4-chloro-N-{[5-({4-[(4-quinolinylmethyl)amino]-1-
piperidinyl}sulfonyl)-2-thienyl]methyl}benzamide;
N-{[5-({4-[(4-tert-butylbenzyl)amino]-1-
piperidinyl}sulfonyl)-2-thienyl]methyl}-4-chloroben-
zamide;
4-chloro-N-{[5-({4-[(4-phenoxybenzyl)amino]-1-
piperidinyl}sulfonyl)-2-thienyl]methyl}benzamide;
4-chloro-N-[(5-{[4-({4-[(trifluoromethyl)sulfanyl]
benzyl}amino)-1-piperidinyl]sulfonyl}-2-thienyl)me-
thyl]benzamide;
4-chloro-N-({5-[(4-{[4-(trifluoromethyl)benzyl]amino}-
1-piperidinyl)sulfonyl]-2-thienyl}methyl)benzamide;
3-methoxy-N-({5-[(4-{[2-(trifluoromethyl)benzyl]
amino}-1-piperidinyl)sulfonyl]-2-thienyl}methyl)ben-
zamide;
3-methoxy-N-[(5-{[4-({[6-(trifluoromethyl)-3-pyridinyl]
methyl}amino)-1-piperidinyl]sulfonyl}-2-thienyl)me-
thyl]benzamide;
N-[(5-{[4-(benzylamino)-1-piperidinyl]sulfonyl}-2-thie-
nyl)methyl]-3-methoxybenzamide;
3-methoxy-N-[(5-{[4-({1-[4-(trifluoromethyl)phenyl]
propyl}amino)-1-piperidinyl]sulfonyl}-2-thienyl)me-
thyl]benzamide;
3-methoxy-N-[(5-{[4-({1-methyl-1-[4-(trifluoromethyl)
phenyl]ethyl}amino)-1-piperidinyl]sulfonyl}-2-thie-
nyl)methyl]benzamide;
4-chloro-N-[(5-{[4-({1-[4-(trifluoromethyl)phenyl]
ethyl}amino)-1-piperidinyl]sulfonyl}-2-thienyl)me-
thyl]benzamide;
4-chloro-N-[(5-{[4-({1-methyl-1-[4-(trifluoromethyl)
phenyl]ethyl}amino)-1-piperidinyl]sulfonyl}-2-thie-
nyl)methyl]benzamide;
4-chloro-N-[(5-{[2-({[4-(trifluoromethyl)benzyl]
amino}methyl)-1-pyrrolidinyl]sulfonyl}-2-thienyl)me-
thyl]benzamide;
4-chloro-N-[(5-{[(3R)-3-({[4-(trifluoromethyl)benzyl]
amino}methyl)pyrrolidinyl]sulfonyl}-2-thienyl)me-
thyl]benzamide;
4-chloro-N-({5-[(3-{[4-(trifluoromethyl)benzyl]amino}-
1-piperidinyl)sulfonyl]-2-thienyl}methyl)benzamide;
4-chloro-N-{[5-({3-[(hexylamino)methyl]-1-
piperidinyl}sulfonyl)-2-thienyl]methyl}benzamide;
4-chloro-N-({5-[(3-{[4-(trifluoromethyl)benzyl]amino}-
1-pyrrolidinyl)sulfonyl]-2-thienyl}methyl)benzamide;
4-chloro-N-{[5-({(3R)-3-[(hexylamino)methyl]
pyrrolidinyl}sulfonyl)-2-thienyl]methyl}benzamide;
4-chloro-N-[(5-{[3-({[4-(trifluoromethyl)benzyl]
amino}methyl)-1-piperidinyl]sulfonyl}-2-thienyl)me-
thyl]benzamide;
2-oxo-N-({5-[(4-{[4-(trifluoromethyl)benzyl]amino}-1-
piperidinyl)sulfonyl]-2-thienyl}methyl)-1,2-dihydro-3-
pyridinecarboxamide;
N-[(5-{[4-(hexylamino)-1-piperidinyl]sulfonyl}-2-thie-
nyl)methyl]-2-oxo-1,2-dihydro-3-pyridinecarboxam-
ide;
N-[(5-{[4-(hexylamino)-1-piperidinyl]sulfonyl}-2-thie-
nyl)methyl]-2-hydroxybenzamide;
2-hydroxy-N-({5-[(4-{[4-(trifluoromethyl)benzyl]
amino}-1-piperidinyl)sulfonyl]-2-thienyl}methyl)ben-
zamide;

N-[(5-{[4-(hexylamino)-1-piperidinyl]sulfonyl}-2-thienyl)methyl]-2-thioxo-1,2-dihydro-3-pyridinecarboxamide;

2-thioxo-N-({5-[(4-{[4-(trifluoromethyl)benzyl]amino}-1-piperidinyl)sulfonyl]-2-thienyl}methyl)-1,2-dihydro-3-pyridinecarboxamide;

N-[(5-{[4-(butylamino)-1-piperidinyl]sulfonyl}-2-thienyl)methyl]-2-oxo-1,2-dihydro-3-pyridinecarboxamide;

N-({5-[(4-{ethyl[4-(trifluoromethyl)benzyl]amino}-1-piperidinyl)sulfonyl]-2-thienyl}methyl)-3-methoxybenzamide;

4-chloro-N-[(5-{[4-({imino[4-(trifluoromethyl)phenyl]methyl}amino)-1-piperidinyl]sulfonyl}-2-thienyl)methyl]benzamide;

1-[(5-{[(4-chlorobenzoyl)amino]methyl}-2-thienyl)sulfonyl]-4-(hexylamino)proline;

ethyl 2-{[4-(hexylamino)piperidin-1-yl]sulfonyl}-5-{[(3-methoxybenzoyl)amino]methyl}thiophene-3-carboxylate;

N-{[5-{[4-(hexylamino)piperidin-1-yl]sulfonyl}-4-(trimethylsilyl)thien-2-yl]methyl}-3-methoxybenzamide;

N-({5-{[4-(hexylamino)piperidin-1-yl]sulfonyl}-4-[hydroxy(phenyl)methyl]thien-2-yl}methyl)-3-methoxybenzamide;

5-[(3-Methoxy-benzoylamino)-methyl]-2-[4-(4-trifluoromethyl-benzylamino)-piperidine-1-sulfonyl]-thiophene-3-carboxylic acid ethyl ester; and N-[(4-chloro-5-{[4-(hexylamino)piperidin-1-yl]sulfonyl}thien-2-yl)methyl]-3-methoxybenzamide.

6. A method for treating type II diabetes, comprising:
administering to a mammal in need of treatment an effective amount of a sulfonamide compound according to formula II to treat type II diabetes

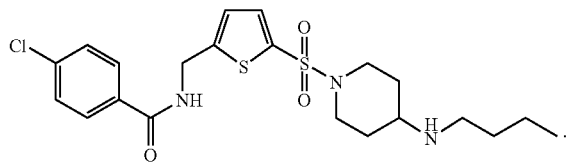

(II)

7. The method of claim 6, wherein the sulfonamide derivative of formula (II) is administered to the mammal in combination with at least one supplementary drug selected from the group consisting of insulin, 2-[(4-bromo-2-fluorophenyl)methyl]-6-fluoro-(9CI); Glycine, N-[[6-methoxy-5-(trifluoromethyl)-1-naphtalenyl]thioxomethyl]-N-methyl-(9CI); Spiro[4H-1-benzopyran-4,4'-imidazoline]-2',5'-dione, 6-fluoro-2,3-dihydro-, (4S)-(9CI); Methosorbinil; 1-Phtalazineacetic acid, 3,44-dihydro-4-oxo-3-[[5-(trifluoromethyl)-2-benzothiazolyl]methyl]-(9CI); 3-Thiazolidineacetic acid, 5-[(2E)-2-methyl-3-phenyl-2-propenylidene]-4-oxo-2-thioxo-, (5Z)-(9CI); 3-[(4-bromo-2-fluorophenyl)methyl]-7-chloro-3,4-dihydro-2,4-dioxo-1(2H)-quinazoline acetic acid; 2,7-difluorospiro(9H-fluorene-9,4'-imidazolidine)-2',5'-dione; 1-Phtalazineacetic acid, 3-[(4-bromo-2-fluorophenyl)methyl]3,4-dihydro-4-oxo-(9CI); 3-Thiazolidineacetic acid, 5-[(2E)-2-methyl-3-phenyl-2-propenylidene]-4-oxo-2-thioxo-, (5Z)-(9CI); {3-[(4,5,7-trifluorobenzothiazol-2-yl)methyl]-5-methylphenylacetic acid}; 5-(3-ethoxy-4-pentyloxyphenyl)-2,4-thiazolidinedione; Glycine, N[(7-fluoro-9-oxo-9H-xanthen-2-yl)sulfonyl]-N-methyl-)9CI), Reg. No. 124066-40-6)); 2,3-dihydro-2,8-bis(1-methylethyl)-3-thioxox-4H-1,4-benzoxazine-4-acetic acid of the chloride salt form (4H-1,4-Benzoxazine-4-acetic acid, 2,3-dihydro-2,8-bis(1-methylethyl)-3-thioxo-(9CI); (3',5'-dimethyl-4'-nitromethylsulfonyl-2-(2-tolyl)acetanilide); 3,4-dihydro-2,8-diisopropyl-3-thioxo-2H-1,4-benzoxazine-4-acetic acid; 1-[(3-bromo-2-benzofuranyl)sulfonyl]-2,4-imidazolidinedione; 1-Imidazolidineacetic acid, 3-[(3-nitrophenyl)methyl]-2,4,5-trioxo-9(CI); 1-phtalazineacetic acid, 3,4-dihydro-4-oxo-3-[(5-trifluoromethyl)-2-benzothiazolyl]-methyl]; Spiro[4H-1-benzopyran-4,4-imidazolidine]-2',5'-dione; 6-fluoro-2,3-dihydro-2-methyl-, (2R,4S)-(9CI); 2H-1,4-Benzothiazine-2-acetic acid, 3,4-dihydro-3-oxo-4-[(4,5,7-trifluoro-2-benzothiazolyl)methyl]-(9CI); Spiro[pyrrolidine-3,6'(5'H)-pyrrolo[1,2,3-de][1,4]benzoxazine]-2,5,5'-trione, 8'-chloro-2'-3'-dihydro-(9CI) (also known as AND 138 or 8-chloro-2',3'-dihydrospiro[pyrolizine-3,6'(5H)-pyrrolo-[1,2,3-de]-[1,4]benzoxazine]2,5,5'-trione); 6-fluoro-2,3-dihydro-2',5'-dioxo-(2S-cis)-spiro[4H-1-benzopyran-4,4'-imidazolidine]-2-carboxamide;

miglitol or acarbose, or the pharmaceutically acceptable salt form thereof;

glipizide, Glyburide (Glibenclamide) Clorpropamide, Tolbutamide, Tolazamide and Glimepiride, and pharmaceutically acceptable salt forms thereof.

8. The method of claim 6, wherein the sulfonamide derivative of formula (II) is administered to the mammal in combination with at least one supplementary drug selected from the group consisting of a rapid acting insulin, an intermediate acting insulin, a long acting insulin, a combination of intermediate and rapid acting insulins, Minalrestat, Tolrestat, Sorbinil, Methosorbinil, Zopolrestat, Epalrestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, SNK-860, Miglitol, Acarbose, Glipizide, Glyburide, Chlorpropamide, Tolbutamide, Tolazamide, and Glimepriride.

9. The method of claim 6, wherein the sulfonamide derivative of formula (II) is administered orally, rectally, transdermally, subcutaneously, intraveneously, intramuscularly, intrathecally, intraperiodontally, and intranasaly.

* * * * *